US009034862B2

(12) United States Patent
Lippard et al.

(10) Patent No.: US 9,034,862 B2
(45) Date of Patent: May 19, 2015

(54) COMPOSITIONS AND METHODS FOR THE TREATMENT OF CANCER

(75) Inventors: Stephen J. Lippard, Cambridge, MA (US); Ga Young Park, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 13/529,965

(22) Filed: Jun. 21, 2012

(65) Prior Publication Data

US 2013/0029959 A1    Jan. 31, 2013

Related U.S. Application Data

(60) Provisional application No. 61/499,439, filed on Jun. 21, 2011, provisional application No. 61/506,808, filed on Jul. 12, 2011.

(51) Int. Cl.
*C07F 15/00* (2006.01)
*A61K 31/473* (2006.01)

(52) U.S. Cl.
CPC .................................. *C07F 15/0093* (2013.01)

(58) Field of Classification Search
CPC . A61K 31/282; A61K 31/473; C07F 15/0093
See application file for complete search history.

(56) References Cited

U.S. PATENT DOCUMENTS

| | | | |
|---|---|---|---|
| 4,843,161 | A | 6/1989 | Lippard et al. |
| 5,244,919 | A | 9/1993 | Abrams et al. |
| 6,806,289 | B1 | 10/2004 | Lippard et al. |
| 7,138,520 | B2 | 11/2006 | Lippard et al. |
| 8,729,286 | B2 | 5/2014 | Lippard et al. |
| 2004/0235712 | A1 | 11/2004 | Lippard et al. |
| 2005/0090478 | A1 | 4/2005 | Barenholz et al. |
| 2007/0082882 | A1 | 4/2007 | Farrell |
| 2007/0104654 | A1 | 5/2007 | Hsieh et al. |
| 2007/0154398 | A1 | 7/2007 | Wang et al. |
| 2010/0330197 | A1* | 12/2010 | Higashiguchi et al. ........ 424/638 |
| 2011/0257261 | A1 | 10/2011 | Lippard et al. |
| 2011/0300219 | A1 | 12/2011 | Lippard et al. |
| 2013/0303606 | A1 | 11/2013 | Lippard et al. |
| 2014/0274988 | A1 | 9/2014 | Lippard et al. |
| 2014/0343139 | A1 | 11/2014 | Lippard et al. |

FOREIGN PATENT DOCUMENTS

| | | |
|---|---|---|
| DE | 19623746 A1 | 12/1997 |
| EP | 0 199 524 B1 | 2/1992 |
| EP | 0 679 656 A1 | 11/1995 |
| WO | WO 2005/092298 A1 | 10/2005 |
| WO | WO 2006/108276 A1 | 10/2006 |
| WO | WO 2007/021852 A2 | 2/2007 |
| WO | WO 2007/124314 A2 | 11/2007 |
| WO | WO 2007/133807 A2 | 11/2007 |
| WO | WO 2008/121949 A1 | 10/2008 |
| WO | WO 2009/032172 A2 | 3/2009 |
| WO | WO 2010/047765 A2 | 4/2010 |
| WO | WO 2010/150036 A1 | 12/2010 |
| WO | WO 2012/177935 A1 | 12/2012 |

OTHER PUBLICATIONS

Sporn et al. "Chemoprevention of Cancer". Carcinogenesis. 2000; 21(3):525-530.*
Thoppil et al. "Terpenoids as Potential Chemopreventive and Therapeutic Agents in Liver Cancer". World J Hepatol. Sep. 27, 2011; 3(9):228-249.*
Costello et al. "Evidence for Changes in RREB-1, ZIP3, and Zinc in the Early Development of Pancreatic Adenocarcinoma". J Gastrointest Canc. 2012; 43:570-578.*
Kostova I. "Platinum Complexes as Anticancer Agents". Recent Patents on Anti-Cancer Drug Discovery. 2006; 1:1-22.*
Zorbas-Seifried et al. "Reversion of Structure-Activity Relationships of Antitumor Platinum Complexes by Acetoxime but Not Hydroxylamine Ligands". Mol Pharmacol. 2007; 71:357-365.*
Osol A. [Editor]. "Chapter 27: Structure-Activity Relationship and Drug Design". Remington's Pharmaceutical Sciences (Sixtenth Edition). Mack Publishing. 1980. pp. 420-435.*
Martin et al. "Do Structurally Similar Molecules Have Similar Biological Activity?" Journal of Medicinal Chemistry. 2002; 45:4350-4358.*
Lippard SJ. "The Art of Chemistry". Nature. 2002; 416:587.*
Dorwald FZ. "Side Reactions in Organic Synthesis: A Guide to Successful Design". Wiley VCH Verlag GmbH & Co. KGaA. 2005. pp. 1-15.*
Hall et al. Platinum(IV) antitumour compounds: their bioinorganic chemistry. Coord Chem Rev. 2002; 232:49-67.
International Search Report and Written Opinion for PCT/US2008/010213 mailed Mar. 24, 2009.
International Preliminary Report on Patentability for PCT/US2008/010213 mailed Mar. 11, 2010.
International Search Report and Written Opinion for PCT/US2009/004846 mailed Dec. 8, 2009.
International Preliminary Report on Patentability for PCT/US2009/004846 mailed Mar. 10, 2011.
International Search Report and Written Opinion for PCT/US2009/005687 mailed May 26, 2010.
International Preliminary Report on Patentability for PCT/US2009/005687 mailed May 5, 2011.
International Search Report and Written Opinion for PCT/US2012/043620 mailed Sep. 28, 2012.
International Preliminary Report on Patentability for PCT/US2012/043620 mailed Jan. 9, 2014.

(Continued)

*Primary Examiner* — Leslie A. Royds Draper
(74) *Attorney, Agent, or Firm* — Wolf, Greenfield & Sacks, P.C.

(57) ABSTRACT

The present invention relates to compositions, kits, and methods for treatment of cancers. In some cases, the composition comprises a platinum compound comprising a phenanthridine ligand.

8 Claims, 13 Drawing Sheets

(56) References Cited

OTHER PUBLICATIONS

International Search Report and Written Opinion for PCT/US2012/043626 mailed Oct. 8, 2012.
International Preliminary Report on Patentability for PCT/US2012/043626 mailed Jan. 9, 2014.
Al-Allaf et al., Platinum(II) and palladium(II) complexes analogous to oxaliplatin with different cyclohexyldicarboxylate isomeric anions and their in vitro antitumour activity. Structural elucidation of [Pt(C2O4)(cis-dach)]. Transition Metal Chemistry. 2003;28: 717-21.
Ang et al., Transcription inhibition by platinum-DNA cross-links in live mammalian cells. J Am Chem Soc. Jun. 2, 2010;132(21):7429-35. doi: 10.1021/ja101495v.
Bauer et al., Monofunctional platinum amine complexes destabilize DNA significantly. Eur J Biochem. Sep. 1, 1998;256(2):253-60.
Cohen et al., Binding of cis- and trans-dichlorodiammineplatinum(II) to DNA: evidence for unwinding and shortening of the double helix. Science. Mar. 9, 1979;203(4384):1014-6.
Comess et al., Replication inhibition and translesion synthesis on templates containing site-specifically placed cis-diamminedichloroplatinum(II) DNA adducts. Biochemistry. Apr. 28, 1992;31(16):3975-90.
De Pascali et al., First Examples of β-Diketonate Platinum(II) Complexes with Sulfoxide Ligands. Eur Journal of Inorg Chem. Feb. 2005; (4): 788-96.
De Pascali et al., Mutagenic Tests Confirm That New Acetylacetonate Pt(II) Complexes Induce Apoptosis in Cancer Cells Interacting with Nongenomic Biological Targets. Met Based Drugs. 2011;2011:763436. doi: 10.1155/2011/763436. Epub Apr. 10, 2011.
Desoize et al., Particular aspects of platinum compounds used at present in cancer treatment. Crit Rev Oncol Hematol. Jun. 2002;42(3):317-25.
Dhar et al., Current Status and Mechanism of Action of Platinum-Based Anticancer Drugs. Bioinorganic Medicinal Chemistry, Enzo Alessio, Ed. Wi-ley-VCH Verlag GmbH & Co. KgaA. Weinheim, Germany, Chapter 3. 2010:79-95.
Dhar et al., Mitaplatin, a potent fusion of cisplatin and the orphan drug dichloroacetate. Proc Natl Acad Sci U S A. Dec. 29, 2009;106(52):22199-204. doi: 10.1073/pnas.0912276106. Epub Dec. 10, 2009.
Dhar et al., Polyvalent oligonucleotide gold nanoparticle conjugates as delivery vehicles for platinum(IV) warheads. J Am Chem Soc. Oct. 21, 2009;131(41):14652-3. doi: 10.1021/ja9071282.
Dhar et al., Targeted delivery of cisplatin to prostate cancer cells by aptamer functionalized Pt(IV) prodrug-PLGA-PEG nanoparticles. Proc Natl Acad Sci U S A. Nov. 11, 2008;105(45):17356-61. doi: 10.1073/pnas.0809154105. Epub Oct. 31, 2008.
Dhar et al., Targeted single-wall carbon nanotube-mediated Pt(IV) prodrug delivery using folate as a homing device. J Am Chem Soc. Aug. 27, 2008;130(34):11467-76. doi: 10.1021/ja803036e. Epub Jul. 29, 2008.
Feazell et al., Soluble single-walled carbon nanotubes as longboat delivery systems for platinum(IV) anticancer drug design. J Am Chem Soc. Jul. 11, 2007;129(27):8438-9. Epub Jun. 15, 2007.
Fink et al., In vitro and in vivo resistance to cisplatin in cells that have lost DNA mismatch repair. Cancer Res. May 15, 1997;57(10):1841-5.
Fink et al., The role of DNA mismatch repair in platinum drug resistance. Cancer Res. Nov. 1, 1996;56(21):4881-6.
Giandomenico et al., Carboxylation of Kinetically Inert Platinum(IV) Hydroxy Complexes. An Entr.acte.ee into Orally Active Platinum(IV) Antitumor Agents. Inorg Chem. Mar. 1995;34(5):1015-21. doi: 10.1021/ic00109a004.
Gill et al., Synthese, kinetics and mechanism of formation of polynuclear hydroxo-bridged complexes of (trans-1,2-diaminocyclohexane)platinum(II). J Am Chem Soc. 1982;104:4598-604.
Graf et al., Platinum(IV)-chlorotoxin (CTX) conjugates for targeting cancer cells. J Inorg Biochem. May 2012;110:58-63. doi: 10.1016/j.jinorgbio.2012.02.012. Epub Feb. 23, 2012.
Hall et al., Basis for design and development of platinum(IV) anti-cancer complexes. J Med Chem. Jul. 26, 2007;50(15):3403-11. Epub Jun. 28, 2007.
Hoeschele et al., Synthesis and characterization of diastereomeric (substituted iminodiacetato)(1,2-diaminocyclohexane)platinum(II) complexess. Inorganic Chemistry. 1988;27:4106-13.
Hollis et al., Chemical and biological properties of a new series of cis-diammineplatinum(II) antitumor agents containing three nitrogen donors: cis-[Pt(NH3)2(N-donor)C1]+. J Med Chem. Jan. 1989;32(1):128-36.
Hollis et al., Mechanistic studies of a novel class of trisubstituted platinum(II) antitumor agents. Cancer Res. Apr. 1, 1991;51(7):1866-75.
Hollis et al., Synthesis and Structures of Platinum(III) Complexes of α-Pyridone, [X(NH3)2Pt(C5H4NO)2Pt(NH3)2X](NO3)2*nH2O (X-=C1-, NO2-, Br-). Inorg Chem. 1983;22:3637-44.
Howe-Grant et al., Aqueous Platinum (II) Chemistry; Binding to Biological Molecules. Metal Ions in Biological Systems. Sigel et al., eds. 1980;11:63-125.
Ivanov et al., Biological activity of platinum (II) complexes of the triamine type as a function of their composition and structure. Izv Akad Nauk Ser Biol. May-Jun. 1995;(3):281-90. English abstract found on p. 290.
Jamieson et al., Structure, Recognition, and Processing of Cisplatin-DNA Adducts. Chem Rev. 1999;99:2467-98.
Jin et al., Platinum(II) triammine antitumour complexes: structure-activity relationship with guanosine 5'-monophosphate (5'-GMP). Inorganica Chimica Acta. 2005;358:677-86.
Jung et al., RNA polymerase II blockage by cisplatin-damaged DNA. Stability and polyubiquitylation of stalled polymerase. J Biol Chem. Jan. 20, 2006;281(3):1361-70. Epub Nov. 7, 2005.
Kapp et al., Dinuclear alkylamine platinum(II) complexes of [1,2-bis(4-fluorophenyl)ethylenediamine]platinum(II): influence of endocytosis and copper and organic cation transport systems on cellular uptake. ChemMedChem. May 2006;1(5):560-4.
Kartalou et al., Mechanisms of resistance to cisplatin. Mutat Res. Jul. 1, 2001;478(1-2):23-43.
Kawai et al., Synthesis, structure and antitumor activity of a new water-soluble platinum complex, (1R,2R-cyclohexanediamine-N,N')[2-hydroxy-4-oxo-2-pentenoato(2-)-O2] platinum(II). Chem Pharm Bull (Tokyo). Feb. 1993;41(2):357-61.
Keck et al., Unwinding of supercoiled DNA by platinum-ethidium and related complexes. J Am Chem Soc. 1992;114:3386-90.
Kelland et al., The resurgence of platinum-based cancer chemotherapy. Nat Rev Cancer. Aug. 2007;7(8):573-84. Epub Jul. 12, 2007.
Kidani et al., Antitumor activity of 1,2-diaminocyclohexane—platinum complexes against sarcoma-180 ascites form. J Med Chem. Dec. 1978;21(12):1315-8.
Lebwohl et al., Clinical development of platinum complexes in cancer therapy: an historical perspective and an update. Eur J Cancer. Sep. 1998;34(10):1522-34.
Lee et al., Transcription-coupled and DNA damage-dependent ubiquitination of RNA polymerase II in vitro. Proc Natl Acad Sci U S A. Apr. 2, 2002;99(7):4239-44. Epub Mar. 19, 2002.
Lempers et al., The new antitumor compound, cis-[Pt(NH3)2(4-methylpyridine)C1]C1, does not form N7,N7-d(GpG) chelates with DNA. An unexpected preference for platinum binding at the 5'G in d(GpG). J Inorg Biochem. Sep. 1990;40(1):23-35.
Lovejoy et al., cis-Diammine(pyridine)chloroplatinum(II), a monofunctional platinum(II) antitumor agent: Uptake, structure, function, and prospects. Proc Natl Acad Sci U S A. Jul. 1, 2008;105(26):8902-7. doi: 10.1073/pnas.0803441105. Epub Jun. 25, 2008.
Lovejoy et al., Non-traditional platinum compounds for improved accumulation, oral bioavailability, and tumor targeting. Dalton Trans. Dec. 28, 2009;(48):10651-9. doi: 10.1039/b913896j. Epub Oct. 1, 2009.
Lovejoy et al., Spectrum of cellular responses to pyriplatin, a monofunctional cationic antineoplastic platinum(II) compound, in human cancer cells. Mol Cancer Ther. Sep. 2011;10(9):1709-19. doi: 10.1158/1535-7163.MCT-11-0250. Epub Jul. 12, 2011.
Margiotta et al., Sterically hindered complexes of platinum(II) with planar heterocyclic nitrogen donors. A novel complex with 1-methyl-

(56) References Cited

OTHER PUBLICATIONS cytosine has a spectrum of activity different from cisplatin and is able of overcoming acquired cisplatin resistance. J Inorg Biochem. Nov. 2006;100(11):1849-57. Epub Aug. 3, 2006.
Misset et al., Oxaliplatin clinical activity: a review. Crit Rev Oncol Hematol. Aug. 2000;35(2):75-93.
Mukhopadhyay et al., Conjugated platinum(IV)-peptide complexes for targeting angiogenic tumor vasculature. Bioconjug Chem. Jan. 2008;19(1):39-49. Epub Sep. 11, 2007.
Muscella et al., [Pt(O,O'-acac)(gamma-acac)(DMS)], a new Pt compound exerting fast cytotoxicity in MCF-7 breast cancer cells via the mitochondrial apoptotic pathway. Br J Pharmacol. Jan. 2008;153(1):34-49. Epub Nov. 19, 2007.
Muscella et al., New platinum(II) complexes containing both an O,O'-chelated acetylacetonate ligand and a sulfur ligand in the platinum coordination sphere induce apoptosis in HeLa cervical carcinoma cells. Biochem Pharmacol. Jun. 30, 2007;74(1):28-40. Epub Mar. 31, 2007.
Muscella et al., Sublethal concentrations of the platinum(II) complex [Pt(O,O'-acac)(gamma-acac)(DMS)] alter the motility and induce anoikis in MCF-7 cells. Br J Pharmacol. Jul. 2010;160(6):1362-77. doi: 10.1111/j.1476-5381.2010.00782.x.
Page et al., Effect of the diaminocyclohexane carrier ligand on platinum adduct formation, repair, and lethality. Biochemistry. Jan. 30, 1990;29(4):1016-24.
Park et al., Phenanthriplatin, a monofunctional DNA-binding platinum anticancer drug candidate with unusual potency and cellular activity profile. Proc Natl Acad Sci U S A. Jul. 24, 2012;109(30):11987-92. doi: 10.1073/pnas.1207670109. Epub Jul. 6, 2012.
Peer et al., Nanocarriers as an emerging platform for cancer therapy. Nat Nanotechnol. Dec. 2007;2(12):751-60. doi: 10.1038/nnano.2007.387.
Pérez et al., Current status of the development of trans-platinum antitumor drugs. Crit Rev Oncol Hematol. Aug. 2000;35(2):109-20.
Pinto et al., Binding of the antitumor drug cis-diamminedichloroplatinum(II) (cisplatin) to DNA. Biochim Biophys Acta. 1985;780(3):167-80.
Portney et al., Nano-oncology: drug delivery, imaging, and sensing. Anal Bioanal Chem. Feb. 2006;384(3):620-30. Epub Jan. 27, 2006.
Reardon et al., Efficient nucleotide excision repair of cisplatin, oxaliplatin, and Bis-aceto-ammine-dichloro-cyclohexylamine-platinum(IV) (JM216) platinum intrastrand DNA diadducts. Cancer Res. Aug. 15, 1999;59(16):3968-71.
Reardon et al., Purification and characterization of *Escherichia coli* and human nucleotide excision repair enzyme systems. Methods Enzymol. 2006;408:189-213.
Sakai et al., A New One-Dimensional Platinum System Consisting of Carboxylate-Bridged cis-Diammineplatinum Dimers1. JACS. 1998;120:11353-63.
Schwartz et al., Preparation and antitumor evaluation of water-soluble derivatives of dichloro(1,2-diaminocyclohexane)platinum(II). Cancer Treat Rep. Nov. 1977;61(8):1519-25.
Silverman et al., 2.4-A crystal structure of the asymmetric platinum complex [Pt(ammine)(cyclohexylamine)]2+ bound to a dodecamer DNA duplex. J Biol Chem. Dec. 20, 2002;277(51):49743-9. Epub Oct. 10, 2002.
Spingler et al., 2.4 A crystal structure of an oxaliplatin 1,2-d(GpG) intrastrand cross-link in a DNA dodecamer duplex. Inorg Chem. Oct. 22, 2001;40(22):5596-602.
Stephen et al., The structural characterisation and elucidation of the electronic structure of the mononuclear Pt(III) complex [Pt([9]aneS3)2]3+ ([9]aneS3=1,4,7-trithiacyclononane). Chem Commun (Camb). Nov. 30, 2008;(44):5707-9. doi: 10.1039/b811645h. Epub Sep. 30, 2008.
Takahara et al., Crystal structure of the anticancer drug cisplatin bound to duplex DNA. J Am Chem Soc. 1996;118:12309-21.
Todd et al., Inhibition of transcription by platinum antitumor compounds. Metallomics. 2009;1(4):280-91. doi: 10.1039/b907567d.
Trafton, MIT researchers see alternative to common colorectal cancer drug. News Office. Jun. 17, 2008. Last accessed Jun. 23, 2008. 2 pages.
Wang et al., Cellular processing of platinum anticancer drugs. Nat Rev Drug Discov. Apr. 2005;4(4):307-20.
Wang et al., X-ray structure and mechanism of RNA polymerase II stalled at an antineoplastic monofunctional platinum-DNA adduct. Proc Natl Acad Sci U S A. May 25, 2010;107(21):9584-9. doi: 10.1073/pnas.1002565107. Epub May 6, 2010.
Weiss et al., New cisplatin analogues in development. A review. Drugs. Sep. 1993;46(3):360-77.
Whittaker et al., The interaction of DNA-targeted platinum phenanthridinium complexes with DNA. Nucleic Acids Res. Sep. 1, 1998;26(17):3933-9.
Wilson et al., Acetate-bridged platinum(III) complexes derived from cisplatin. Inorg Chem. Sep. 17, 2012;51(18):9852-64. doi: 10.1021/ic301289j. Epub Sep. 4, 2012.
Wilson et al., In vitro anticancer activity of cis-diammineplatinum(II) complexes with β-diketonate leaving group ligands. J Med Chem. Jun. 14, 2012;55(11):5326-36. doi: 10.1021/jm3002857. Epub May 18, 2012.
Wilson et al., Synthesis, characterization, and cytotoxicity of platinum(IV) carbamate complexes. Inorg Chem. Apr. 4, 2011;50(7):3103-15. doi: 10.1021/ic2000816. Epub Mar. 1, 2011.
Wilson, New Constructs for Platinum Anticancer Prodrugs. Presentation. Oct. 19, 2011. 41 pages.
Wong et al., Current status of platinum-based antitumor drugs. Chem Rev. Sep. 8, 1999;99(9):2451-66.
Yalcin, Studies on cis-DDP, [Pt(Dach)(MePhSO)Cl]+ and [PtNH3)2(N-Py)Cl]+ binding to fumarase. Drug Metabol Drug Interact. 1995;12(2):105-15.
Yonezawa et al., Cisplatin and oxaliplatin, but not carboplatin and nedaplatin, are substrates for human organic cation transporters (SLC22A1-3 and multidrug and toxin extrusion family). J Pharmacol Exp Ther. Nov. 2006;319(2):879-86. Epub Aug. 16, 2006.
Zamble et al., Cisplatin and DNA repair in cancer chemotherapy. Trends Biochem Sci. Oct. 1995;20(10):435-9.
Zamble et al., Repair of cisplatin—DNA adducts by the mammalian excision nuclease. Biochemistry. Aug. 6, 1996;35(31):10004-13.
Zhang et al., Organic cation transporters are determinants of oxaliplatin cytotoxicity. Cancer Res. Sep. 1, 2006;66(17):8847-57.
Zhu et al., Monofunctional platinum-DNA adducts are strong inhibitors of transcription and substrates for nucleotide excision repair in live mammalian cells. Cancer Res. Feb. 1, 2012;72(3):790-800. doi: 10.1158/0008-5472.CAN-11-3151. Epub Dec. 16, 2011.

* cited by examiner

COMPOSITIONS AND METHODS FOR THE TREATMENT OF CANCER

RELATED APPLICATIONS

This application claims the benefit of U.S. Provisional Patent Application Ser. No. 61/499,439, filed Jun. 21, 2011, entitled "COMPOSITIONS AND METHODS FOR THE TREATMENT OF CANCER," by Lippard et al., and U.S. Provisional Patent Application Ser. No. 61/506,808 filed Jul. 12, 2011, entitled "COMPOSITIONS AND METHODS FOR THE TREATMENT OF CANCER," by Lippard et al., each herein incorporated by reference.

STATEMENT REGARDING FEDERALLY SPONSORED RESEARCH OR DEVELOPMENT

This invention was made with government support under Grant No. R01 CA034992, awarded by the National Institutes of Health. The government has certain rights in this invention.

FIELD OF THE INVENTION

The present invention relates to compositions, kits, and methods for treatment of cancers. In some cases, the composition comprises a platinum compound comprising a phenanthridine ligand.

BACKGROUND OF THE INVENTION

Platinum-based drugs are among the most active and widely used anticancer agents and cisplatin represents one of three FDA-approved, platinum-based cancer chemotherapeutics. Although cisplatin is effective against a number of solid tumors, especially testicular and ovarian cancer, its clinical use has been limited because of its toxic effects as well as the intrinsic and acquired resistance of some tumors to this drug. To overcome these limitations, platinum analogs with lower toxicity and greater activity in cisplatin-resistant tumors have been developed and tested, resulting in the approval of carboplatin and oxaliplatin in the United States. For example, carboplatin has the advantage of being less nephrotoxic, but its cross-resistance with cisplatin has limited its application in otherwise cisplatin-treatable diseases. Oxaliplatin, however, exhibits a different anticancer spectrum from that of cisplatin. It has been approved as the first or second line therapy in combination with 5-fluoruracil/leucovorin for advanced colorectal cancer, for which cisplatin and carboplatin are essentially inactive.

Accordingly, improved compositions and methods are needed.

SUMMARY OF THE INVENTION

In some embodiments, the present invention provides a composition of matter comprising a compound of formula (I):

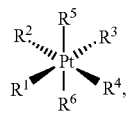

or a salt thereof, wherein:
each of $R^1$, $R^2$, and $R^3$ can be the same or different and each is a group comprising at least one of ammonia, an amine, or a leaving group, each optionally substituted;
$R^4$ is

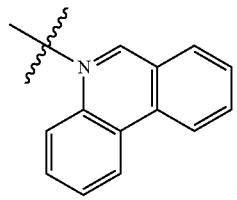

wherein each hydrogen atom of the aryl ring system is optionally replaced with a halide; and
each of $R^5$ and $R^6$ can be the same or different and are groups comprising hydroxyl, alkoxy, aryloxy, or acyloxy, each optionally substituted, or are absent.

In some embodiments, a composition comprising a compound having the structure:

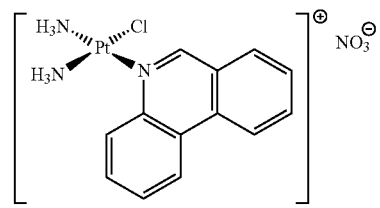

In some embodiments, the present invention also provides pharmaceutical composition comprising a composition as described herein or a pharmaceutically acceptable salt thereof, and one or more pharmaceutically acceptable carriers, additives and/or diluents.

In some embodiments, the present invention also provides kits for the treatment of cancer comprising a composition as described herein and instructions for use of the composition for treatment of cancer.

In some embodiments, the present invention also provides methods of treating cancer in a patient comprising administering a composition as described herein to the patient.

Figure 1:
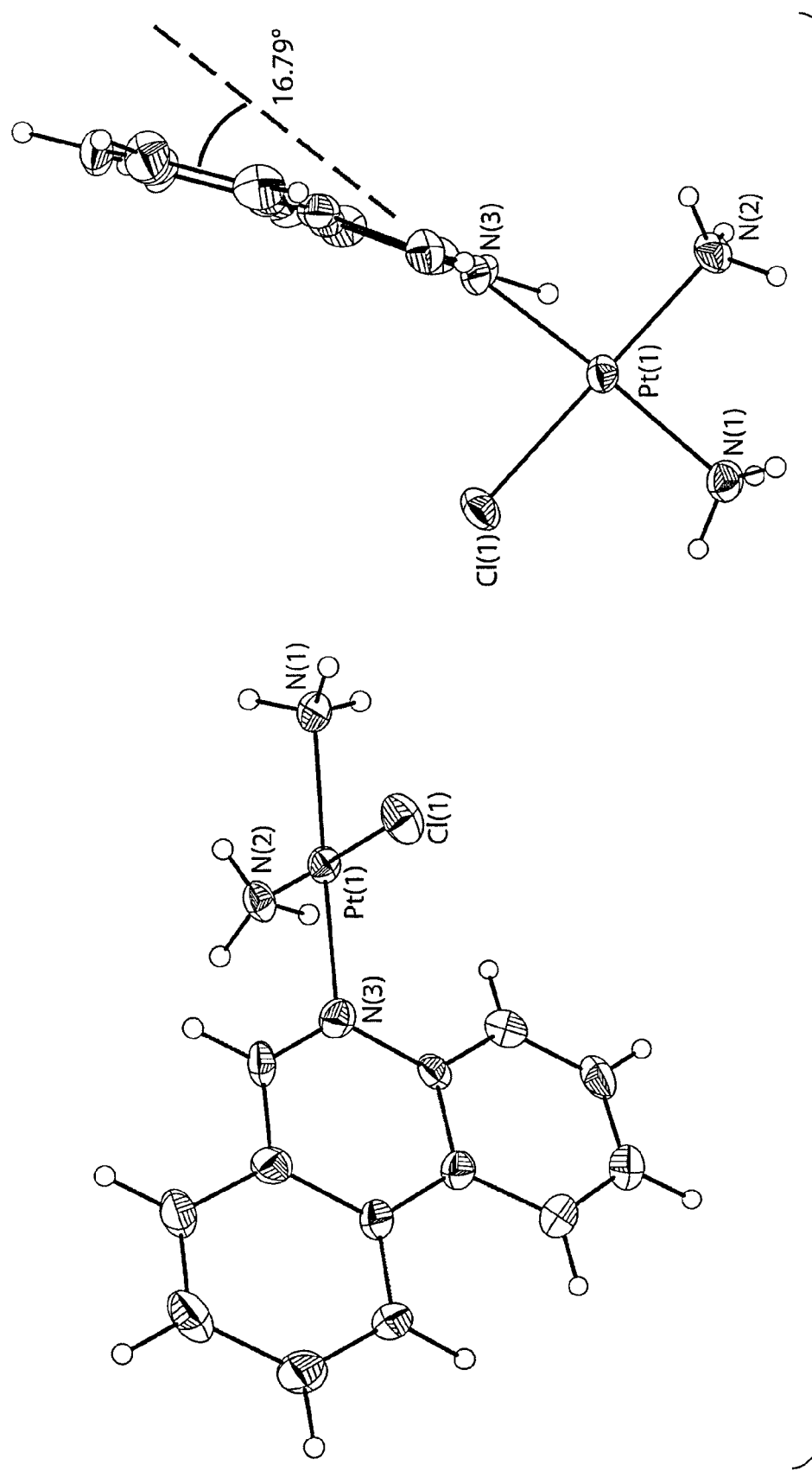
FIG. 1 shows ORTEP diagrams of cis-[Pt(NH$_3$)$_2$(phenanthridine)Cl]NO$_3$. Ellipsoids are drawn at the 50% probability level.

Other aspects, embodiments, and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

DETAILED DESCRIPTION

The invention generally provides compositions, preparations, formulations, kits, and methods useful for treating subjects having cancer or at risk of developing cancer. In some embodiments, a particle comprising a polymeric material and a platinum compound are provided. The subject matter of the present invention involves, in some cases, interrelated products, alternative solutions to a particular problem, and/or a plurality of different uses of one or more systems and/or articles.

In some aspects, the disclosure provides compounds and related compositions for use in treating subjects known to have (e.g., diagnosed with) cancer or subjects at risk of developing cancer. In some embodiments, methods of the invention include administering to a subject a therapeutically effective amount of a compound, or a therapeutic preparation, composition, or formulation of the compound as described herein, to a subject having or suspected of having a cancer. In some embodiments, as described herein, the compounds provided have surprising high cytotoxicity as compared to other commonly known platinum compounds (e.g., cisplatin) which are employed for the treatment of cancer.

In some embodiments, the compounds of the present invention are platinum compound comprising at least one phenanthridine ligand and a platinum atom. In some cases, the phenanthridine ligand is coordinated with the platinum atom of the platinum compound. As will be known to those of ordinary skill in the art, phenanthridine

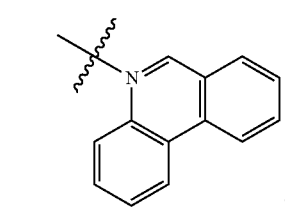

It should be noted, that in some embodiments, the phenanthridine ligand is optionally substituted, as described in more detail herein. That is, any hydrogen atom of a phenanthridine ligand may be optionally substituted with a suitable substituent. In some cases, the platinum atom comprised in the platinum compound has an oxidation state of II and is coordinated with four ligands, including the phenanthridine ligand. In other cases, the platinum atom comprised in the platinum compound has an oxidation state of IV and is coordinated with six ligands, including the phenanthridine ligand.

In some embodiments, a composition is provided comprising a compound of

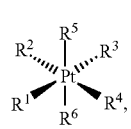

(I)

or a salt thereof, wherein:
each of $R^1$, $R^2$, and $R^3$ can be the same or different and each is a group comprising at least one of ammonia, an amine, or a leaving group, each optionally substituted;
$R^4$ is

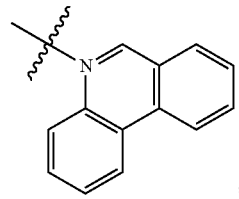

wherein each hydrogen atom of the aryl ring system is optionally replaced with a halide; and
each of $R^5$ and $R^6$ can be the same or different and are groups comprising hydroxyl, alkoxy, aryloxy, or acyloxy, each optionally substituted, or are absent. In some cases, any two or three of $R^1$, $R^2$ and/or $R^3$ may be joined together to form a bidentate or tridentate ligand, respectively.

In some cases, a least one of $R^5$ or $R^6$ may be functionalized such that it may be associated with a nanoparticle or particle and/or another solid support (e.g., via a covalent bond), and/or may be associated with a nanoparticle. For example, the nanoparticle may comprise a polymeric material (e.g., poly [(lactic)co-glycolic] acid or similar construct) and may optionally be functionalized with a targeting moiety such as an aptamer directed against a cancer cell target, as described herein. In some embodiments, the platinum compound may be dispersed or encapsulated within a polymeric material. The platinum compound may or might not be associated with the polymeric material via a covalent bond. Without wishing to be bound by theory, the association of a nanoparticle or particle with a platinum compound and/or encapsulation of the platinum compound (e.g., in an emulsion, in a particle) may aid in protecting the platinum atom from being reduced (e.g., when exposed to blood and/or another biological reducing environment) prior to entry into a cancer cell and/or may reduce the toxicity of the platinum compound.

In some cases, $R^4$ is:

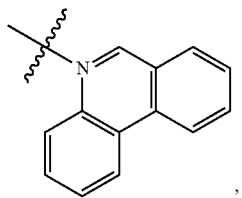

wherein each hydrogen atom of the aryl ring system is optionally replaced with a suitable substituent.

In some cases, the compound of formula (I) comprises a compound of formula (II) or (III):

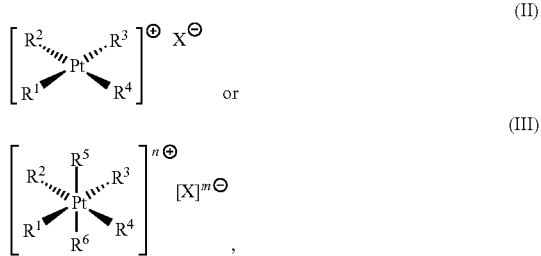

wherein, X is a counterion, n and m are 1 or n and m are 2, and $R^1$-$R^6$ are as described herein.

In some cases, the compound of formula (I) comprises a compound of formula

wherein $R^1$-$R^6$ are as described herein.

The following descriptions may be applied to any one of the compounds of formula (I)-formula (V) shown above.

In some embodiments, at least one of $R^1$, $R^2$, and $R^3$ is a leaving group. In some embodiments, at least two of $R^1$, $R^2$, and $R^3$ is a leaving group. As used herein, a "leaving group" is given its ordinary meaning in the art and refers to an atom or a group capable of being displaced by a nucleophile. Examples of suitable leaving groups include, but are not limited to, halides (such as chloride, bromide, and iodide), alkanesulfonyloxy, arenesulfonyloxy, alkyl-carbonyloxy (e.g., acetoxy, carboxylate), arylcarbonyloxy, mesyloxy, tosyloxy, trifluoromethane-sulfonyloxy, aryloxy, methoxy, N,O-dimethylhydroxylamino, pixyl, oxalato, malonato, and the like. A leaving group may also be a bidentate, tridentate, or other multidentate ligand. In some embodiments, the leaving group is a halide or carboxylate. In some embodiments, the leaving group is chloride. In some embodiments, each of $R^1$ and $R^2$ are $N(R')_3$ and/or $R^3$ is a halide, wherein each R' is a suitable substituent (e.g., hydrogen, alkyl, aryl, heteroalkyl, heteroaryl, each optionally substituted). In some embodiments, each of $R^1$ and $R^2$ are $NH_3$ and/or $R^3$ is halide. In some embodiments, each of $R^1$ and $R^2$ are $NH_3$ and $R^3$ is Cl. In some embodiments, at least one of $R^1$, $R^2$, and $R^3$ is ammonia. In some embodiments, at least one of $R^1$, $R^2$, and $R^3$ is an amine. In some cases, the amine has the structure $N(R')_3$, wherein each R' can be the same or different and is a suitable substituent. In some cases, each R' can be the same or different and is hydrogen, alkyl, aryl, heteroalkyl, or heteroaryl, each optionally substituted. In some cases, each R' can be the same or different and is hydrogen, alkyl, or aryl, each optionally substituted. In some cases, each R' can be the same or different and is hydrogen or alkyl, optionally substituted.

In some embodiments, the ligands associated with the platinum center in the platinum compound (e.g., $R^1$-$R^3$, or $R^1$-$R^4$, or $R^1$-$R^6$) may include functional groups capable of interaction with a metal center, e.g., heteroatoms such as nitrogen, oxygen, sulfur, and phosphorus. Non-limiting examples of compounds which the ligands may comprise include amines (primary, secondary, and tertiary), aromatic amines, amino groups, amido groups, nitro groups, nitroso groups, amino alcohols, nitriles, imino groups, isonitriles, cyanates, isocyanates, phosphates, phosphonates, phosphites, (substituted) phosphines, phosphine oxides, phosphorothioates, phosphoramidates, phosphonamidites, hydroxyls, carbonyls (e.g., carboxyl, ester and formyl groups), aldehydes, ketones, ethers, carbamoyl groups, thiols, sulfides, thiocarbonyls (e.g., thiolcarboxyl, thiolester and thiolformyl groups), thioethers, mercaptans, sulfonic acids, sulfoxides, sulfates, sulfonates, sulfones, sulfonamides, sulfamoyls, and sulfinyls. In other cases, at least some of the ligands (e.g., $R^1$-$R^3$, or $R^1$-$R^4$, or $R^1$-$R^6$) may be aryl group, alkenyl group, alkynyl group or other moiety which may bind the metal atom in either a sigma- or pi-coordinated fashion.

Some embodiments of the invention comprise compounds having two leaving groups positioned in a cis configuration, i.e., the compound may be a cis isomer. However, it should be understood that compounds of the invention may also have two leaving groups positioned in a trans configuration, i.e., the compound may be a trans isomer. Those of ordinary skill in the art would understand the meaning of these terms. In some cases, $R^1$ and $R^2$ may be labile ligands and $R^3$ and $R^4$ (e.g., phenanthridine) may be non-labile ligands covalently bonded to the platinum metal center.

As noted above, in some cases, any two or three of $R^1$, $R^2$ and/or $R^3$ may be joined together to form a bidentate or tridentate ligand, respectively. As will be known to those of ordinary skill in the art, a bidentate ligand, when bound to a metal center, forms a metallacycle structure with the metal center, also known as a chelate ring. Bidentate ligands suitable for use in the present invention include species that have at least two sites capable of binding to a metal center. For example, the bidentate ligand may comprise at least two heteroatoms that coordinate the metal center, or a heteroatom and an anionic carbon atom that coordinate the metal center. Examples of bidentate ligands suitable for use in the invention include, but are not limited to, alkyl and aryl derivatives of moieties such as amines, phosphines, phosphites, phosphates, imines, oximes, ethers, thiolates, thioethers, hybrids thereof, substituted derivatives thereof, aryl groups (e.g., bisaryl, heteroaryl-substituted aryl), heteroaryl groups, and the like. Specific examples of bidentate ligands include ethylenediamine, 2,2'-bipyridine, acetylacetonate, oxalate, and the like. Other non-limiting examples of bidentate ligands include diimines, pyridylimines, diamines, imineamines, iminethioether, iminephosphines, bisoxazoline, bisphosphineimines, diphosphines, phosphineamine, salen and other alkoxy imine ligands, amidoamines, imidothioether fragments and alkoxyamide fragments, and combinations of the above ligands.

As will be known to those of ordinary skill in the art, a tridentate ligand generally includes species which have at least three sites capable of binding to a metal center. For example, the tridentate ligand may comprise at least three heteroatoms that coordinate the metal center, or a combination of heteroatom(s) and anionic carbon atom(s) that coordinate the metal center. Non-limiting examples of tridentate ligands include 2,5-diiminopyridyl ligands, tripyridyl moieties, triimidazoyl moieties, tris pyrazoyl moieties, and combinations of the above ligands.

As noted above, in some cases, the phenanthridine ligand (e.g., $R^4$) is optionally substituted wherein any hydrogen atom of the phenanthridine ligand may be optionally substituted with a suitable substituent. For example, the phenanthridine ligand (e.g., $R^4$) may comprise the formula:

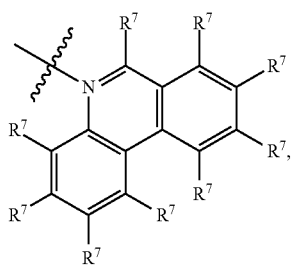

wherein each $R^7$ may be H or another suitable substituent. In some cases, at least one $R^7$ is not hydrogen. In some cases, each $R^7$ may be H or a halide (e.g., F, Cl, Br, I). In some cases, at least one $R^7$ is halide. In some cases, at least one $R^7$ is fluorine. In some cases, each $R^7$ is a halide. In some cases, each $R^7$ is fluorine. Other non-limiting examples of suitable $R^7$ groups include alkyl, aryl, heteroalkyl, heteroaryl, hydroxyl, amino, cyano, etc., each optionally substituted. In some embodiments, $R^4$ is not phenanthridine-1,9-diamine.

In some embodiments, release of $R^5$ and $R^6$ from a platinum(IV) compound may result in the formation of a platinum (II) compound, wherein the platinum (IV) compound may not be therapeutically active and the platinum (II) compound may be therapeutically active composition (e.g., useful for the treatment of disease, for example, cancer). In some cases, the release of $R^5$ and $R^6$ from the platinum center may be facilitated by a redox change of the platinum(IV) center. In some cases, the redox change may be accompanied by the release of $R^5$ and $R^6$ from the platinum(IV) center. In other cases, a redox change of the platinum(IV) center may promote the release of $R^5$ and $R^6$. For example, a redox change of the platinum(IV) center may cause a change in coordination geometry for the platinum center that reduces the number of ligands, thereby causing $R^5$ and $R^6$ to dissociate from the platinum center. In some embodiments, wherein the platinum compound is associated with a particle via at least one covalent bond (e.g., formed between any one of $R^1$-$R^6$ and the particle), release of ligand, which is covalently associated with the particle may result in dissociation of the platinum compound with the particle. In some embodiments, wherein $R^5$ or $R^6$ form a covalent bond with the particle, release of $R^5$ and $R^6$ from a platinum(IV) compound results in dissociation of the platinum compound with the particle.

In some embodiments, at least two of $R^1$, $R^2$, $R^3$, $R^4$, $R^{5'}$ and $R^6$ are selected such that, upon exposure to a cellular environment, a therapeutically active platinum(II) compound forms. For example, $R^1$ and $R^2$ may be essential groups for the formation of a therapeutically active platinum agent (e.g., groups which are required for a platinum compound to be therapeutically active compound, wherein $R^3$-$R^6$ may be any variety of ligands and/or optionally absent, and at least one of $R^3$-$R^6$ is an auxiliary compatibilizing moiety). In some cases, $R^3$, $R^4$, $R^5$, and $R^6$ may be the same or different and each may be a leaving groups or a precursor to a second therapeutically active compound. In some embodiments, upon exposure to a cellular environment, $R^3$, $R^4$, $R^5$, and $R^6$ may dissociate from the platinum center, and at least two new ligands may associate with the platinum center (e.g., $R^7$ and $R^8$, as shown in Equation 1) to form a therapeutically active platinum compound (e.g., $[Pt(R^1)(R^2)(R^7)(R^8)]$).

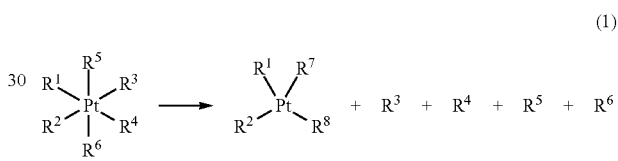

(1)

$R^7$ and $R^8$ may be the same or different and may be any suitable ligand as will be known to those of ordinary skill in the art, and are generally ligands or groups present in the environment surrounding the compound during dissociation of $R^3$, $R^4$, $R^5$ and/or $R^6$ (e.g., present in situ and/or in a cellular environment) and are capable of binding to platinum (e.g., water). In embodiments where a covalent bond is present between the platinum compound and a polymeric material, optionally formed as a particle, disassociation of the ligand, which comprises the covalent bond (e.g., $R^3$, $R^4$, $R^5$ and/or $R^6$) can result in disassociation of the platinum compound from the polymeric material and/or release of the platinum compound from the particle. It should be understood, that in some cases, less than all of $R^3$, $R^4$, $R^5$, and $R^6$ may dissociate from the platinum center and fewer than two ligands may associate with the platinum center. For example, $R^3$, $R^5$, and $R^6$ may dissociate from the platinum center and $R^8$ may associate, thereby forming a compound having the formula $[Pt(R^1)(R^2)(R^3)(R^8)]$. Those of ordinary skill in the art will be able to select appropriate combinations of ligands to form the desired therapeutically active complex.

In some cases, the at least two ligands are selected such that the ligands are cis to each other (e.g., $R^1$ and $R^2$, $R^1$ and $R^3$, $R^1$ and $R^5$, $R^1$ and $R^6$, $R^2$ and $R^4$, etc.). That is, the at least two ligands may not be trans to each other (e.g., $R^1$ and $R^4$, $R^2$ and $R^3$, $R^5$ and $R^6$). However, in some cases, the ligands may be selected such that they are trans to each other (e.g., in embodiments where the desired therapeutically active platinum agent has two essential ligands which are trans to each other). In some cases, the at least two ligands occupy equatorial positions of the compound. In some instances, however, one or more of the ligands may occupy an axial position of the compound. In some embodiments, more than two ligands may be essential for the formation of a therapeutically active platinum agent and those of ordinary skill in the art will be able to determine the required structure of the composition such that the essential ligands are present.

As described herein, some compounds of the present invention may be provided as a salt comprising a positively charged platinum compound and a counterion (e.g., "X"). The counterion X may be a weak or non-nucleophilic stabilizing ion. X may have a change of (−1), (−2), (−3), etc. In some cases, X has a change of (−1). In other cases, X has a charge of (−2). In some cases, the counterion is a negatively charged and/or non-coordinating ion. X may be any suitable counterion, including, but not limited to, halide (e.g., chloride, bromide, iodide), nitrate, nitrite, sulfate, sulfite, and triflate. In some embodiments, $X^{\ominus}$ is $NO_3^-$ In some embodiments, the compound of formula (I) has the structure:

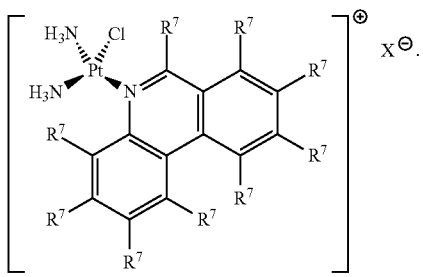

wherein X and $R^7$ are as described herein. In some cases, $X^{\ominus}$ is $NO_3^-$. In some cases, each $R^7$ is H. In some cases, $X^{\ominus}$ is $NO_3^-$ and each $R^7$ is H such that a compound of formula (I) is a compound of formula (VII):

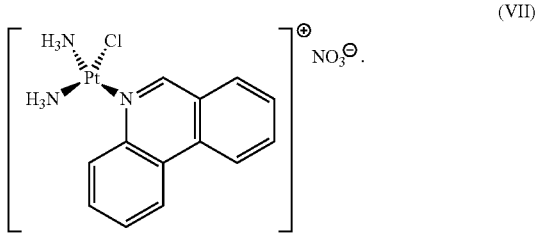

In some embodiments, the present invention provides a compound of formula (VII):

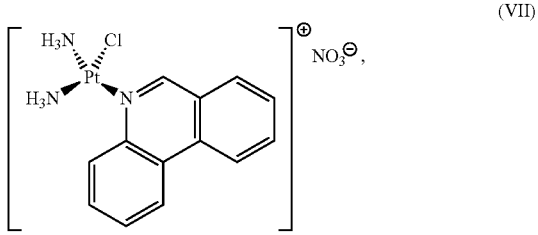

also referred to herein as phenanthriplatin.

In some embodiments, the compound has a molecular weight of 700 g/mol or less (e.g., 700 Da or less).

The invention also comprises homologs, analogs, derivatives, enantiomers, diastereomers, tautomers, cis- and trans-isomers, and functionally equivalent compositions of compounds described herein. "Functionally equivalent" generally refers to a composition capable of treatment of patients having cancer, or of patients susceptible to cancers. It will be understood that the skilled artisan will be able to manipulate the conditions in a manner to prepare such homologs, analogs, derivatives, enantiomers, diastereomers, tautomers, cis- and trans-isomers, and functionally equivalent compositions. Homologs, analogs, derivatives, enantiomers, diastereomers, tautomers, cis- and trans-isomers, and functionally equivalent compositions which are about as effective or more effective than the parent compound are also intended for use in the method of the invention. Such compositions may also be screened by the assays described herein for increased potency and specificity towards a cancer, preferably with limited side effects. Synthesis of such compositions may be accomplished through typical chemical modification methods such as those routinely practiced in the art. Another aspect of the present invention provides any of the above-mentioned compounds as being useful for the treatment of cancer.

Pt(II), Pt(III), and Pt(IV) compounds of the invention may be synthesized according to methods known in the art, including various methods described herein. For example, the method may comprise reaction of cisplatin with one or more ligand sources. In some cases, a Pt(IV) compound can be obtained by reaction of the parent Pt(II) species with, for example, hydrogen peroxide at temperatures ranging between 25-60° C. in an appropriate solvent, such as water or N,N-dimethylformamide. In some cases, a compound of formula (VII) may be formed by reacting cisplatin with a source of $NO_3^-$ (e.g., $AgNO_3$) followed by reaction with a phenanthridine ligand (e.g., optionally substituted).

In some embodiments, method for treating a subject having a cancer are provided, wherein the method comprises administering a therapeutically-effective amount of a compound, as described herein, to a subject having a cancer or suspected of having cancer. In some cases, the subject may be otherwise free of indications for treatment with said compound. In some cases, methods include use of cancer cells, including but not limited to mammalian cancer cells. In some instances, the mammalian cancer cells are human cancer cells.

In some embodiments, the compounds of the invention possess one or more desirable, but unexpected, combinations of properties, including increased activity and/or cytotoxicity, and reduction of adverse side effects. These compounds have been found to inhibit cancer growth, including proliferation, invasiveness, and metastasis, thereby rendering them particularly desirable for the treatment of cancer.

Interestingly, the compounds of the present invention comprising a phenanthridine ligand have substantially greater cytotoxicity as compared to other commonly employed platinum compounds (e.g., cisplatin; see Example 1) used for the treatment of cancer. Without wishing to be bound by theory, this may be due to, in part, to the angle at which the phenanthridine ligand is in relation to the remainder of the platinum compound. As shown in FIG. 1, in the solid state crystal structure, the phenanthridine ligand in the compound of formula (VII) is at a dihedral angle of 16.79°, which may help its DNA adducts block transcription in cancer cells (see below) while at the same time limiting the ability to inactivate the platinum compound by attack it at an axial position. This better geometry may compared to that other related compounds (e.g., comprising a pyridine ligand) which have zero or low dihedral angles. Also, the greater hydrophobic character of phenanthridine compared to pyridine may facilitate its entry into cancer cells. In some cases, an increased dihedral angle between of an N-heterocycle ligand may help stabilize the platinum-DNA adduct in the Pol II active site (e.g., see Proc. Natl. Acad. Sci., USA 2010, 107, 9584-9589).

In addition, those of ordinary skill in the art would expect that a compound having a positive charge (e.g., a compound of formula (VII)) would pass into a cell at a much slower rate and/or at a lower concentration as compare to a neutral compound (e.g., cisplatin). However, the compounds described herein having a positive charge (e.g., a compound of formula (VII)) are transported much more effectively into cells as compared to some neutral compounds (e.g., cisplatin; see Example 1).

As noted, in some embodiments, the compounds as described herein have substantially high cytotoxicities. In some cases, the $IC_{50}$ for a compound of the present invention is less than about 2 uM (micromolar), less than about 1.5 uM, less than about 1.0 uM, less than about 0.9 uM, less than about 0.8 uM, less than about 0.7 uM, less than about 0.6 uM, less than about 0.5 uM, less than about 0.4 uM, less than about 0.3 uM, less than about 0.2 uM, less than about 0.1 uM, or less.

In some embodiments, the compounds of the present invention substantially affect cancer cells and have no substantial effect on non-cancerous cells (e.g., the agent is substantially inactive towards non-cancerous cells) by determining the ratio of cancer cells which are affected (e.g., resulting in cell death by the agent) to non-cancerous cells which are affected, following exposure to the therapeutically active agent. For example, the ratio of cancer cells to non-cancerous cells which are affected (e.g., cell death) upon exposure to a therapeutically active agent is at least about 10:1, at least about 100:1, at least about 500:1, at least about 1000:1, at least about 5000:1, at least about 10,000:1, at least about 100,000:1, or greater. Those of ordinary skill in the art would be aware of methods and technologies for determining the ratio of cancerous cells to non-cancerous cells affected by the agent, as well as the number of cells that undergo cell death upon exposure to the agent. Other parameters may also be determined when determining whether an agent affects a cancer cell and/or a non-cancerous cell, for example, tumor size, membrane potential of a cell, or presence or absence of a compound in parts of the cell (e.g., cytochrome c, apoptosis inducing factor, etc.).

In some embodiments, the compounds of the present invention may be used to prevent the growth of a tumor or cancer, and/or to prevent the metastasis of a tumor or cancer. In some embodiments, compositions of the invention may be used to shrink or destroy a cancer. It should be appreciated that compositions of the invention may be used alone or in combination with one or more additional anti-cancer agents or treatments (e.g., chemotherapeutic agents, targeted therapeutic agents, pseudo-targeted therapeutic agents, hormones, radiation, surgery, etc., or any combination of two or more thereof). In some embodiments, a composition of the invention may be administered to a patient who has undergone a treatment involving surgery, radiation, and/or chemotherapy. In certain embodiments, a composition of the invention may be administered chronically to prevent, or reduce the risk of, a cancer recurrence.

The cancers treatable by methods of the present invention preferably occur in mammals. Mammals include, for example, humans and other primates, as well as pet or companion animals, such as dogs and cats, laboratory animals, such as rats, mice and rabbits, and farm animals, such as horses, pigs, sheep, and cattle. In some embodiments, the compounds of the present invention may be used to treat or affect cancers including, but not limited to lymphatic metastases, squamous cell carcinoma, particularly of the head and neck, esophageal squamous cell carcinoma, oral carcinoma, blood cell malignancies, including multiple myeloma, leukemias, including acute lymphocytic leukemia, acute non-lymphocytic leukemia, chronic lymphocytic leukemia, chronic myelocytic leukemia, and hairy cell leukemia, effusion lymphomas (body cavity based lymphomas), thymic lymphoma lung cancer, including small cell carcinoma, cutaneous T cell lymphoma, Hodgkin's lymphoma, non-Hodgkin's lymphoma, cancer of the adrenal cortex, ACTH-producing tumors, nonsmall cell cancers, breast cancer, including small cell carcinoma and ductal carcinoma, gastrointestinal cancers, including stomach cancer, colon cancer, colorectal cancer, polyps associated with colorectal neoplasia, pancreatic cancer, liver cancer, urological cancers, including bladder cancer, including primary superficial bladder tumors, invasive transitional cell carcinoma of the bladder, and muscle-invasive bladder cancer, prostate cancer, malignancies of the female genital tract, including ovarian carcinoma, primary peritoneal epithelial neoplasms, cervical carcinoma, uterine endometrial cancers, vaginal cancer, cancer of the vulva, uterine cancer and solid tumors in the ovarian follicle, malignancies of the male genital tract, including testicular cancer and penile cancer, kidney cancer, including renal cell carcinoma, brain cancer, including intrinsic brain tumors, neuroblastoma, astrocytic brain tumors, gliomas, metastatic tumor cell invasion in the central nervous system, bone cancers, including osteomas and osteosarcomas, skin cancers, including malignant melanoma, tumor progression of human skin keratinocytes, squamous cell cancer, thyroid cancer, retinoblastoma, neuroblastoma, peritoneal effusion, malignant pleural effusion, mesothelioma, gall bladder cancer, trophoblastic neoplasms, and hemangiopericytoma. In some cases, the cancer is lung, ovarian, cervix, breast, bone, colorectal, and/or prostate cancer. In some cases, the cancer is lung cancer. In some cases, the cancer is human lung carcinoma and/or normal lung fibroblast.

The invention further comprises compositions (including pharmaceutical compositions), preparations, formulations, kits, and the like, comprising any of the compounds as described herein. In some cases, a pharmaceutical composition is provided comprising a composition as described herein, or a pharmaceutically acceptable salt thereof, and one or more pharmaceutically acceptable carriers, additives and/or diluents. In some cases, a kit (e.g., for the treatment of cancer) comprises a composition (or a pharmaceutical composition) as described herein and instructions for use of the composition (or a pharmaceutical composition) for treatment of cancer. These and other embodiments of the invention may also involve promotion of the treatment of cancer or tumor according to any of the techniques and compositions and combinations of compositions described herein.

In some embodiments, a platinum compound or composition described herein may be contained with a particle. In some embodiments, a particle is provided comprising a polymeric material and a platinum compound or composition as described herein. In some embodiments, a particle is provided comprising a polymeric material and a platinum compound or composition as described herein encapsulated or dispersed in the polymeric material, wherein the composition is not associated with the polymeric material via a covalent bond. In other embodiments, a particle is providing comprising a polymeric material and a platinum compound or composition as described herein encapsulated or dispersed in the polymeric material, wherein the composition is associated with the polymeric material via at least one covalent bond. In some cases, a composition is provided comprising a plurality of particles.

In some cases, a particle may be a nanoparticle, i.e., the particle has a characteristic dimension of less than about 1 micrometer, where the characteristic dimension of a particle is the diameter of a perfect sphere having the same volume as the particle. A plurality of particles, in some embodiments, may be characterized by an average diameter (e.g., the average diameter for the plurality of particles). In some embodiments, a diameter of the particles may have a Gaussian-type distribution. In some cases, the plurality of particles may have an average diameter of less than about 300 nm, less than about 250 nm, less than about 200 nm, less than about 150 nm, less than about 100 nm, less than about 50 nm, less than about 30 nm, less than about 10 nm, less than about 3 nm, or less than about 1 nm in some cases. In some embodiments, the particles may have an average diameter of at least about 5 nm, at least about 10 nm, at least about 30 nm, at least about 50 nm, at least about 100 nm, at least about 150 nm, or greater. In some cases, the plurality of the particles have an average diameter of about 10 nm, about 25 nm, about 50 nm, about 100 nm, about 150 nm, about 200 nm, about 250 nm, about 300 nm, about 500 nm, or the like. In some cases, the plurality of particles have an average diameter between about 10 nm and about 500 nm, between about 50 nm and about 400 nm, between about 100 nm and about 300 nm, between about 150 nm and about 250 nm, between about 175 nm and about 225 nm, or the like. The particle may be of any suitable size or shape. Non-limiting examples of suitable shapes include spheres, cubes, ellipsoids, tubes, sheets, and the like. Generally, the particle is spherical.

Without wishing to be bound by theory, the size of a particle may alter the delivery (e.g., loss of payload, drug efflux, aggregations, delivery to desired location, etc.) of a platinum compound from the particles. In some cases, larger particles may lose their payload more quickly than smaller particles and/or a compound efflux may be more rapid from smaller particles than larger particles. Smaller particles, in some cases, may be more likely to aggregate than larger particles. The size of the particle may affect the distribution of the particles throughout the body. For example, larger particles injected into a bloodstream may be more likely to be lodged in small vessels than smaller particles. In some instances, larger particles may be less likely to cross biological barriers (e.g., capillary walls) than smaller particles. The size of the particles used in a delivery system may be selected based on the application, and will be readily known to those of ordinary skill in the art. For example, particles of smaller size (e.g., <200 nm) may be selected if systematic delivery of the particles throughout a patient's bloodstream is desired. As another example, particles of larger size (e.g., >200 nm) may be selected if sequestering of the particles by a patient's reticuloendothelial system upon injection is desired (e.g., sequestering of the particles in the liver, spleen, etc.). The desired length of time of delivery may also be considered when selecting particle size. For example, smaller particles may circulate in the blood stream for longer periods of time than larger particles.

In some embodiments, a particle comprises a polymeric material (e.g., a polymer). A "polymer," as used herein, is given its ordinary meaning as used in the art, i.e., a molecular structure comprising one or more repeat units (monomers), connected by covalent bonds. The repeat units may all be identical, or in some cases, there may be more than one type of repeat unit present within the polymer. If more than one type of repeat unit is present within the polymer, then the polymer is said to be a "copolymer." It is to be understood that in any embodiment employing a polymer, the polymer being employed may be a copolymer in some cases. The repeat units forming the copolymer may be arranged in any fashion. For example, the repeat units may be arranged in a random order, in an alternating order, or as a "block" copolymer, i.e., comprising one or more regions each comprising a first repeat unit (e.g., a first block), and one or more regions each comprising a second repeat unit (e.g., a second block), etc. Block copolymers may have two (a diblock copolymer), three (a triblock copolymer), or more numbers of distinct blocks. In some cases, additional moieties may also be present in the polymer, for example targeting moieties such as those described herein.

In some cases, the polymer is biologically derived, i.e., a biopolymer. Non-limiting examples include peptides or proteins (i.e., polymers of various amino acids), or nucleic acids such as DNA or RNA.

In some embodiments, the polymer may be biocompatible, i.e., the polymer that does not typically induce an adverse response when inserted or injected into a living subject, for example, without significant inflammation and/or acute rejection of the polymer by the immune system, for instance, via a T-cell response. It will be recognized, of course, that "biocompatibility" is a relative term, and some degree of immune response is to be expected even for polymers that are highly compatible with living tissue. However, as used herein, "biocompatibility" refers to the acute rejection of material by at least a portion of the immune system, i.e., a non-biocompatible material implanted into a subject provokes an immune response in the subject that is severe enough such that the rejection of the material by the immune system cannot be adequately controlled, and often is of a degree such that the material must be removed from the subject. One simple test to determine biocompatibility is to expose a polymer to cells in vitro; biocompatible polymers are polymers that typically does not result in significant cell death at moderate concentrations, e.g., at concentrations of about 50 micrograms/$10^6$ cells. For instance, a biocompatible polymer may cause less than about 20% cell death when exposed to cells such as fibroblasts or epithelial cells, even if phagocytosed or otherwise uptaken by such cells. Non-limiting examples of biocompatible polymers that may be useful in various embodiments of the present invention include polydioxanone (PDO), polyhydroxyalkanoate, polyhydroxybutyrate, poly(glycerol sebacate), polyglycolide, polylactide, polycaprolactone, or copolymers or derivatives including these and/or other polymers.

In some embodiments, the biocompatible polymer is biodegradable, i.e., the polymer is able to degrade, chemically and/or biologically, within a physiological environment, such as within the body. For instance, the polymer may be one that hydrolyzes spontaneously upon exposure to water (e.g., within a subject), the polymer may degrade upon exposure to heat (e.g., at temperatures of about 37° C.). Degradation of a polymer may occur at varying rates, depending on the polymer or copolymer used. For example, the half-life of the polymer (the time at which 50% of the polymer is degraded into monomers and/or other nonpolymeric moieties) may be on the order of days, weeks, months, or years, depending on the polymer. The polymers may be biologically degraded, e.g., by enzymatic activity or cellular machinery, in some cases, for example, through exposure to a lysozyme (e.g., having relatively low pH). In some cases, the polymers may be broken down into monomers and/or other nonpolymeric moieties that cells can either reuse or dispose of without significant toxic effect on the cells (for example, polylactide may be hydrolyzed to form lactic acid, polyglycolide may be hydrolyzed to form glycolic acid, etc.). Examples of biodegradable polymers include, but are not limited to, poly(lactide) (or poly(lactic acid)), poly(glycolide) (or poly(glycolic acid)), poly(orthoesters), poly(caprolactones), polylysine, poly(ethylene imine), poly(acrylic acid), poly(urethanes), poly(anhydrides), poly(esters), poly(trimethylene carbonate), poly(ethyleneimine), poly(acrylic acid), poly(urethane), poly(beta amino esters) or the like, and copolymers or derivatives of these and/or other polymers, for example, poly(lactide-co-glycolide) (PLGA).

In some embodiments, the polymer may be a polymer which has been approved for use in humans by the U.S. Food and Drug Administration (FDA) under 21 C.F.R. §177.2600, including but not limited to polyesters (e.g., polylactic acid, poly(lactic-co-glycolic acid), polycaprolactone, polyvalerolactone, poly(1,3-dioxan-2one)); polyanhydrides (e.g., poly (sebacic anhydride)); polyethers (e.g., polyethylene glycol); polyurethanes; polymethacrylates; polyacrylates; and polycyanoacrylates. In some embodiments, the polymer may be PEGylated, as described herein.

In some embodiments, the polymer may be a polyester, including copolymers comprising lactic acid and glycolic acid units, such as poly(lactic acid-co-glycolic acid) and poly (lactide-co-glycolide), collectively referred to herein as "PLGA"; and homopolymers comprising glycolic acid units, referred to herein as "PGA," and lactic acid units, such as poly-L-lactic acid, poly-D-lactic acid, poly-D,L-lactic acid, poly-L-lactide, poly-D-lactide, and poly-D,L-lactide, collectively referred to herein as "PLA." In some embodiments, exemplary polyesters include, for example, polyhydroxyacids; PEG copolymers and copolymers of lactide and glycolide (e.g., PLA-PEG copolymers, PGA-PEG copolymers, PLGA-PEG copolymers, and derivatives thereof. In some embodiments, polyesters include, for example, polyanhydrides, poly (ortho ester), poly(ortho ester)-PEG copolymers, poly (caprolactone), poly(caprolactone)-PEG copolymers, poly (L-lactide-co-L-lysine), poly(serine ester), poly(4-hydroxy-L-proline ester), poly[α-(4-aminobutyl)-L-glycolic acid], and derivatives thereof.

In some embodiments, a polymer may be able to control immunogenicity, for example a poly(alkylene glycol) (also known as poly(alkylene oxide)), such as poly(propylene glycol), or poly(ethylene oxide), also known as poly(ethylene glycol) ("PEG"), having the formula —$(CH_2—CH_2—O)_n$—, where $n$ is any positive integer. The poly(ethylene glycol) units may be present within the polymeric base component in any suitable form. For instance, the polymeric base component may be a block copolymer where one of the blocks is poly(ethylene glycol). A polymer comprising poly(ethylene glycol) repeat units is also referred to as a "PEGylated" polymer. Such polymers can control inflammation and/or immunogenicity (i.e., the ability to provoke an immune response), due to the presence of the poly(ethylene glycol) groups. PEGylation may also be used, in some cases, to decrease charge interaction between a polymer and a biological moiety, e.g., by creating a hydrophilic layer on the surface of the polymer, which may shield the polymer from interacting with the biological moiety. Those of ordinary skill in the art will know of methods and techniques for PEGylating a polymer, for example, by using EDC (1-ethyl-3-(3-dimethylaminopropyl) carbodiimide hydrochloride) and NHS(N-hydroxysuccinimide) to react a polymer to a PEG group terminating in an amine, for example, by ring opening polymerization techniques (ROMP), or the like. In addition, certain embodiments of the invention are directed towards copolymers containing poly(ester-ether)s, e.g., polymers having repeat units joined by ester bonds (e.g., R—C(O)—O—R' bonds) and ether bonds (e.g., R—O—R' bonds).

In some embodiments, a particle may comprise at least one targeting moiety. A targeting moiety, as used herein, is a moiety able to bind to or otherwise associate with a biological moiety, for example, a membrane component, a cell surface receptor, prostate specific membrane antigen, or the like. Therefore, the targeting moiety may aid in the association and/or binding of a particle with a specific site of a patient (e.g., a certain cell type, receptor, etc.). As a non-limiting example, the targeting entity may comprise prostate specific membrane antigen which may direct the particles to prostate cells. The term "binding," as used herein, refers to the interaction between a corresponding pair of molecules or portions thereof that exhibit mutual affinity or binding capacity, typically due to specific or non-specific binding or interaction, including, but not limited to, biochemical, physiological, and/or chemical interactions. "Biological binding" defines a type of interaction that occurs between pairs of molecules including proteins, nucleic acids, glycoproteins, carbohydrates, hormones, or the like. The term "binding partner" refers to a molecule that can undergo binding with a particular molecule. "Specific binding" refers to molecules, such as polynucleotides, that are able to bind to or recognize a binding partner (or a limited number of binding partners) to a substantially higher degree than to other, similar biological entities. In one set of embodiments, the targeting moiety has a specificity (as measured via a disassociation constant) of less than about 1 micromolar, at least about 10 micromolar, or at least about 100 micromolar.

Those of ordinary skill in the art are well aware of a wide variety of targeting moieties that can direct carrier materials such as nanoparticles to specific desired locations of a subject. An extensive body of literature exists on this subject and need not be repeated here for those of ordinary skill in the art to easily understand and widely practice aspects of the invention involving targeting. Non-limiting examples of biological moieties which may be employed as targeting moieties include a peptide, a protein, an enzyme, a nucleic acid, a fatty acid, a hormone, an antibody, a carbohydrate, a peptidoglycan, a glycopeptide, or the like.

In some embodiments, the platinum compound or composition may be encapsulated or dispersed within a polymeric material, wherein the platinum compound is not associated with the polymeric material via any covalent bonds. Non-limiting examples of techniques which may be used to form particles having a platinum compound encapsulated or dispersed therein include, but are not limited to, spray drying, single and double emulsion techniques, solvent extraction, phase separation, nanoprecipitation, and other methods well known to those of ordinary skill in the art.

In some embodiments, particles comprising the platinum compound encapsulated and/or dispersed therein (e.g., wherein the platinum compound is not associated with the polymeric material via any covalent bonds) may be formed using emulsion precipitation methods or techniques. Emulsion chemistry and precipitation techniques will be known to those of ordinary skill in the art. The term "emulsion," as used herein, is given its ordinary meaning in the art and refers to a stable mixture of at least two immiscible liquids. In general, immiscible liquids tend to separate into two distinct phases. An emulsion can be stabilized by the addition of a surfactant which functions to reduce surface tension between the at least two immiscible liquids. In certain embodiments, the continuous phase is an aqueous phase, e.g., comprising water, a solution or a suspension containing water, or another fluid that is miscible in water, at least at ambient temperature (25° C.) and pressure (100 kPa). The discontinuous phase contained within the continuous phase may comprise a lipid, or other species that is not miscible in water at ambient temperature and pressure, as discussed below. In some embodiments, an emulsion comprises an aqueous phase and a lipid or oil phase, where one of these phase constitutes the droplets and the other phase constitutes the continuous phase containing the droplets, i.e., the continuous phase may be the aqueous phase or the oil phase, and the discontinuous phase may be the other phase. In addition, in some embodiments, additional phases are present, for example, as a double emulsion, as described in more detail herein. In some embodiments, a non-continuous phase comprises a polymeric material and the same or different non-continuous phase comprises a platinum compound or composition, and the emulsion may be exposed to conditions thereby causing the emulsion droplets to precipitate and/or solidify, thereby forming a plurality of particles comprising the polymeric material and the platinum compound or composition. In the case of a single emulsion, the non-continuous phase may comprise a platinum compound or composition and a polymer. Non-limiting methods for forming particles from an emulsion comprise solidifying the droplets by changing temperature, solubility techniques, evaporating solvent, and/or adding chemical cross-linking agents.

The platinum compound or composition may be dissolved or dispersed in any suitable phase of the emulsion. Any suitable quantity of the platinum compound or composition can be used, depending on the desired loading of the platinum compound or composition in the resulting emulsion and/or particles. The platinum compound or composition can be present in the aqueous phase in any desired weight %. For example, the platinum compound or composition can be present in the emulsion and/or resulting polymer in about 0.5%, about 1%, about 2%, about 3%, about 4%, about 5%, about 10%, about 15%, about 20%, about 30%, about 40%, about 50%, about 60%, about 70%, about 80%, or about 90% by weight, or any range therein.

The droplets of the emulsion may be of any shape or size, and may be spherical, or non-spherical in some cases. Any suitable volume of the aqueous solution or solvent can be used to form the desired emulsion droplet and/or particle size. In some cases, the plurality of droplets may have an average diameter of less than about 300 nm, less than about 250 nm, less than about 200 nm, less than about 150 nm, less than about 100 nm, less than about 50 nm, less than about 30 nm, less than about 10 nm, less than about 3 nm, or less than about 1 nm in some cases. In some embodiments, the plurality of droplets may have an average diameter of at least about 5 nm, at least about 10 nm, at least about 30 nm, at least about 50 nm, at least about 100 nm, at least about 150 nm, or greater. In some cases, the plurality of the droplets have an average diameter of about 10 nm, about 25 nm, about 50 nm, about 100 nm, about 150 nm, about 200 nm, about 250 nm, about 300 nm, about 500 nm, or the like. In some cases, the plurality of droplets have an average diameter between about 10 nm and about 500 nm, between about 50 nm and about 400 nm, between about 100 nm and about 300 nm, between about 150 nm and about 250 nm, between about 175 nm and about 225 nm, or the like. Such characteristic diameters may be determined using any suitable technique known to those of ordinary skill in the art, for example, laser light scattering, small angle neutron scattering, or electron microscopy. In some embodiments, the emulsion is a "nanoemulsion," i.e., an emulsion having an average diameter of droplets contained therein that is less than about 1 micrometer.

In some embodiments, an emulsion of the present invention comprises at least one surfactant. The term "surfactant," is given its ordinary meaning in the art and refers to a molecule that, when combined with a first component defining a first phase, and a second component defining a second phase, will facilitate assembly of separate first and second phases. Those of ordinary skill in the art will be aware of suitable surfactants for use in preparing emulsions, for examples, ionic surfactants or non-ionic surfactants. Non-limiting examples of surfactants include cetyltrimethylammonium bromide (CTAB), benzalkonium chloride, dimethyl dioctodecyl ammonium bromide (DDA), dioleoyl-3-trimethylammonium-propane (DOTAP), Sodium cholate, sodium dodecyl sulfate (SDS)/sodium lauryl sulfate (SLS), disulfosuccinate(DSS), sulphated fatty alcohols, polyvinyl alcohol (PVA), polyvinylpyrrolidone (PVP), sorbitan esters polysorbates, polyoxyethylated glycol monoethers, polyoxyethylated alkyl phenols and poloxamers.

In some embodiments, at least one phase comprises a polymer, wherein upon solidifying and/or precipitation of the emulsion, the polymer forms a particle. Non-limiting examples of polymers for forming particles are described herein. In some embodiments, the polymer comprising PLGA. In some cases, the polymer comprises PEG or is PEGylated. In a particular embodiment, the polymer employed in the emulsion techniques is PLGA-PEG-COOH comprising the structure:

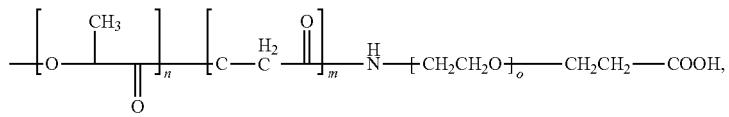

wherein n, m, and o are each independently an integer between 2 and 100,000.

Those of ordinary skill in the art will be aware of suitable aqueous solvents for use with the emulsion techniques describe herein. In some embodiments, the aqueous solvent is one that does not substantially alter the composition of the platinum compound. In some embodiments, at least one phase is an aqueous solvent. One non-limiting example of an aqueous solvent is water. In some embodiments, water can be mixed with another miscible solvent, for example, ethanol, methanol, DMSO, DMF, isopropyl alcohol, among many other water-miscible polar solvents. In some cases, the aqueous phase which comprises the platinum compound and/or which forms the continuous phase may contain other components, for example, excipients, buffers, salts, sugars, surfactants and/or viscosity-modifying agents, or combinations thereof in addition to the platinum compound.

Those of ordinary skill in the art will be aware of suitable non-aqueous solvents for use with the emulsion techniques describe herein. Generally, the non-aqueous solvent is substantially immiscible or immiscible with the aqueous phase. Non-limiting examples of non-aqueous phases include, but are not limited to, ethyl acetate, chlorinated solvents such as methylene chloride and chloroform, alkanes (e.g., pentane, hexanes, octane, etc.), or a combination thereof, among many other water immiscible organic solvents.

In some embodiments, the compounds or compositions described herein may be encapsulated in a double emulsion, followed by precipitating and/or solidifying the double emulsion. Generally, a double emulsion comprising a water-in-oil-in-water emulsion or an oil-in-water-in-oil emulsion. In some embodiments, the double emulsion is a water-in-oil-in-water emulsion. In a water-in-oil-in-water emulsion, droplets are formed comprising a first phase (e.g., generally comprising an aqueous phase having the platinum compound dissolved or dispersed therein) encapsulated or substantially encapsulated by a second phase (e.g., generally comprising a non-aqueous phase comprising a polymer) which is immiscible or substantially immiscible with the first phase, wherein the droplets are dispersed in a third phase, wherein the third phase is immiscible or substantially immiscible with the second phase (and/or third phase).

Those of ordinary skill in the art will know of suitable methods for forming a double emulsions. In some embodiments, a double emulsion may be formed by mixing a first and second phase to form a water-in-oil emulsion. The water-in-oil emulsion may comprise a first phase comprising the platinum compound and an aqueous solvent, which is substantially surrounded by the a second phase comprising a non-aqueous solvent and the polymer. The water-in-oil emulsion (i.e., the primary emulsion) may then be mixed with a third phase comprising a second aqueous solvent to form a water-in-oil-in-water double emulsion. That is, the water-in-oil-in-water emulsion comprises the first aqueous phase containing the platinum compound as the internal phase, which is substantially surrounded by the second phase containing the polymer, the second phase being substantially surrounded by the third phase. The third phase in this embodiment is typically referred to as the continuous phase. The non-continuous phase may then be precipitated and/or solidified using techniques described herein and known to those of ordinary skill in the art.

The choice of the solvent for the polymer may be selected at least in part based on the polymer solubility or polymer dispersability in that solvent. The polymer can be present in the second phase in any desired weight %. For example, the polymer can be present in the second phase in about 1% to about 90% by weight, including without limitation, about 5%, 10%, 15%, 20%, 30%, 40%, 50%, 60%, 70%, or 80% by weight. The second phase may further comprise additives, for example, cosolvents, surfactants, emulsifiers, blends of two or more polymers, or a combination thereof, among other additives.

Those of ordinary skill in the art will be aware of methods and systems for forming emulsions. For example, non-limiting techniques include sonication, controlled shearing, membrane emulsification, microfluidic techniques, etc. In a particular embodiment, an emulsion is formed using sonication. For example, a first solvent containing a platinum compound may be added to a second fluid which is immiscible or substantially immiscible with the first fluid, optionally heated and/or optionally comprising a surfactant. A variety of methods for forming single and double emulsions are described in the literature (e.g., see Radovic-Moreno et al., ACSNano, 6(5), 2012, 4279-4287; Perez et al., Journal of Controlled Release, 72, 2001, 211-224, each herein incorporated by reference).

In some embodiments, a particle may comprise a platinum compound associated with a polymeric material via formation of at least one covalent bond. For example, with respect to the compounds described herein, at least one of $R^1$-$R^6$ may form or comprise a covalent bond with the polymeric material. In some cases, at least one of $R^5$ and $R^6$ forms or comprises a covalent bond with the polymeric material. In some cases, one of $R^5$ or $R^6$ forms or comprises a covalent bond with the polymeric material.

Those of ordinary skill in the art will be aware of methods for covalently associating a platinum compound as described herein with a polymeric material. For example, in some cases, prior to covalent attached, at least one of $R^5$ or $R^6$ comprises a functional group, which is reactive with a functional group associated with the polymeric material. Accordingly, reaction of the platinum compound and the polymeric material under suitable conditions results in the formation of a covalent bond between the platinum compound and the polymeric material. Those of ordinary skill in the art will be able to determine suitable functions groups that can result in the covalent attachment of a platinum compound with a polymeric material (e.g., via condensation reactions, amide coupling reactions, pH cleavable bond reactions, click chemistry, etc.). As a specific non-limiting example, the $R^5$ group (or another ligand) of the platinum compound may comprise a —COOH functional group and the polymeric material may comprise a —CH$_2$OH functional group, or vice versa, wherein these moieties may react to form a covalent ester bond between the platinum compound and the polymer via a ester coupling reaction. As another non-limiting example, the $R^5$ group (or another ligand) of the platinum compound may comprise a —NH$_2$ group and the polymer material may comprise a —COOH, or vice versa, wherein the groups react to form an amide linkage. As yet another example, the $R^5$ group (or another ligand) of the platinum may compound comprising a —COOH group and the polymer material may comprise a —COOH group, or vice versa, wherein the groups react to form a carboxylic acid anhydride linkage. As still yet another example, the $R^5$ group (or another ligand) of the platinum compound may comprise a —N$_3$ group and the polymer material may comprise an alkyne group, or vice versa, wherein the groups react to form a triazine linkange. As still yet another example, the $R^5$ group (or another ligand) of the platinum compound may comprise a —CH$_2$OH group and the polymer material may comprise a —NCO group, wherein the groups react to form a carbamate linkage.

As will be understood by those of ordinary skill in the art, any suitable number of platinum compounds may be associated with a single polymer chain. The number of platinum compounds per polymer chain may be dependent upon the ratio of the number of platinum compounds provided per total number of polymer chains. Each polymer chain in a polymeric composition may be covalently associated with the same or a different number of platinum compounds.

Those of ordinary skill in the art will be aware of methods for forming particles comprising a polymeric material covalently associated with a platinum compound. In some embodiments, the covalent attachment between the platinum compound and the polymer material may be formed prior to forming the particles. In other embodiments, the covalent attachment between the platinum compound and the polymer material may be formed concurrently to or following formation of the particles. Non-limiting examples of methods for forming particles comprising a polymeric material include, but are not limited to nanoprecipitation and spray drying.

In some embodiments, the particles are formed via nanoprecipitation. Nanoprecipitation methods will be known to those of ordinary skill in the art (e.g., see Kolishettia et al., PNAS, 107(42), 2010, 17939-17944, herein incorporated by reference). In some cases, a nanoprecipitation method comprises adding a solution comprising a first solvent, a polymeric material, and a platinum compound (e.g., optionally associated with the polymeric material via at least one covalent bond), wherein the polymeric material is soluble or substantially soluble in the first solvent, to a second solvent in which the polymeric material is substantially insoluble. The polymeric material may precipitate upon contact with the second solvent.

In some embodiments, the solution comprising the polymeric material to be precipitated may also comprise additional components, for example, additives or other excipients. In some cases, the solution further comprises at least one additional polymeric materials (e.g., a second type of polymeric material). In some cases, the additional polymeric material is not associated with a platinum compound (e.g., via a covalent bond). The at least one second polymeric material may be selected to affect the resulting properties (e.g., size, hydrophobicity/hydrophilicity, stability, etc.) of the formed particles. In a particular embodiment, particles are formed comprising precipitating a solution comprising a first polymeric material (e.g., optionally covalently associated with a platinum compound) and a second polymeric material. In some embodiments, the ratio of the first polymeric material (e.g., optionally associated with the platinum compound via formation of at least one covalent bond) to the ratio of the second polymeric material may be about 10:1, about 9:1, about 8:1, about 7:1, about 6:1, about 5:1, about 4:1, about 3:1, about 2:1, about 1.5:1, about 1:1, about 1:1.5, about 1:2, about 1:3, about 1:4, about 1:5, about 1:6, about 1:7, about 1:8, about 1:9, or about 1:10. Suitable polymeric materials for forming particles are described herein. In some embodiments, the polymeric material associated with the platinum compound via formation of at least one bond is comprises a poly(lactic acid) polymer, or a modified form thereof. In some cases, the second polymeric material comprises PLGA, optionally PEGylated. In some cases, the platinum compound has the structure:

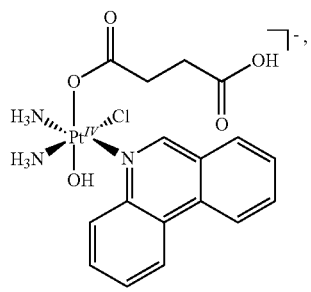

wherein the $R^5$ group comprising —OC(=O)(CH$_2$)$_2$COOH forms a covalent bond with the polymer. In some embodiments, the first polymeric material covalently associated with the platinum compound comprises the structure:

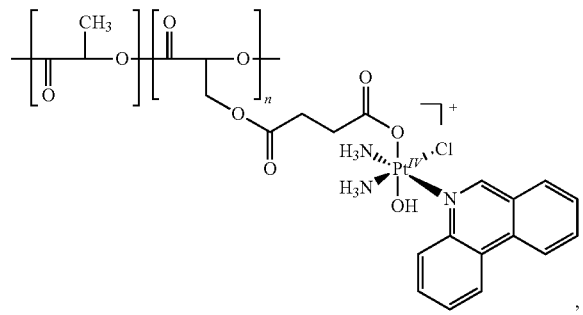

In some embodiments, the second polymeric material is PLGA-PEG-COOH comprising the structure:

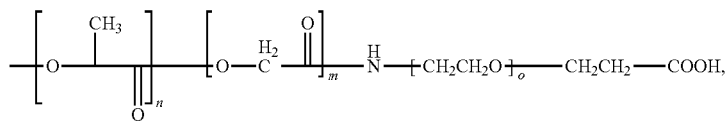

wherein n, m, and o are each independently an integer between 2 and 100,000.

Those of ordinary skill in the art will be aware of other methods and systems for forming particles containing a platinum compound, for example, as described in International Patent Application No.: PCT/US2009/005687 filed on Oct. 20, 2009, entitled NANOSTRUCTURES FOR DRUG DELIVERY by Stephen J. Lippard et al., herein incorporated by reference.

In some embodiments, the present invention provides "pharmaceutical compositions" or "pharmaceutically acceptable" compositions, which comprise a therapeutically effective amount of one or more of the compounds described herein, formulated together with one or more pharmaceutically acceptable carriers (additives) and/or diluents. The pharmaceutical compositions of the present invention may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream or foam; sublingually; ocularly; transdermally; or nasally, pulmonary and to other mucosal surfaces.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

As set out herein, certain embodiments of the present compounds may contain be formed or provided as a salt, and in some cases, as a pharmaceutically acceptable salt. The term "pharmaceutically-acceptable salt" in this respect refers to the relatively non-toxic, inorganic and organic salts of compounds of the present invention. These salts can be prepared in situ in the administration vehicle or the dosage form manufacturing process, or by separately reacting a purified compound of the invention followed by reaction with a suitable reactant (e.g., suitable organic or inorganic acid and/or base), and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al., "Pharmaceutical Salts," J. Pharm. Sci. 1977, 66, 1-19)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

The compound may be orally administered, parenterally administered, subcutaneously administered, and/or intravenously administered. In certain embodiments, a compound or pharmaceutical preparation is administered orally. In other embodiments, the compound or pharmaceutical preparation is administered intravenously. Alternative routes of administration include sublingual, intramuscular, and transdermal administrations.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient that can be combined with a carrier material to produce a single dosage form will vary depending upon the host being treated, and the particular mode of administration. The amount of active ingredient that can be combined with a carrier material to produce a single dosage form will generally be that amount of the compound which produces a therapeutic effect. Generally, this amount will range from about 1% to about 99% of active ingredient, from about 5% to about 70%, or from about 10% to about 30%.

In certain embodiments, a formulation of the present invention comprises an excipient selected from the group consisting of cyclodextrins, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary, or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol, glycerol monostearate, and non-ionic surfactants; absorbents, such as kaolin and bentonite clay; lubricants, such as talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made in a suitable machine in which a mixture of the powdered compound is moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes, and/or microspheres. They may be formulated for rapid release, e.g., freeze-dried. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams, and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Dissolving or dispersing the compound in the proper medium can make such dosage forms. Absorption enhancers can also be used to increase the flux of the compound across the skin. Either providing a rate controlling membrane or dispersing the compound in a polymer matrix or gel can control the rate of such flux.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Delivery systems suitable for use with the present invention include time-release, delayed release, sustained release, or controlled release delivery systems, as described herein. Such systems may avoid repeated administrations of the active compounds of the invention in many cases, increasing convenience to the subject and the physician. Many types of release delivery systems are available and known to those of ordinary skill in the art. They include, for example, polymer based systems such as polylactic and/or polyglycolic acid, polyanhydrides, and polycaprolactone; nonpolymer systems that are lipid-based including sterols such as cholesterol, cholesterol esters, and fatty acids or neutral fats such as mono-, di- and triglycerides; hydrogel release systems; silastic systems; peptide based systems; wax coatings; compressed tablets using conventional binders and excipients; or partially fused implants. Specific examples include, but are not limited to, erosional systems in which the composition is contained in a form within a matrix, or diffusional systems in which an active component controls the release rate. The formulation may be as, for example, microspheres, hydrogels, polymeric reservoirs, cholesterol matrices, or polymeric systems. In some embodiments, the system may allow sustained or controlled release of the active compound to occur, for example, through control of the diffusion or erosion/degradation rate of the formulation. In addition, a pump-based hardware delivery system may be used in some embodiment of the invention.

Use of a long-term release implant may be particularly suitable in some cases. "Long-term release," as used herein, means that the implant is constructed and arranged to deliver therapeutic levels of the composition for at least about 30 or about 45 days, for at least about 60 or about 90 days, or even longer in some cases. Long-term release implants are well known to those of ordinary skill in the art, and include some of the release systems described above.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

When the compounds of the present invention are administered as pharmaceuticals, to humans and animals, they can be given per se or as a pharmaceutical composition containing, for example, about 0.1% to about 99.5%, about 0.5% to about 90%, or the like, of active ingredient in combination with a pharmaceutically acceptable carrier.

The administration may be localized (i.e., to a particular region, physiological system, tissue, organ, or cell type) or systemic, depending on the condition to be treated. For example, the composition may be administered through parental injection, implantation, orally, vaginally, rectally, buccally, pulmonary, topically, nasally, transdermally, surgical administration, or any other method of administration where access to the target by the composition is achieved. Examples of parental modalities that can be used with the invention include intravenous, intradermal, subcutaneous, intracavity, intramuscular, intraperitoneal, epidural, or intrathecal. Examples of implantation modalities include any implantable or injectable drug delivery system. Oral administration may be useful for some treatments because of the convenience to the patient as well as the dosing schedule.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

The compositions of the present invention may be given in dosages, generally, at the maximum amount while avoiding or minimizing any potentially detrimental side effects. The compositions can be administered in effective amounts, alone or in a cocktail with other compounds, for example, other compounds that can be used to treat cancer. An effective amount is generally an amount sufficient to inhibit cancer within the subject.

One of skill in the art can determine what an effective amount of the composition is by screening the ability of the composition using any of the assays described herein. The effective amounts will depend, of course, on factors such as the severity of the condition being treated; individual patient parameters including age, physical condition, size, and weight; concurrent treatments; the frequency of treatment; or the mode of administration. These factors are well known to those of ordinary skill in the art and can be addressed with no more than routine experimentation. In some cases, a maximum dose be used, that is, the highest safe dose according to sound medical judgment.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required to achieve the desired therapeutic effect and then gradually increasing the dosage until the desired effect is achieved.

In some embodiments, a compound or pharmaceutical composition of the invention is provided to a subject chronically. Chronic treatments include any form of repeated administration for an extended period of time, such as repeated administrations for one or more months, between a month and a year, one or more years, or longer. In many embodiments, a chronic treatment involves administering a compound or pharmaceutical composition of the invention repeatedly over the life of the subject. For example, chronic treatments may involve regular administrations, for example one or more times a day, one or more times a week, or one or more times a month. In general, a suitable dose such as a daily dose of a compound of the invention will be that amount of the compound that is the lowest dose effective to produce a therapeutic effect. Such an effective dose will generally depend upon the factors described above. Generally doses of the compounds of this invention for a patient, when used for the indicated effects, will range from about 0.0001 to about 100 mg per kg of body weight per day. The daily dosage may range from 0.001 to 50 mg of compound per kg of body weight, or from 0.01 to about 10 mg of compound per kg of body weight. In some cases, the dose may range from between about 5 and about 50 mg of compound per kg of body weight, between about 10 and about 40 mg of compound per kg of body weight, between about 10 and about 35 mg of compound per kg of body weight, or between about 15 and about 40 mg of compound per kg of body weight. However, lower or higher doses can be used. In some embodiments, the dose administered to a subject may be modified as the physiology of the subject changes due to age, disease progression, weight, or other factors.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it may be administered as a pharmaceutical formulation (composition) as described above.

The present invention also provides any of the above-mentioned compositions useful for treatment of cancer packaged in kits, optionally including instructions for use of the composition for the treatment of cancer. That is, the kit can include a description of use of the composition for participation in any biological or chemical mechanism disclosed herein associated with cancer or tumor. The kits can further include a description of activity of cancer in treating the pathology, as opposed to the symptoms of the cancer. That is, the kit can include a description of use of the compositions as discussed herein. The kit also can include instructions for use of a combination of two or more compositions of the invention. Instructions also may be provided for administering the drug by any suitable technique, such as orally, intravenously, or via another known route of drug delivery. The invention also involves promotion of the treatment of cancer according to any of the techniques and compositions and composition combinations described herein.

The compositions of the invention, in some embodiments, may be promoted for treatment of abnormal cell proliferation, cancers, or tumors, or includes instructions for treatment of accompany cell proliferation, cancers, or tumors, as mentioned above. In another aspect, the invention provides a method involving promoting the prevention or treatment of cancer via administration of any one of the compositions of the present invention, and homologs, analogs, derivatives, enantiomers and functionally equivalent compositions thereof in which the composition is able to treat cancers. As used herein, "promoted" includes all methods of doing business including methods of education, hospital and other clinical instruction, pharmaceutical industry activity including pharmaceutical sales, and any advertising or other promotional activity including written, oral and electronic communication of any form, associated with compositions of the invention in connection with treatment of cell proliferation, cancers or tumors. "Instructions" can define a component of promotion, and typically involve written instructions on or associated with packaging of compositions of the invention. Instructions also can include any oral or electronic instructions provided in any manner. The "kit" typically defines a package including any one or a combination of the compositions of the invention and the instructions, or homologs, analogs, derivatives, enantiomers and functionally equivalent compositions thereof, but can also include the composition of the invention and instructions of any form that are provided in connection with the composition in a manner such that a clinical professional will clearly recognize that the instructions are to be associated with the specific composition.

The kits described herein may also contain one or more containers, which can contain compounds such as the species, signaling entities, biomolecules, and/or particles as described. The kits also may contain instructions for mixing, diluting, and/or administrating the compounds. The kits also can include other containers with one or more solvents, surfactants, preservatives, and/or diluents (e.g., normal saline (0.9% NaCl), or 5% dextrose) as well as containers for mixing, diluting or administering the components to the sample or to the patient in need of such treatment.

The compositions of the kit may be provided as any suitable form, for example, as liquid solutions or as dried powders. When the composition provided is a dry powder, the powder may be reconstituted by the addition of a suitable solvent, which may also be provided. In embodiments where liquid forms of the composition are sued, the liquid form may be concentrated or ready to use. The solvent will depend on the compound and the mode of use or administration. Suitable solvents for drug compositions are well known and are available in the literature. The solvent will depend on the compound and the mode of use or administration.

The kit, in one set of embodiments, may comprise a carrier means being compartmentalized to receive in close confinement one or more container means such as vials, tubes, and the like, each of the container means comprising one of the separate elements to be used in the method. For example, one of the container means may comprise a positive control in the assay. Additionally, the kit may include containers for other components, for example, buffers useful in the assay.

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

As used herein, a "subject" or a "patient" refers to any mammal (e.g., a human), such as a mammal that may be susceptible to tumorigenesis or cancer. Examples include a human, a non-human primate, a cow, a horse, a pig, a sheep, a goat, a dog, a cat, or a rodent such as a mouse, a rat, a hamster, or a guinea pig. Generally, or course, the invention is directed toward use with humans. A subject may be a subject diagnosed with cancer or otherwise known to have cancer. In certain embodiments, a subject may be selected for treatment on the basis of a known cancer in the subject. In some embodiments, a subject may be selected for treatment on the basis of a suspected cancer in the subject. In some embodiments, a cancer may be diagnosed by detecting a mutation associate in a biological sample (e.g., urine, sputum, whole blood, serum, stool, etc., or any combination thereof. Accordingly, a compound or composition of the invention may be administered to a subject based, at least in part, on the fact that a mutation is detected in at least one sample (e.g., biopsy sample or any other biological sample) obtained from the subject. In some embodiments, a cancer may not have been detected or located in the subject, but the presence of a mutation associated with a cancer in at least one biological sample may be sufficient to prescribe or administer one or more compositions of the invention to the subject. In some embodiments, the composition may be administered to prevent the development of a cancer. However, in some embodiments, the presence of an existing cancer may be suspected, but not yet identified, and a composition of the invention may be administered to prevent further growth or development of the cancer.

It should be appreciated that any suitable technique may be used to identify or detect mutation and/or over-expression associated with a cancer. For example, nucleic acid detection techniques (e.g., sequencing, hybridization, etc.) or peptide detection techniques (e.g., sequencing, antibody-based detection, etc.) may be used. In some embodiments, other techniques may be used to detect or infer the presence of a cancer (e.g., histology, etc.).

The presence of a cancer can be detected or inferred by detecting a mutation, over-expression, amplification, or any combination thereof at one or more other loci associated with a signaling pathway of a cancer.

A "sample," as used herein, is any cell, body tissue, or body fluid sample obtained from a subject. Non-limiting examples of body fluids include, for example, lymph, saliva, blood, urine, and the like. Samples of tissue and/or cells for use in the various methods described herein can be obtained through standard methods including, but not limited to, tissue biopsy, including punch biopsy and cell scraping, needle biopsy; or collection of blood or other bodily fluids by aspiration or other suitable methods.

The phrase "therapeutically effective amount" as used herein means that amount of a compound, material, or composition comprising a compound of the present invention which is effective for producing some desired therapeutic effect in a subject at a reasonable benefit/risk ratio applicable to any medical treatment. Accordingly, a therapeutically effective amount prevents, minimizes, or reverses disease progression associated with a cancer. Disease progression can be monitored by clinical observations, laboratory and imaging investigations apparent to a person skilled in the art. A therapeutically effective amount can be an amount that is effective in a single dose or an amount that is effective as part of a multi-dose therapy, for example an amount that is administered in two or more doses or an amount that is administered chronically.

In the compounds and compositions of the invention, the term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some embodiments, a straight chain or branched chain alkyl may have 30 or fewer carbon atoms in its backbone, and, in some cases, 20 or fewer. In some embodiments, a straight chain or branched chain alkyl may have 12 or fewer carbon atoms in its backbone (e.g., C1-C12 for straight chain, C3-C12 for branched chain), 6 or fewer, or 4 or fewer. Likewise, cycloalkyls may have from 3-10 carbon atoms in their ring structure, or 5, 6 or 7 carbons in the ring structure. Examples of alkyl groups include, but are not limited to, methyl, ethyl, propyl, isopropyl, cyclopropyl, butyl, isobutyl, tert-butyl, cyclobutyl, hexyl, cyclochexyl, and the like.

The term "heteroalkyl" refers to an alkyl group as described herein in which one or more carbon atoms is replaced by a heteroatom. Suitable heteroatoms include oxygen, sulfur, nitrogen, phosphorus, and the like. Examples of heteroalkyl groups include, but are not limited to, alkoxy, amino, thioester, and the like.

The terms "alkenyl" and "alkynyl" refer to unsaturated aliphatic groups analogous in length and possible substitution to the alkyls described above, but that contain at least one double or triple bond respectively.

The terms "heteroalkenyl" and "heteroalkynyl" refer to unsaturated aliphatic groups analogous in length and possible substitution to the heteroalkyls described above, but that contain at least one double or triple bond respectively.

As used herein, the term "halogen" or "halide" designates —F, —Cl, —Br, or —I.

The terms "carboxyl group," "carbonyl group," and "acyl group" are recognized in the art and can include such moieties as can be represented by the general formula:

wherein W is H, OH, O-alkyl, O-alkenyl, or a salt thereof. Where W is O-alkyl, the formula represents an "ester." Where W is OH, the formula represents a "carboxylic acid." The term "carboxylate" refers to an anionic carboxyl group. In general, where the oxygen atom of the above formula is replaced by sulfur, the formula represents a "thiolcarbonyl" group. Where W is a S-alkyl, the formula represents a "thiolester." Where W is SH, the formula represents a "thiolcarboxylic acid." On the other hand, where W is alkyl, the above formula represents a "ketone" group. Where W is hydrogen, the above formula represents an "aldehyde" group.

The term "aryl" refers to aromatic carbocyclic groups, optionally substituted, having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl). That is, at least one ring may have a conjugated pi electron system, while other, adjoining rings can be cycloalkyls, cycloalkenyls, cycloalkynyls, aryls and/or heterocyclyls. The aryl group may be optionally substituted, as described herein. "Carbocyclic aryl groups" refer to aryl groups wherein the ring atoms on the aromatic ring are carbon atoms. Carbocyclic aryl groups include monocyclic carbocyclic aryl groups and polycyclic or fused compounds (e.g., two or more adjacent ring atoms are common to two adjoining rings) such as naphthyl groups. In some cases, the The term "alkoxy" refers to the group, —O-alkyl.
The term "aryloxy" refers to the group, —O-aryl.
The term "acyloxy" refers to the group, —O-acyl.
The term "aralkyl" or "arylalkyl," as used herein, refers to an alkyl group substituted with an aryl group.

The terms "heteroaryl" refers to aryl groups comprising at least one heteroatom as a ring atom.

The term "heterocycle" refers to refer to cyclic groups containing at least one heteroatom as a ring atom, in some cases, 1 to 3 heteroatoms as ring atoms, with the remainder of the ring atoms being carbon atoms. Suitable heteroatoms include oxygen, sulfur, nitrogen, phosphorus, and the like. In some cases, the heterocycle may be 3- to 10-membered ring structures or 3- to 7-membered rings, whose ring structures include one to four heteroatoms. The term "heterocycle" may include heteroaryl groups, saturated heterocycles (e.g., cycloheteroalkyl) groups, or combinations thereof. The heterocycle may be a saturated molecule, or may comprise one or more double bonds. In some case, the heterocycle is a nitrogen heterocycle, wherein at least one ring comprises at least one nitrogen ring atom. The heterocycles may be fused to other rings to form a polycylic heterocycle. The heterocycle may also be fused to a spirocyclic group. In some cases, the heterocycle may be attached to a compound via a nitrogen or a carbon atom in the ring.

Heterocycles include, for example, thiophene, benzothiophene, thianthrene, furan, tetrahydrofuran, pyran, isobenzofuran, chromene, xanthene, phenoxathiin, pyrrole, dihydropyrrole, pyrrolidine, imidazole, pyrazole, pyrazine, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, triazole, tetrazole, oxazole, isoxazole, thiazole, isothiazole, phenanthridine, acridine, pyrimidine, phenanthroline, phenazine, phenarsazine, phenothiazine, furazan, phenoxazine, pyrrolidine, oxolane, thiolane, oxazole, oxazine, piperidine, homopiperidine (hexamethyleneimine), piperazine (e.g., N-methyl piperazine), morpholine, lactones, lactams such as azetidinones and pyrrolidinones, sultams, sultones, other saturated and/or unsaturated derivatives thereof, and the like. The heterocyclic ring can be optionally substituted at one or more positions with such substituents as described herein. In some cases, the heterocycle may be bonded to a compound via a heteroatom ring atom (e.g., nitrogen). In some cases, the heterocycle may be bonded to a compound via a carbon ring atom. In some cases, the heterocycle is pyridine, imidazole, pyrazine, pyrimidine, pyridazine, acridine, acridin-9-amine, bipyridine, naphthyridine, quinoline, benzoquinoline, benzoisoquinoline, phenanthridine-1,9-diamine, or the like.

The terms "amine" and "amino" are art-recognized and refer to both unsubstituted and substituted amines, e.g., a moiety that can be represented by the general formula: N(R')(R")(R''') wherein R', R", and R''' each independently represent a group permitted by the rules of valence. An example of a substituted amine is benzylamine. Another non-limiting example of an amine is cyclohexylamine.

Any of the above groups may be optionally substituted. As used herein, the term "substituted" is contemplated to include all permissible substituents of organic compounds, "permissible" being in the context of the chemical rules of valence known to those of ordinary skill in the art. It will be understood that "substituted" also includes that the substitution results in a stable compound, e.g., which does not spontaneously undergo transformation such as by rearrangement, cyclization, elimination, etc. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl group" must still comprise the phenyl moiety and can not be modified by substitution, in this definition, to become, e.g., a pyridine ring. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms.

Examples of substituents include, but are not limited to, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF3, —CN, aryl, aryloxy, perhaloalkoxy, aralkoxy, heteroaryl, heteroaryloxy, heteroarylalkyl, heteroaralkoxy, azido, amino, halide, alkylthio, oxo, acylalkyl, carboxy esters, carboxamido, acyloxy, aminoalkyl, alkylaminoaryl, alkylaryl, alkylaminoalkyl, alkoxyaryl, arylamino, aralkylamino, alkylsulfonyl, carboxamidoalkylaryl, carboxamidoaryl, hydroxyalkyl, haloalkyl, alkylaminoalkylcarboxy, aminocarboxamidoalkyl, cyano, alkoxyalkyl, perhaloalkyl, arylalkyloxyalkyl, and the like.

U.S. Provisional Application No. 61/499,439, filed Jun. 21, 2011, to Lippard et al., and U.S. Provisional Application No. 61/506,868, filed Jul. 12, 2011 to Lippard et al., are each herein incorporated by reference.

The following examples are intended to illustrate certain embodiments of the present invention, but do not exemplify the full scope of the invention.

Example 1

This example describes the synthesis and use of phenanthriplatin (e.g., a compound of formula (VII)).

Experimental Details

Materials and Measurements.

Pyriplatin was synthesized as previously reported (*J. Med. Chem.* 1989, 32, 128-136). All other chemicals and solvents are commercially available. $^1$H, $^{13}$C and $^{195}$Pt NMR spectra were recorded on a Bruker AVANCE-400 NMR spectrometer with a Spectro Spin superconducting magnet in the Massachusetts Institute of Technology Department of Chemistry Instrumentation Facility (MIT DCIF). Chemical shifts were referenced to $K_2PtCl_4$ in $D_2O$ ($\delta$=−1628 ppm) for $^{195}$Pt NMR or to residual solvent peaks for $^1$H and $^{13}$C NMR. ESI-MS spectra were obtained on an Agilent Technologies 1100 Series LC/MS instrument. Atomic absorption spectroscopic measurements were taken on a Perkin Elmer AAnalyst 300 spectrometer. Distilled water was purified by passage through a Millipore Milli-Q Biocel water purification system (18.2 MΩ) with a 0.22 μm filter.

X-ray Crystallographic Studies.

Single crystals were mounted in Paratone oil on a cryoloop and frozen under a 110 K or 100 K KRYO-FLEX nitrogen cold stream. Data were collected on a Bruker APEX CCD X-ray diffractometer with graphite-monochromated Mo-Kα radiation (λ=0.71073 Å) controlled by the APEX2 software package (APEX2, 2008-4.0. B. A., Inc.: Madison, Wis., 2008). Absorption corrections were applied using SADABS (Sheldrick, G. M. University of Göttingen: Göttingen, Germany, 2008). The structures were solved using direct methods and refined on $F^2$ with the SHELXTL-97 software package (Sheldrick, G. M. SHELXTL-97, 6.14 University of Göttingen: Göttingen, Germany, 2000, Sheldrick, G. M. *Acta Crystallogr. Sect. A* 2008, 64, 112-122). Structures were checked for higher symmetry using PLATON (Spek, A. L. *PLATON, A Multipurpose Crystallographic Tool* Utrecht University: Utrecht, The Netherlands, 2008). All non-hydrogen atoms were located and refined anisotropically. Unless otherwise stated, hydrogen atoms were placed in idealized locations and given isotropic thermal parameters equivalent to either 1.5 (terminal $CH_3$ or $NH_3$ hydrogen atoms) or 1.2 times the thermal parameter of the atom to which they were attached. Structure refinement was carried out using established strategies (Müller, P. *Crystallogr. Rev.* 2009, 15, 57-83). Crystallographic data for phenanthriplatin have been deposited at the Cambridge Structural Database under CSD reference no. CCDC 875229

Crystals of cis-[Pt(NH$_3$)$_2$(quinoline)Cl]NO$_3$ (quinoplatin) were also characterized structurally by X-ray crystallography. Crystallographic data for quinoplatin have deposited at the Cambridge Structural Database under CSD reference no. CCDC 875230.

Synthesis of phenanthriplatin, cis-[Pt(NH$_3$)$_2$(phenanthridine)Cl]NO$_3$ (Compound of Formula (VII)).

To a solution of cisplatin (0.30 g, 10 mmol) in 15 mL DMF was added AgNO$_3$ (0.169 g, 1 equiv) and the reaction was stirred under protection from light at 60° C. After 16 h, a AgCl precipitate was filtered. To the supernatant, phenanthridine (0.161 g, 0.9 equiv) was added, and the reaction was stirred for 16 h at 60 60° C. The reaction mixture was evaporated under reduced pressure, and the residue was dissolved in 30 mL of MeOH. Unreacted yellow cisplatin was removed by filtration. The filtrate was stirred vigorously and diethylether (100 mL) was then added to precipitate the desired compound as a solid. The diethylether and methanol were decanted and washed 2 times with 50 mL of diethylether. The compound was purified by redissolving it in methanol and precipitating it by adding the methanol solution dropwise to vigorously stirred diethyl ether. The final compound was isolated by vacuum filtration and dried in vacuo. X-ray quality crystals were obtained from methanol/diethylether. White solid. Yield: 59.4% (0.30 g). ESI-MS m/z calculated ($M^+$): 443.06. found: 443.1. $^1$H NMR (DMSO-$d_6$): δ 4.43 (3H, broad), 4.60 (3H, broad), 7.93 (2H, q), 8.02 (1H, t), 8.14 (1H, t), 8.46 (1H, d), 8.93 (2H, q), 9.78 (1H, d), 9.95 (1H, s). $^{13}$C NMR (DMSO-$d_6$): δ 122.53, 123.27, 125.23, 126.20, 129.02, 129.36, 130.17, 131.72, 134.24, 142.39, 160.14. $^{195}$Pt NMR (DMSO-$d_6$): δ −2298.51. Anal. Calcd. for $C13H_{15}ClN_4O_3Pt$: C, 30.87; H, 2.99; N, 11.08. Found: C, 31.08; H, 3.02; N, 11.03.

Cell Lines and Cell Culture.

Human colon carcinoma HT29, human breast carcinoma MCF7, human bone sarcoma U2OS, human prostate carcinoma PC3, and human cervix carcinoma HeLa cells were obtained from the ATCC. A2780/CP70 cisplatin-resistant human ovarian cancer cells were kindly provided by Dr. Stephen B. Howell (Moores UCSD Cancer Center) and the human lung carcinoma cell lines A549 and normal lung fibroblast MRC5 by David E. Root (Whitehead Institute for Biomedical Research). Cells were incubated at 37° C. in 5% $CO_2$ and grown in RPMI (HT29, A2780/CP70, and PC3) or DMEM (A549, MRC5, HeLa, MCF7, and U2OS) medium supplemented with 10% fetal bovine serum and 1% penicillin/streptomycin. Cells were passed every 3 to 4 days and restarted from a frozen stock upon reaching pass number 20.

MTT Assay.

The cytotoxic behavior of cisplatin, oxaliplatin, pyriplatin, and phenanthriplatin was evaluated using the MTT assay. Solutions of the platinum compounds were freshly prepared in sterile PBS before use and their concentrations quantitated by atomic absorption spectroscopy. Cells were seeded on a 96-well plate (1200 cells per well for cancer cells and 1800 cells per well for the normal lung fibroblasts) in 100 μL RPMI or DMEM media, and incubated for 24 h. The cells were then treated with cisplatin, oxaliplatin, pyriplatin, or phenanthriplatin, separately at varying concentrations, and incubated for 72 h at 37° C. The cells were then treated with 20 μL of 3-(4,5-dimethylthiazol-2-yl)-2,5-diphenyltetrazolium bromide (MTT) (5 mg/mL in PBS) and incubated for 4 h. The medium was removed, 100 μL of DMSO was added to the cells, and the absorbance of the purple formazan was recorded at 560 nm using a BioTek Synergy HT multi-detection microplate plate reader. Each condition was performed in triplicate and three independent experiments were carried out for each cell line.

Cellular Uptake of Platinum.

The cellular accumulation of platinum was determined as previous described (*Dalton Trans.*, 2010, 39, 11353-11364 and *Proc Natl Acad Sci USA*, 2009, 106, 22199-22204) with some modifications. The cells (~$10^6$ cells) were seeded in a 60 mm diameter Petri dish in triplicate in the culture medium and left overnight to attach. For platinum accumulation, the cells were treated with 5 μM of cisplatin, pyriplatin, or phenanthriplatin at 37° C. in 5% $CO_2$ for 3 h. After incubation, the medium was removed and cells were washed with 2 mL of ice-cold PBS three times to remove excess Pt compounds. The cells were collected using 1 mL trypsine for the harvest and 0.5 mL PBS. The cell pellets were obtained by centrifugation at 200×g and at 4° C. for 20 min. The cell pellets obtained were resuspended in 200 μL of ice-cold lysis buffer (1.0 mM DTT, 1.0 mM PMSF, 10 mM KCl, and 10 mM $MgCl_2$, pH 7.5) and cooled for 15 min in an ice bath. The cells were centrifuged at 450×g at 4° C. for 20 After removing supernatant, finally the pellets were resuspended in 150 μL of ice-cold lysis buffer for cytoplasm and nuclei fraction extraction. The cell membranes were lysed using 10 strokes of a 28-gauge syringe. The resultant suspension was centrifuged at 11,000×g for 20 min at 4° C., and the supernatant was retained as the cytosolic fraction. The nuclear pellet was resuspended in 150 μL of extraction buffer (1.0 mM DTT, 1.0 mM PMSF, 1.5 mM $MgCl_2$, 0.2 M EDTA, 0.42 M NaCl, and 25% glycerol, pH 7.9) and lysed by 10 strokes of a 28-gauge syringe. The lysate was shaken at 1,000 rpm for 1 h at 4° C. and centrifuged at 20,000×g for 10 min at 4° C. The nuclear fraction was collected as supernatant. To evaluate whole cell uptake, 150 μL of concentrated nitric acid was added to washed cell pellets, and cells were digested for 2 h at 90° C. Platinum concentrations in all of the fractions were determined by AAS.

Preparation of Globally Platinated Plasmids.

pGLuc plasmid was obtained using commercially available pCMV-GLuc vector as previously reported (*J. Am. Chem. Soc.* 2010, 132, 7429-7435). A 125 μg/mL (46 nM) portion of pGLuc plasmid dissolved in 24 mM Na-HEPES pH 7.4 and 10 mM NaCl buffer was treated with cisplatin (0, 2.95, 5.73, 11.35, 22.43 μM), pyriplatin (0, 6.53, 15.98, 30.49, 59.32 μM), or phenanthriplatin (0, 3.18, 7.56, 11.78, 23.82 μM) for 16 h at 37° C. The resulting mixtures were dialyzed (molecular weight cut-off 3.5 kDa) against $ddH_2O$ overnight at 4° C. with five changes of $ddH_2O$. The $r_b$ values (bound Pt/nucleotide) were determined by UV/Vis and atomic absorption spectroscopy.

Transient Transfection of Cells for Transcription Assays.

Transfection of transcription probes into A549 and HT29 cells with the pGLuc plasmid was carried out using liposomal transfecting agents. Determination of expression levels was tested by Luciferase assays monitored by a luminometer (*J. Am. Chem. Soc.* 2010, 132, 7429-7435). A549 cells were plated in 96-well plates at 2,000 cells/well and HT29 cells were plated in 96-well plates at 6,000 cells/well. After 48 h incubation (at ~30% confluence), cells were transfected with 50 ng of platinated plasmids in 25 μL Opti-MEM and 0.125 μL Lipofectamine 2000, and subsequently 50 μL of antibiotics-free DMEM supplemented with 10% FBS. After 2 h, the cells were washed with medium and 100 μL of fresh medium was added. The experiment was carried out in quadruplicate.

GLuc Luminometry Assay.

GLuc activity was monitored using a luminescence plate reader (Synergy 2, BioTek, Winooski, Vt., USA). A 10 μL volume of medium at different time points (12, 24, 36, 48, 60 h) was transferred into opaque white 96-well plates, and 25 μL of GLuc assay solution (10 μM colelenterazine (NanoLight Technologies, Pinetop, Ariz., USA) in 2.5 mM acidified methanol (100 mM HCl), buffer (10 mM Tris-HCl pH 7.8, 1 mM EDTA, 0.6 M NaCl)) was added by the automatic injector of the instrument.

Kinetic Studies.

NMR spectra were collected on a Varian 500 spectrometer equipped with a triple-resonance broadband inverse probe and a variable temperature unit. The 1-D $^1$H NMR kinetic studies were performed in duplicate as a standard time-arrayed experiment using a variable delayed list. Incremented 1-D spectra were processed in exactly the same way and signals of aromatic amine ligands from platinum compounds were integrated. The relative concentrations of the platinum compound at each time point were calculated from peak integrals. The aquation of pyriplatin and phenanthriplatin was investigated at 37° C. by NMR spectroscopy in $D_2O$ solutions containing 2 mM of the Pt compound with dioxane as an internal standard. Reactions of platinum compounds with N-AcMet were performed in NMR tubes containing 2 mM of the Pt complex and 2 mM (1 equiv) of N-AcMet in 10 mM PBS buffer, $D_2O$, pH*7.4 at 37° C. Reactions of platinum compounds with 5'-dGMP were performed in NMR tubes containing 2 mM of the platinum compounds and 32 mM (16 equiv) of 5'-dGMP in 10 mM PBS buffer, $D_2O$, pH*7.4 at 37° C. Deuterated 3-(trimethylsilyl)propionic acid sodium salt (TMS-PFASS) was used as an internal standard. The pH* values are the measured pH values without correction for the effect of deuterium on the electrode.

Results

Synthesis and Characterization of Phenanthriplatin.

The formation of phenanthriplatin was confirmed by $^{1}H$, $^{13}C$, and $^{195}Pt$ NMR spectroscopy, ESI-MS, and X-ray crystallography.

Crystals of phenanthriplatin were obtained from methanol/diethylether and were used to determine the molecular structure of phenanthriplatin (see FIG. 1 and Table 1 and 2) and quinoplatin by X-ray diffraction.

The plane of the aromatic heterocyclic ligand in both structures is approximately perpendicular to that of the platinum coordination plane. In this orientation, the quinoline and phenanthridine ligands may provide steric protection against axial attack by an entering nucleophile perpendicular to the platinum coordination plane. Since the most efficacious ligand substitution reactions at platinum(II) centers occur by an associative mechanism at the axial positions, this steric protection may diminish the ligand substitution reaction rates of quinoplatin and phenanthriplatin compared to that of pyriplatin. This principle has been adopted for the related platinum anti-cancer complex cis-[Pt(NH$_3$)(2-picoline)Cl$_2$] (picoplatin), which is currently undergoing clinical trials. The reactions of picoplatin with water and other nucleophiles are much slower than those of cisplatin and related complexes lacking steric hindrance at the axial sites. The lesser reactivity of picoplatin, particularly with thiols like glutathione, prevents undesired deactivation of the complex before it can reach DNA. The steric protection afforded by the quinoline and phenanthridine ligands of quinoplatin and phenanthriplatin, respectively, is comparable to that offered by picoplatin. The distances between the platinum atom and the overhanging carbon atoms of quinoplatin and phenanthriplatin (3.210 and 3.220 Å, respectively) are nearly identical to that of picoplatin (3.224 Å) (12). These results indicate that quinoplatin and phenanthriplatin may exhibit decreased reactivity with biological nucleophiles, a property that may be important in preventing their premature deactivation. Reaction with the nucleobases, which are planar and not as sterically encumbers, may still occur, however. Lastly, the large steric bulk of the phenanthridine and quinoline ligands revealed by these crystal structures may impede progression of pol II more effectively than the smaller pyridine ring of pyriplatin.

TABLE 1

Crystal data and structure refinement for phenanthriplatin.

| | |
|---|---|
| Empirical formula | $C_{13}H_{15}ClN_4O_3Pt$ |
| Formula weight | 505.83 |
| Crystal system | Orthorhombic |
| Space group | Pbca |
| Unit cell dimensions | a = 11.946(2) Å |
| | b = 10.3474(18) Å |
| | c = 24.754(4) Å |
| Volume | 3059.7(9) Å$^3$ |
| Z | 8 |
| Density (calculated) | 2.196 Mg/m$^3$ |
| Absorption coefficient | 9.364 mm$^{-1}$ |
| F(000) | 1920 |
| Crystal size | 0.20 × 0.06 × 0.03 mm$^3$ |
| Theta range for data collection | 1.65 to 25.13°. |
| Index ranges | $-14 <= h <= 14, -11 <= k <= 12,$ |
| | $-29 <= l <= 29$ |
| Reflections collected | 43571 |
| Independent reflections | 2724 [R(int) = 0.0620] |
| Completeness to theta = 25.13° | 99.8% |
| Absorption correction | Semi-empirical from equivalents |
| Max. and min. transmission | 0.7665 and 0.2560 |
| Refinement method | Full-matrix least-squares on F$^2$ |
| Data/restraints/parameters | 2724/0/201 |
| Goodness-of-fit on F$^2$ | 1.116 |
| Final R indices [I > 2sigma(I)] | R1 = 0.0352, wR2 = 0.0856 |
| R indices (all data) | R1 = 0.0452, wR2 = 0.0918 |
| Largest diff. peak and hole | 3.524 and −1.089 e · Å$^{-3}$ |

$R1 = \Sigma ||F_o| - |F_c||/\Sigma |F_o|,$
$wR2 = \{\Sigma[w(F_o^2 - F_c^2)^2]/\Sigma[w(F_o^2)^2]\}^{1/2}.$

TABLE 2

Selected bond lengths (Å) and angles (deg) for phenanthriplatin.

| | |
|---|---|
| Pt(1)—N(3) | 2.032(6) |
| Pt(1)—N(1) | 2.036(6) |
| Pt(1)—N(2) | 2.040(6) |
| Pt(1)—Cl(1) | 2.2998(19) |
| N(3)—Pt(1)—N(1) | 176.4(2) |
| N(3)—Pt(1)—N(2) | 94.2(3) |
| N(1)—Pt(1)—N(2) | 89.4(3) |
| N(3)—Pt(1)—Cl(1) | 85.90(18) |
| N(1)—Pt(1)—Cl(1) | 90.51(19) |
| N(2)—Pt(1)—Cl(1) | 178.26(19) |

Antiproliferative Effects of Phenanthriplatin in a Panel of Human Cancer Cell Lines.

A panel of 7 human cancer cell lines of different origin was treated with cisplatin, oxaliplatin, pyriplatin, or phenanthriplatin for 72 h and then evaluated for cytotoxicity by the MTT assay. The concentrations ranged from 0~200 μM of cisplatin or oxaliplatin, 0~1,000 μM of pyriplatin, or 0~50 μM phenanthriplatin. Table 3 reports the IC$_{50}$ values in each of the 7 cell lines and standard deviations for at least three experiments, each performed in triplicate. A comparison of cytotoxicity between the four compounds is presented in FIG. 2.

Figure 2:
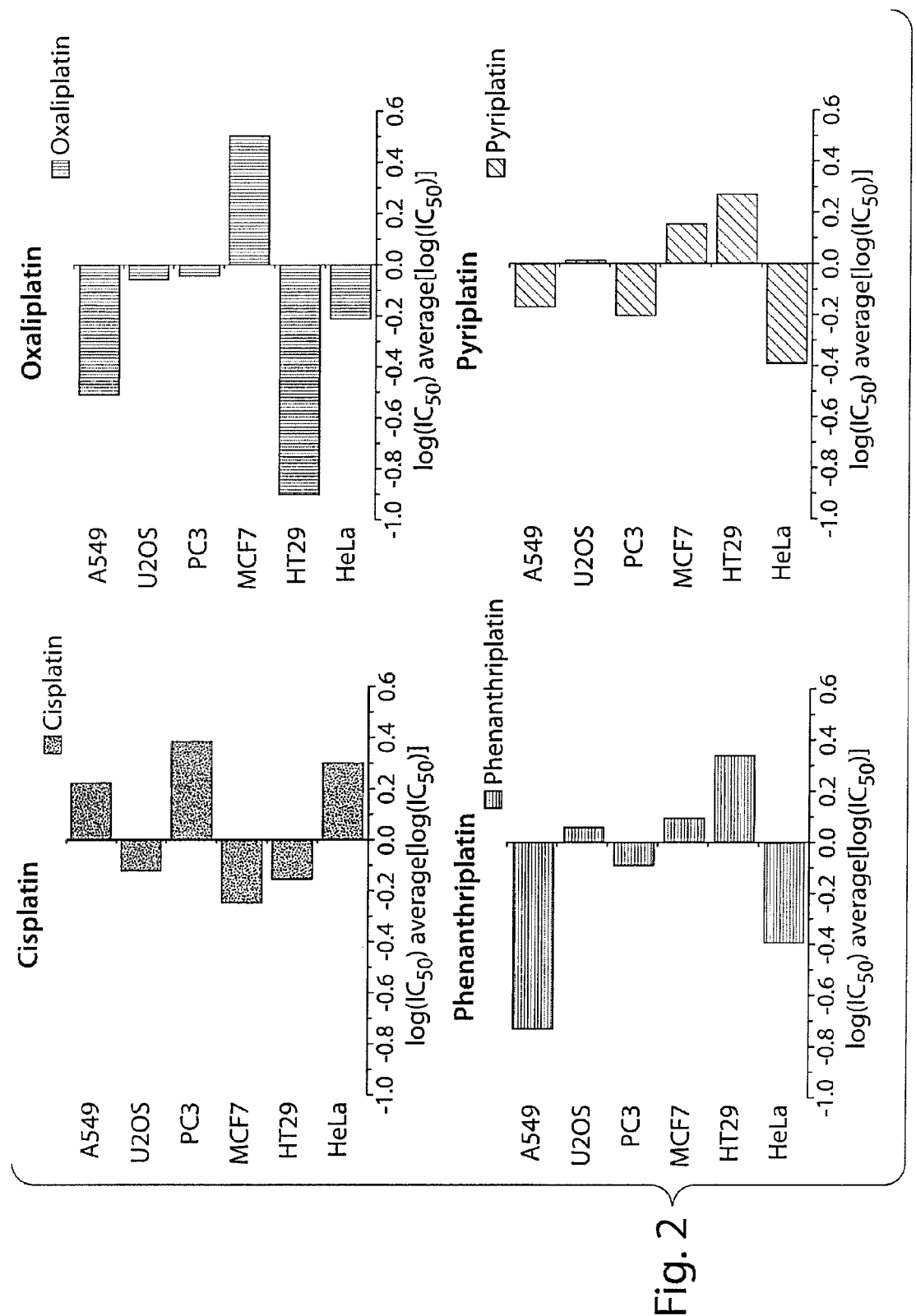
FIG. 2 shows comparative analysis of cytotoxicity of anticancer agents in a panel of human cancer cell lines, according to some embodiments.

In FIG. 2: Comparative analysis of cytotoxicity of anticancer agents in a panel of human cancer cell lines. The influence of cisplatin, oxaliplatin, pyriplatin, and phenanthriplatin on the viability of 6 different tumor cell lines was determined using the MTT assay after continuous drug exposure for 72 h. The indicated values are calculated as follows: log [(IC$_{50}$ individual cell line)-mean (logIC$_{50}$)]. Negative values indicate that the cell line is more sensitive than the average, whereas positive values indicate that the cell line is more resistant than the average. The abscissa is presented on a log scale.

TABLE 3

IC$_{50}$ values for cisplatin, oxaliplatin, pyriplatin, and phenanthriplatin in the 7-cell line panel for a 72-h incubation period. Data reflect the mean and standard deviation of results from three separate experiments, each performed in triplicate.

| | | IC$_{50}$ (μM) | | | |
|---|---|---|---|---|---|
| Cell Line | Cancer Type | cisplatin | oxaliplatin | phenanthriplatin | pyriplatin |
| A549 | Lung | 6.75 ± 0.38 | 6.79 ± 0.26 | 0.22 ± 0.01 | 52.1 ± 2.3 |
| HeLa | Cervix | 1.77 ± 0.72 | 11.8 ± 1.4 | 0.30 ± 0.02 | 31.3 ± 2.8 |
| MCF7 | Breast | 11.6 ± 0.6 | 17.9 ± 2.7 | 0.94 ± 0.09 | 109 ± 10 |
| U2OS | Bone | 7.15 ± 0.25 | 8.67 ± 0.59 | 0.59 ± 0.04 | 78.9 ± 6.7 |
| HT29 | Colorectal | 15.9 ± 1.5 | 1.81 ± 1.15 | 2.02 ± 0.04 | 144 ± 10 |
| NTera2 | Testis | 0.14 ± 0.03 | 1.12 ± 0.08 | 0.035 ± 0.002 | 5.16 ± 0.96 |
| PC3 | Prostate | 4.56 ± 0.52 | 13.2 ± 4.0 | 0.74 ± 0.04 | 47.9 ± 9.2 |

The cytotoxicity of phenanthriplatin is substantially greater (7~40 times) than that of cisplatin or oxaliplatin. Phenanthriplatin has a widely different spectrum of activity against various cells lines compared with that of either oxaliplatin or cisplatin. Pyriplatin and phenanthriplatin have similar activity profiles against these cells, although quantitatively not identical.

The NCI-60 DTP (Developmental Therapeutics Program) Human Tumor Cell Line Screen has been used to evaluate the anticancer activities of many chemical compounds and natural product samples. This test utilizes 60 different human cancer cell lines representative of leukemia, non-small cell lung, colon, central nervous system, melanoma, ovarian, renal, prostate, and breast cancers. Anticancer compounds exhibit distinctive sensitivity and resistivity profiles in these cell lines that determine their spectrum of activity, which is often indicative of its cellular mechanism of action. The COMPARE program quantitatively matches the spectrum of activity of one compound to others in the NCI database. Given the potential utility of this screen in identifying novel drug candidates, phenanthriplatin was submitted to the NCI for evaluation in 2011. Phenanthriplatin showed significant growth inhibition of the 60 cell lines at a single dose of 10 μM. Based on its success in the single dose screen, it was further tested against the 60-cell panel at five concentration levels. The detailed results and comparison with conventional bifunctional platinum-based antitumor drugs such as cisplatin and oxaliplatin are provided in FIG. 6. Analysis by the online COMPARE algorithm revealed that phenanthriplatin could not be correlated with any other platinum anticancer agent. The highest correlation in the NCI database was for doxorubicin, with a correlation coefficient of 0.607. These results demonstrate that phenanthriplatin has a unique spectrum of activity compared to conventional platinum-based and most other anticancer drugs.

Figure 6:
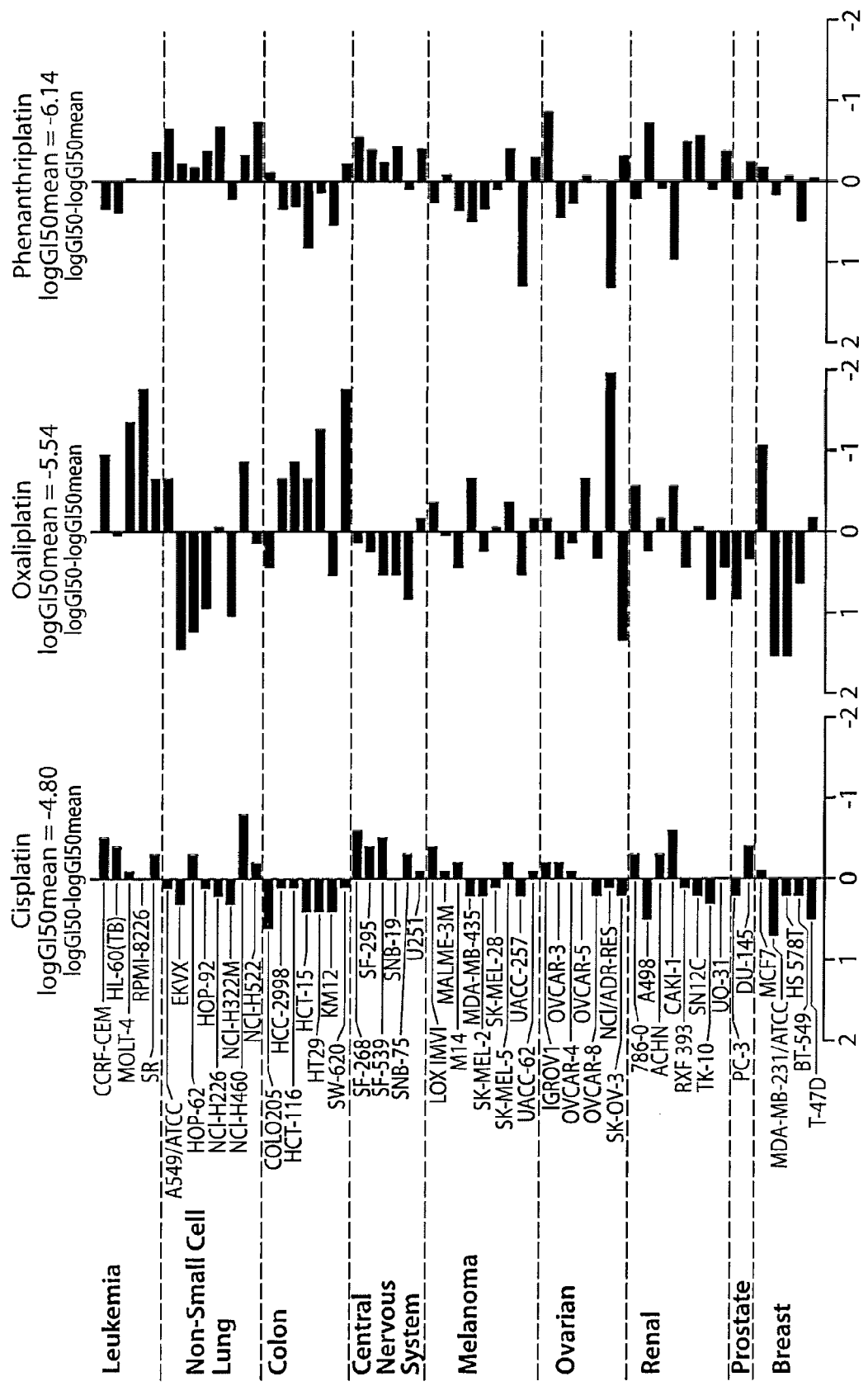
FIG. 6 shows comparative analysis of cytotoxicity of non-limiting anticancer agents in the NCI-60 tumor cell line panel, according to some embodiments.

In FIG. 6: Comparative analysis of cytotoxicity of anticancer agents in the NCI-60 tumor cell line panel. The indicated values are calculated as follows: log[(GI50 individual cell line)-mean (logGI50)]. Negative values indicate that the cell line is more sensitive than the average, whereas positive values indicate that the cell line is more resistant than the average. The abscissae are presented on a log scale. Data of cisplatin and oxaliplatin are obtained from the NCI web site.

Selective killing of cancer cells by phenanthriplatin. One objective in cancer therapy is to find an anti-cancer drug that kills cancer cells selectively over healthy cells, thereby mitigating toxic side effects normally associated with chemotherapy. Normal lung fibroblasts (MRC5) and cancerous lung (A549) cells were used to evaluate the selectivity of phenanthriplatin for cancer vs healthy cells. The A549 and MRC5 cell cultures were treated with cisplatin or phenanthriplatin for 72 h, after which cell viability was evaluated by the MTT assay (Table 5). The ratio of IC$_{50}$ values in healthy MRC5 cells to those in cancerous A549 cells was 0.9 for cisplatin compared to 3.9 for phenanthriplatin. The higher ratio obtained for phenanthriplatin reveals its selectivity for cancer cells, at least in the cellular monolayer assays used in this study.

TABLE 4

IC$_{50}$ values for cisplatin, oxaliplatin, pyriplatin, and phenanthriplatin in human lung carcinoma (A549) and normal lung fibroblast (MRC5) for a 72 h incubation period. Data reflect the mean and standard deviation of results from three separate experiments, each performed in triplicate.

| Cell Line | Cancer Type | IC$_{50}$ (μM) cisplatin | IC$_{50}$ (μM) oxaliplatin | IC$_{50}$ (μM) phenanthriplatin | IC$_{50}$ (μM) pyriplatin |
|---|---|---|---|---|---|
| A549 | human lung carcinoma | 6.62 ± 0.40 | 10.46 ± 0.18 | 0.17 ± 0.002 | 52.12 ± 2.25 |
| MRC5 | normal lung fibroblast | 6.18 ± 0.16 | None | 0.86 ± 0.06 | 92.1 ± 9.9 |

TABLE 5

IC$_{50}$ values* for cisplatin and monofunctional Pt(II) compounds in the various cell lines for a 72-h incubation period

| IC$_{50}$ (μM) | A549 | MRC5 | HT29 | HeLa | U2OS |
|---|---|---|---|---|---|
| cisplatin | 6.75 ± 0.38 | 6.18 ± 0.16 | 15.9 ± 1.5 | 1.77 ± 0.72 | 7.15 ± 0.25 |
| cis-[Pt(NH$_3$)$_2$(pyridine)Cl]NO$_3$ | 52.1 ± 2.3 | 92.1 ± 9.9 | 144 ± 10 | 31.3 ± 2.8 | 78.9 ± 6.7 |
| cis-[Pt(NH$_3$)$_2$(2-methylpyridine)Cl]NO$_3$ | 50.6 ± 1.7 | 58.9 ± 4.2 | 63.8 ± 1.9 | Not measured | Not measured |
| cis-[Pt(NH$_3$)$_2$(2-amino-3-methylpyridine)-Cl]NO$_3$ | 47.1 ± 1.4 | 51.7 ± 7.7 | 72.9 ± 4.6 | not measured | not measured |
| cis-[Pt(NH$_3$)$_2$(quinoline)Cl]NO$_3$ | 8.11 ± 0.68 | 23.5 ± 1.6 | 38.0 ± 4.5 | 12.2 ± 0.8 | 23.5 ± 2.7 |
| cis-[Pt(NH$_3$)$_2$(isoquinoline)Cl]NO$_3$ | 11.5 ± 0.4 | 26.4 ± 1.0 | 45.6 ± 2.7 | Not measured | Not measured |
| cis-[Pt(NH$_3$)$_2$(1-methylimidazole)-Cl]NO$_3$ | 62.0 ± 0.8 | 40.5 ± 1.1 | 53.4 ± 8.5 | Not measured | Not measured |
| cis-[Pt(NH$_3$)$_2$(acridine)Cl]NO$_3$ | 3.74 ± 0.01 | 9.17 ± 0.47 | 13.5 ± 0.7 | 2.69 ± 0.10 | 4.42 ± 0.31 |
| cis-[Pt(NH$_3$)$_2$(benzo[f]quinoline)Cl]NO$_3$ | 0.83 ± 0.03 | Not measured | Not measured | 0.64 ± 0.01 | 0.88 ± 0.01 |
| cis-[Pt(NH$_3$)$_2$(phenanthridine)-Cl]NO$_3$ | 0.22 ± 0.01 | 0.86 ± 0.06 | 2.02 ± 0.04 | 0.30 ± 0.02 | 0.59 ± 0.04 |

*Data reflect the mean and standard deviation of results from three separate experiments, each performed in triplicate.

Cellular Uptake of Platinum Compounds.

Figure 3:
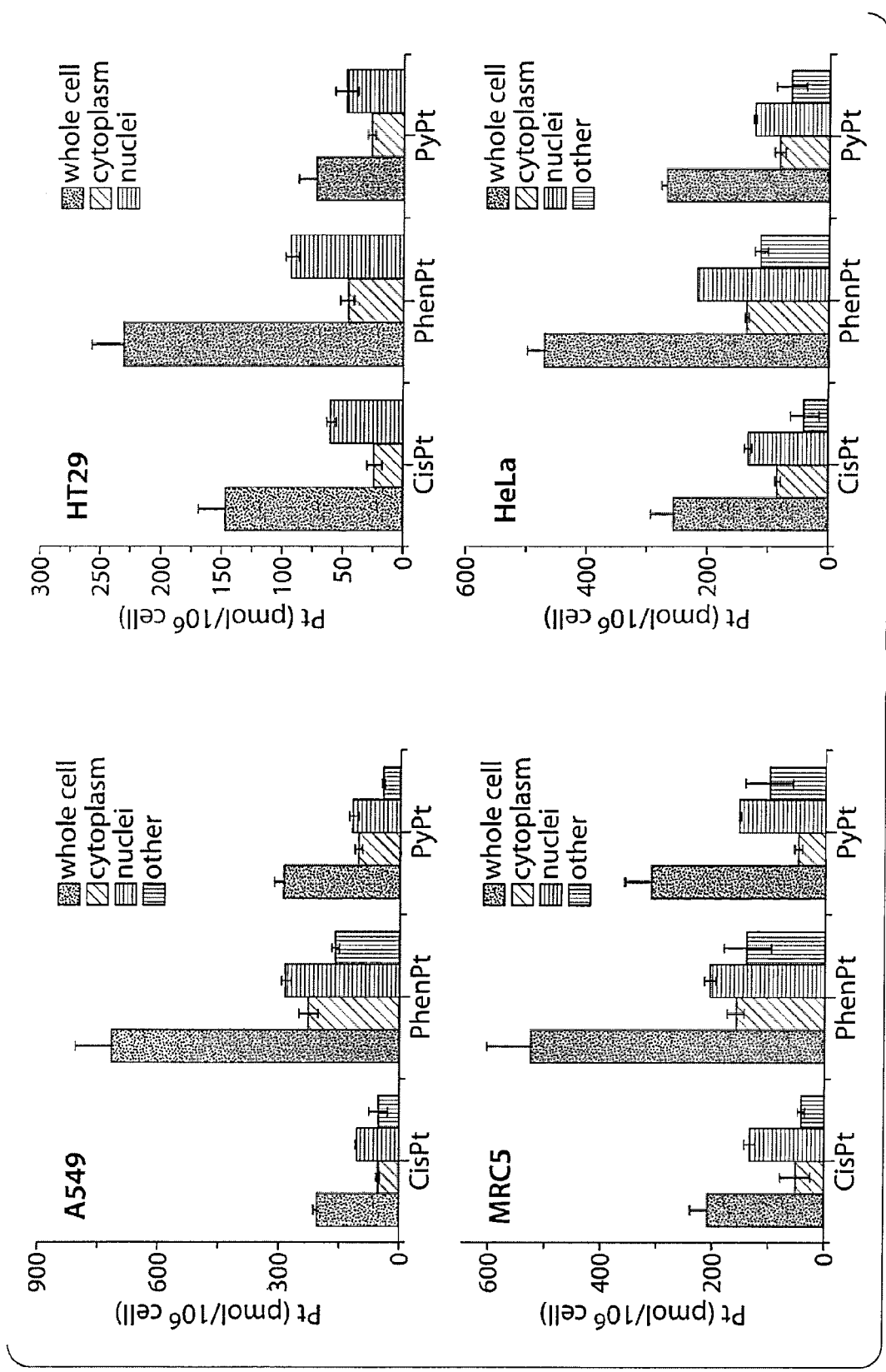
FIG. 3 shows plots of picomoles of Pt in A549, HT29, MRC5, and HeLa after 3 h of treatment with 5 μM cisplatin, pyriplatin, or phenanthriplatin, according to some embodiments.

The activity of platinum drugs against cancer is mediated by a combination of processes including cell entry, drug activation, DNA binding, and transcription inhibition. Cellular entry of Pt-based drugs is thought to occur by both passive diffusion and carrier-mediated active transport. To determine the transport of platinum compounds into the cell, the nuclear, cytosolic, and whole cell concentrations of platinum were measured by atomic absorption spectroscopy (AAS) after cisplatin, pyriplatin, or phenanthridine treatment of cells. A549, HT29, MRC5, and HeLa cells were treated with 5 μM concentration of the platinum compounds for 3 h. Whole cell, cytoplasm, and nuclear fractions were prepared and analyzed (FIG. 3).

Even at this short exposure time, phenanthriplatin is taken up by cells more effectively than cisplatin or pyriplatin. The results may reflect the ability of the larger, hydrophobic heterocyclic phenanthridine ligand to facilitate uptake of the cationic Pt(II) phenanthriplatin cation through the cytoplasmic membrane. Although the total uptake of platinum is different for each compound, the distribution of phenanthriplatin inside the cell is similar to that of pyriplatin and cisplatin. Most of the platinum is found in the nuclear rather than the cytoplasmic fraction. The remainder, approximately 15-40%, is bound to the insoluble fraction, which consists primarily of cell membranes. The higher cellular uptake levels of phenanthriplatin may contribute to its enhanced cytotoxicity compared to that of cisplatin and pyriplatin.

Reactivity with 5'-dGMP and N-AcMet.

Figure 7A:
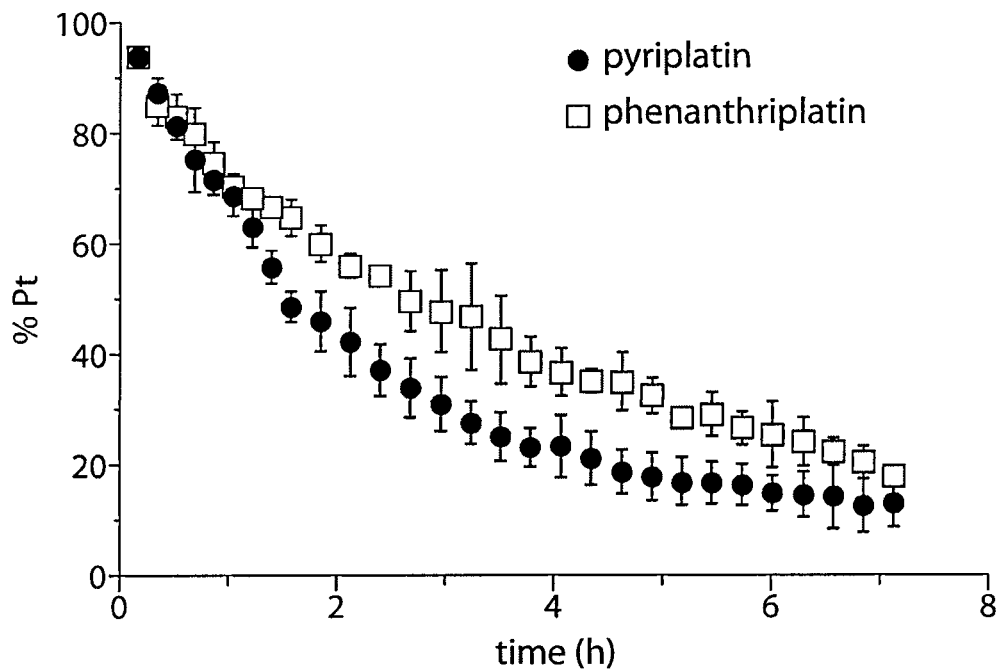
FIG. 7 shows plots of the progress of reactions of pyriplatin and phenanthriplatin with of 5'-dGMP (A) or N-acetyl methionine (B), according to some embodiments.

Platinum-based drugs are activated by the leaving of labile chloride ligands and aquation. The activated, cationic platinum-aqua complexes bind readily to DNA and other nucleophiles (1-3). The aquation rates of pyriplatin and phenanthriplatin in D$_2$O at 37° C. were investigated by $^1$H NMR spectroscopy. Under these conditions, pyriplatin and phenanthriplatin aquate at similar rates; after 1 h the reaction is complete and both of these complexes are in equilibrium with their aqua analogues. The equilibrium constant for aquation is approximately 0.05 for both species. To simulate the interaction of nucleobases on DNA with cationic, monofunctional Pt(II) compounds, pyriplatin and phenanthriplatin were treated with 16 equiv of 5'-deoxyguanosinemonophosphate (5'-dGMP) and monitored by one-dimensional $^1$H NMR spectroscopy. The reactivity of pyriplatin and phenanthriplatin with 5'-dGMP at 37° C. in PBS, pH 7.4. Under these pseudo-first-order conditions, the reactivity of pyriplatin and phenanthriplatin with 5'-dGMP is similar (FIG. 7A). Following a pseudo-first order treatment, the rate constants were computed to be 0.22 h$^{-1}$ and 0.29 h$^{-1}$ for phenanthriplatin and pyriplatin, respectively. The corresponding half-lives of 3.2 h and 2.4 h for phenanthriplatin and pyriplatin suggest that the increased steric bulk supplied by the phenanthridine ligand does not retard binding of phenanthriplatin to N7-guanosine as compared to pyriplatin.

Figure 7B:
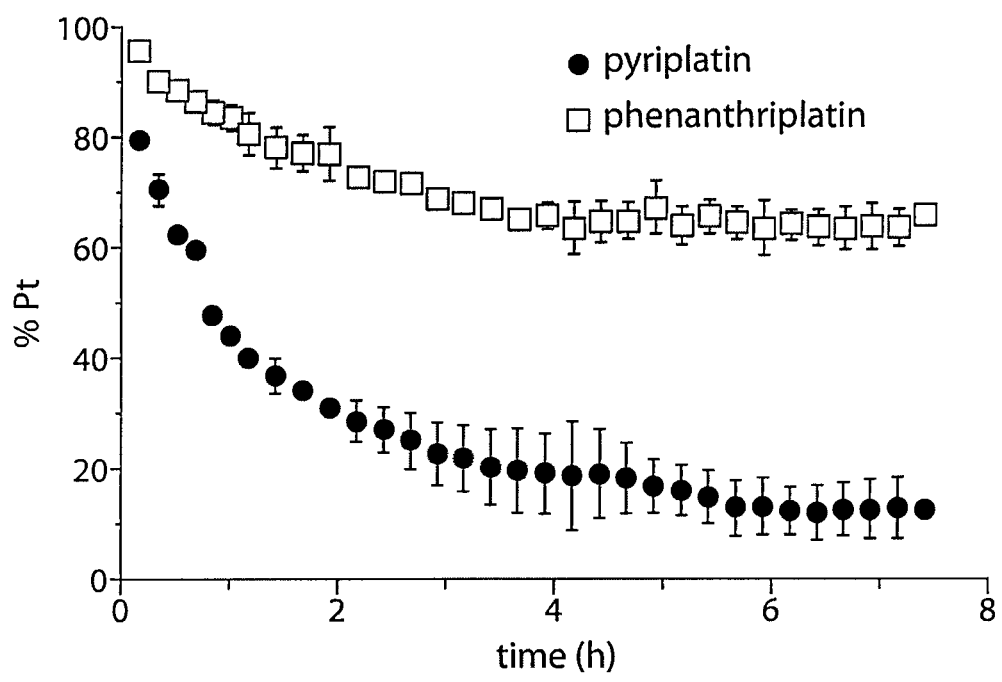

Sulfur-containing molecules, which are widely distributed in cellular systems, can play an important role in the cellular chemistry of platinum drugs, including their uptake, distribution, and efflux. Because of their high binding affinity for platinum, many intracellular sulfur-containing molecules, such as metallothionein and glutathione, bind to platinum before it reaches the nucleus. In this manner they can decrease DNA platination levels and lower the efficacy of Pt compounds. To gain information about the interactions of sulfur-containing compounds with monofunctional Pt(II) compounds, the reactivity of phenanthriplatin and pyriplatin were tested with an equimolar concentration of N-acetyl methionine (N-AcMet) at 37° C. In this experiment, phenanthriplatin reacted much more slowly with N-AcMet than pyriplatin (FIG. 7B). When the kinetic data for phenanthriplatin were fit to an expression for a second-order rate law, the derived rate constant was 0.034 mM$^{-1}$ h$^{-1}$ corresponding to a half-life of 15.0 h. In the case of pyriplatin, the calculated rate constant was 0.56 mM$^{-1}$ h$^{-1}$ with a half-life of 1.04 h, which suggests that the reaction proceeds >10-fold more rapidly than that for phenanthriplatin. ESI-MS data of these reaction mixtures after 48 h revealed the presence of molecular ion peaks corresponding to [Pt(ND$_3$)(Am)(N-AcMet)Cl]$^+$, where Am=pyridine or phenanthridine for pyriplatin and phenanthriplatin, respectively. These species originate from replacement of an ammine ligand trans to N-AcMet, which may be a consequence of the strong trans effect of the sulfur-donor ligand, and therefore represent inactive metabolites of the parent complexes. Although the reaction products of both complexes are similar, the kinetic data reveal that phenanthriplatin is relatively inert to N-AcMet, but exhibits reactivity toward 5'-dGMP similar to that of pyriplatin. The bulky phenanthridine ligand thus may inhibit reaction with N-AcMet more effectively than with 5'-dGMP. This trend may suggests that phenthriplatin binds guanosine nucleosides on DNA efficiently, as required for pol II inhibition, while reacting less readily with cytoplasmic sulfur-containing nucleophiles, which might promote cellular resistance to the compound.

In FIG. 7: Progress of reactions of pyriplatin and phenanthriplatin with (A) 16 equiv of 5'-dGMP at 37° C. or (B) 1 equiv of N-acetyl methionine (N-AcMet) at 37° C. in 10 mM PBS buffer (pH*=7.4) monitored by $^1$H NMR spectroscopy.

(pH*=refers to a pH measurement uncorrected for the effect of deuterium on the electrode.)

Ethidium Bromide DNA-Binding Competition Studies.

Ethidium bromide, a phenanthridine-based dye, is a well-known DNA intercalator. Because the phenanthridine ligand of phenanthriplatin is the same as that in ethidium bromide, an intercalative DNA binding mode of the platinum-bound molecule may be present. To investigate the primary DNA-binding mode of phenanthriplatin, the affinity of ethidium bromide for calf thymus DNA in the presence of different platinum compounds was investigated, and the data were subjected to a Scatchard analysis (e.g., see Howe-Grant M, Wu K C, Bauer W R, Lippard S J (1976) Binding of platinum and palladium metallointercalation reagents and antitumor drugs to closed and open DNAs. Biochemistry 15:4339-4346). Using this approach, it is possible to determine whether the inhibition of ethidium binding is competitive (type A), non-competitive (type D), or both (type B). No inhibition of ethidium binding is labeled as type C. Scatchard plots obtained after a 1 min incubation period for cisplatin, pyriplatin, or phenanthriplatin revealed type C behavior, indicating that, at this short incubation time, none of the platinum complexes inhibit ethidium intercalation, presumably due to the slow kinetics that characterizes the formation of covalent adducts. After a 12-h incubation period of DNA with the platinum compounds, type C behavior was observed for cisplatin and pyriplatin, whereas type D behavior occurred for phenanthriplatin. This indicates that phenanthriplatin inhibits ethidium binding non-competitively and, therefore, that the binding mode of phenanthriplatin to DNA is not intercalative. Covalent adducts of phenanthriplatin may be responsible for the non-competitive inhibition of ethidium binding.

Transcription Assays.

Investigations of the cellular processing of Pt-DNA lesions are important for understanding the mechanism of action of platinum drugs. One of the major consequences of Pt-DNA damage is transcription inhibition, the extent of which dictates the efficacy of Pt drugs. The transcription inhibitory properties of phenanthriplatin were investigated and compared the results to those for cisplatin and pyriplatin using live mammalian cells via a described protocol (e.g., see Ang W H, Myint M, Lippard S J (2010) Transcription inhibition by platinum-DNA crosslinks in live mammalian cells. J Am Chem Soc 132:7429-7435). Globally platinated pGLuc plasmids were generated by treating pGLuc with varying concentrations of cisplatin, pyriplatin, or phenanthriplatin in HEPES buffer.

Figure 4:
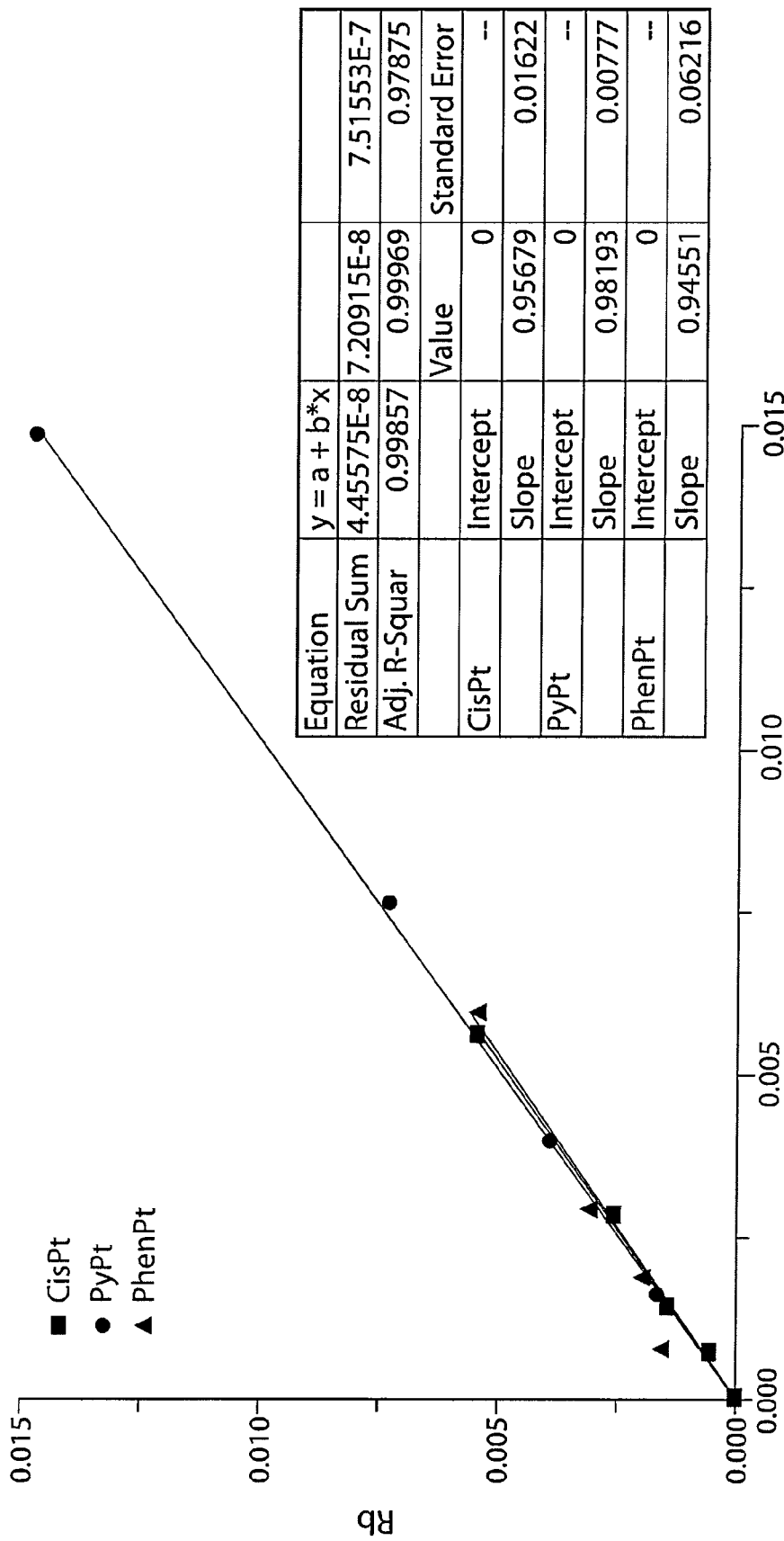
FIG. 4 shows plots of platination of pGLuc after treatment with cisplatin, pyriplatin, or phenanthriplatin, according to some embodiments.

In one embodiment, the ratio of bound platinum per plasmid was determined by measuring the Pt concentration by atomic absorption spectroscopy and the DNA concentration by UV/Vis spectroscopy. Transcription levels were investigated by determining GLuc expression from transfected A549 and HT29 cells. A series of plasmids with Pt/plasmid ratios ranging from 0 to ~120 were prepared by reaction with cisplatin, pyriplatin, or phenanthriplatin. For cisplatin, the $r_f$ values (Pt per nucleotide in reaction) of 0, 0.00074, 0.0014, 0.0028, 0.0056, resulted in $r_b$ values 0, 0.0006, 0.0015, 0.0026, 0.0054, corresponding to 0, 4.64, 11.67, 20.65, and 43.35 Pt adducts per plasmid. For pyriplatin, the $r_f$ values were 0, 0.0016, 0.004, 0.0076, 0.015, the $r_b$ values were 0, 0.0017, 0.0039, 0.0073, 0.0015, and the corresponding ratios were 0, 13.33, 31.19, 57.96, and 117.31 Pt per plasmid. The $r_f$ values were 0, 0.0008, 0.0019, 0.0029, 0.0060, the $r_b$ values were 0, 0.0015, 0.0019, 0.0030, 0.0053, and the corresponding ratios were 0, 12.12, 15.42, 24.28, and 42.80 Pt per plasmid for phenanthriplatin. The level of DNA-bound pyriplatin or phenanthriplatin per amount added was almost identical to that of cisplatin as revealed by plots of $r_b$ vs. $r_f$ (FIG. 4). In FIG. 4: Platination of pGLuc after treatment with cisplatin, pyriplatin, or phenanthriplatin for 16 h at 37° C. in buffer (24 mM HEPES pH 7.4, 10 mM NaCl).

Figure 5:
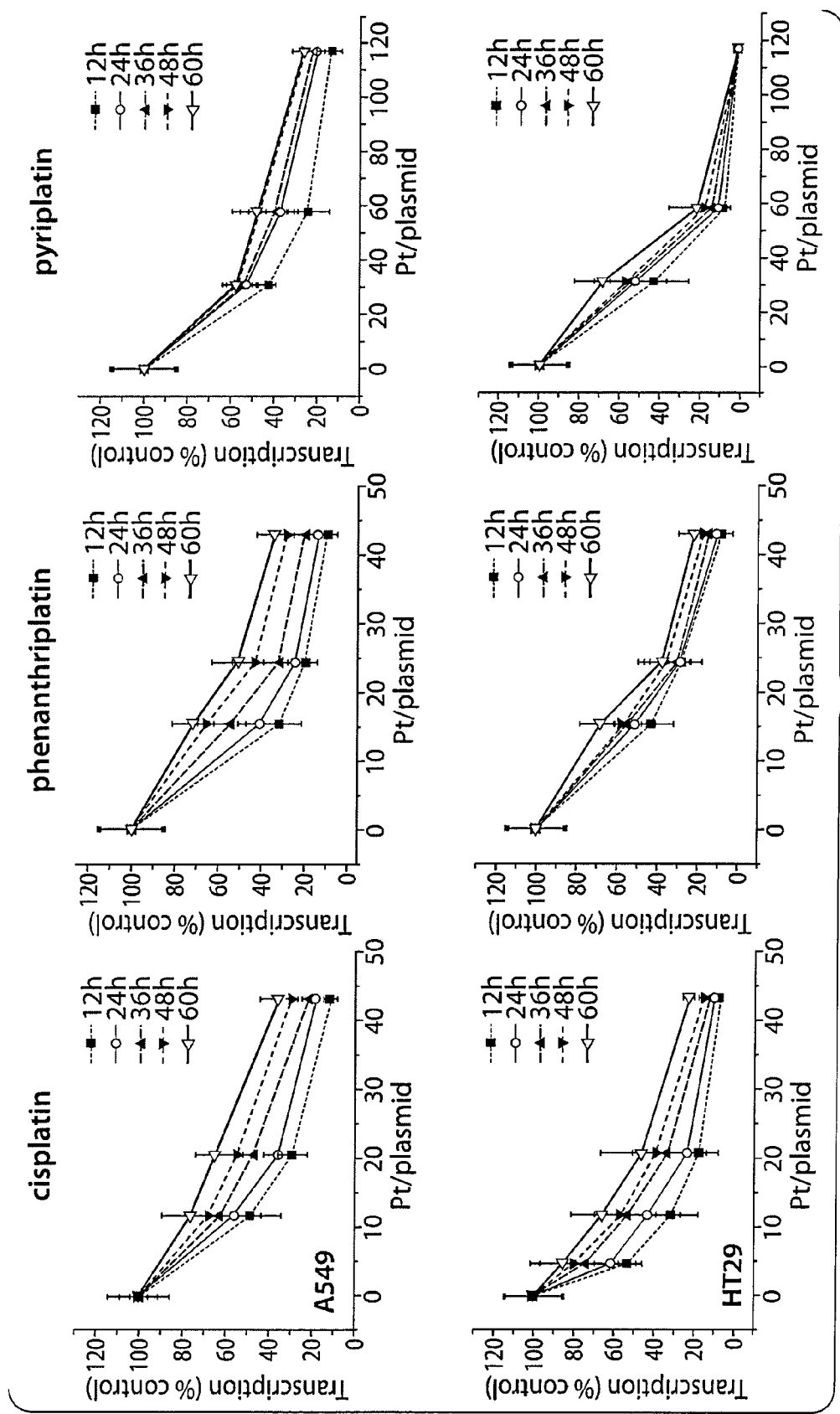
FIG. 5 shows transcription profiles of globally platinated probes in A549 (top) and HT29 (bottom) cells, according to some embodiments.

A549 or HT29 cells were transfected using these platinated transcription probes for 2 h at 37° C. and cell media were collected at 12, 24, 36, 48, and 60 h after the transfection. The levels of GLuc expression in cells were measured using a luminometer. The intensity values were normalized against controls (unplatinated plasmid). Transcription profiles were obtained by plotting normalized levels of GLuc expression against platination levels (Pt/plasmid ratio) at five different time points (FIG. 5). Phenanthriplatin inhibited transcription in A549 and HT 29 cells as strongly as cisplatin. The cytotoxicity of phenanthriplatin was correlated with its ability to inhibit transcription. In FIG. 5: transcription profiles of globally platinated probes in A549 (top) and HT29 (bottom) cells.

In another embodiment, A549 or HT29 cells were transfected using the platinated transcription probes, and transcription levels were investigated by determining GLuc expression as measured by fluorescence following addition of coelenterazine as a substrate for the exported enzyme. The emission intensities were normalized against unplatinated plasmids as a control. Transcription profiles were obtained by plotting normalized levels of GLuc expression against platination levels (Pt/plasmid ratio) at five different time points. After 60 h, the transcription levels were substantially restored in both cell lines, indicating repair of monofunctional Pt(II)-DNA and cisplatin-DNA adducts. For example, at a Pt/DNA ratio of 24.3 for phenanthriplatin, the transcription level recovered from 19.5% at 12 h to 51.1% at 60 h in A549 cells, whereas the recovery was 25.8% to 60.2% for cisplatin and 55.2% to 66.8% for pyriplatin. In HT29 cells, the transcription re-covered from 28.1% at 12 h to 37.6% at 60 h at a Pt/DNA ratio of 24.3 for phenanthriplatin, whereas the recovery was 15.6% to 42.9% for cisplatin and 55.3% to 75.2% for pyriplatin. $D_0$ values, defined as the number of Pt lesions per plasmid required to reduce transcription levels to 37% of control, were computed to quantitate transcription inhibition in the two cell lines (Table 6). An increase in $D_0$ value at different time points represents restoration of transcription. Phenanthriplatin inhibits transcription in A549 and HT29 cells as efficiently as cisplatin. The transcription inhibition by pyriplatin was less efficient than that of either cisplatin or phenanthriplatin by a factor of two. The more effective transcription inhibition of phenanthriplatin-DNA adducts compared to those of pyriplatin may be a significant factor contributing to its increased cytotoxicity.

TABLE 6

$D_0$ values of globally platinated probes with cisplatin, phenanthriplatin, or pyriplatin assayed at different time intervals after transfection for A549 and HT29 cells

| Time after Transfection (h) | A549 (Pt/plasmid) | | | HT29 (Pt/plasmid) | | |
|---|---|---|---|---|---|---|
| | cisplatin | phenanthriplatin | pyriplatin | cisplatin | phenanthriplatin | pyriplatin |
| 12 | 16.8 | 14.2 | 39.2 | 9.9 | 18.9 | 35.6 |
| 24 | 20.0 | 17.3 | 58.5 | 14.5 | 21.1 | 40.5 |
| 36 | 29.5 | 22.2 | 68.8 | 19.2 | 21.9 | 42.9 |
| 48 | 36.4 | 31.6 | 85.2 | 22.1 | 23.5 | 44.5 |
| 60 | 42.6 | 39.8 | 89.1 | 30.0 | 25.0 | 49.3 |

Example 2

This example relates to determining the maximum tolerated dose (MTD) of phenanthriplatin in mice. The maximum tolerated dose (MTD) is defined as the highest dose of a drug or treatment that does not cause any adverse side effects. This example describes determination of the MTD of phenanthriplatin administered intravenously to Albino ICR mice.

Experimental Section

Animals.

In this study, 42 healthy Albino ICR female mice (19.9-28.7 g weight) were used.

Detailed Procedure.

In Phase 1 of the study, 12 ICR albino mice were designated to receive 4 different concentrations of phenanthriplatin (Table 7) via tail vein injection. Three additional mice were dosed with PBS to serve as a vehicle control. In the Phase 2 of the study, 24 ICR albino mice were designated to receive 8 different concentrations of phenanthriplatin (Table 8) via tail vein injection. Three additional mice were dosed with PBS to serve as a vehicle control. Mice were observed for negative effects immediately following dosing, after an additional 15 mins and daily thereafter. Body weights were recorded daily.

TABLE 7

Phase 1

| Group | Test Article | Concentration (mg/kg) | Route | Dose Volume (mL/kg) | Number of Animals |
|---|---|---|---|---|---|
| 1 | PBS | 0 | IV | 10 | 3 |
| 2 | Phenanthriplatin | 15 | | 10 | 3 |
| 3 | | 1.5 | | 10 | 3 |
| 4 | | 0.15 | | 10 | 3 |
| 5 | | 0.015 | | 10 | 3 |

TABLE 8

Phase 2

| Group | Test Article | Concentration (mg/kg) | Route | Dose Volume (mL/kg) | Number of Animals |
|---|---|---|---|---|---|
| 1 | PBS | 0 | IV | 10 | 3 |
| 2 | Phenanthriplatin | 1.5 | | 10 | 3 |
| 3 | | 2.1 | | 10 | 3 |
| 4 | | 2.9 | | 10 | 3 |
| 5 | | 4 | | 10 | 3 |
| 6 | | 5.6 | | 10 | 3 |
| 7 | | 7.8 | | 10 | 3 |
| 8 | | 10.8 | | 10 | 3 |
| 9 | | 15 | | 10 | 3 |

Results

Mortality.

In Phase 1, two animals from Group 2 (15 mg/kg) died immediately after dosing and the 3rd animal was not dosed under the assumption that this dose was lethal. No mortality from the other groups was observed.

In Phase 2 of the Study, one animal died from Group 9 (15 mg/kg) immediately after dosing. The other two animals were not dosed under the assumption that this dose was lethal. In Group 8 (10.8 mg/kg), one animal died immediately after dosing. The other two animals were not dosed under the assumption that this dose was lethal. In Group 7 (7.8 mg/kg), three animals were dosed. Two animals died within a few minutes after dosing. One animal survived until end of the study. In Group 6 (5.6 mg/kg), three animals were dosed. One animal died within a few minutes after dosing. The remaining two animals survived until end of the study. In Group 5 (4 mg/kg), Group 4 (2.9 mg/kg), Group 3 (2.1 mg/kg), Group 2 (1.5 mg/kg), and Group 1 (PBS), three animals were dosed, and no mortality was observed. In all animals that survived past the first day no significant change in body weight was observed (Tables 9 and 10).

Based on this study, the MDT of phenanthriplatin is approximately 4 mg/kg.

TABLE 9

Phase 1: Mean ± SD Body Weight (N = 3/group)

| Groups | Day 1 | Day 2 | Day 3 | Day 4 | Day 5 | Day 6 | Day 7 | Day 8 |
|---|---|---|---|---|---|---|---|---|
| 1 Control | 24.3 ± 1.7 | 22.9 ± 1.1 | 24.2 ± 1.7 | 24.5 ± 1.7 | 24.8 ± 1.7 | 25.4 ± 1.8 | 24.5 ± 2.2 | 25.0 ± 1.7 |
| 2 15 mg/kg | 23.1 ± 0.8 | N/A | N/A | N/A | N/A | N/A | N/A | N/A |
| 3 1.5 mg/kg | 21.5 ± 1.0 | 20.8 ± 1.1 | 21.6 ± 1.7 | 23.1 ± 2.0 | 23.8 ± 1.8 | 24.5 ± 1.6 | 22.6 ± 2.3 | 22.8 ± 1.6 |

TABLE 9-continued

Phase 1: Mean ± SD Body Weight (N = 3/group)

| Groups | Day 1 | Day 2 | Day 3 | Day 4 | Day 5 | Day 6 | Day 7 | Day 8 |
|---|---|---|---|---|---|---|---|---|
| 4 0.15 mg/kg | 21.4 ± 1.3 | 21.1 ± 1.4 | 21.7 ± 1.4 | 22.6 ± 1.5 | 26.6 ± 2.4 | 24.1 ± 1.4 | 21.3 ± 1.2 | 22.6 ± 1.7 |
| 5 0.015 mg/kg | 21.5 ± 0.8 | 20.3 ± 0.2 | 20.8 ± 0.4 | 21.2 ± 0.4 | 22.1 ± 0.4 | 22.8 ± 0.3 | 21.5 ± 0.5 | 21.7 ± 1.2 |

TABLE 10

Phase 2: Mean ± SD Body Weight

| Groups | Day 1 | Day 2 | Day 3 | Day 4 | Day 5 | Day 6 | Day 7 | Day 8 |
|---|---|---|---|---|---|---|---|---|
| 1 Control | 25.5 ± 1.5 | 26.4 ± 1.1 | 26.4 ± 1.2 | 26.6 ± 1.4 | 26.6 ± 1.4 | 25.9 ± 1.3 | 26.0 ± 1.2 | 26.0 ± 1.1 |
| 2 1.5 mg/kg | 24.4 ± 1.5 | 24.1 ± 2.1 | 23.6 ± 2.5 | 23.6 ± 2.8 | 23.9 ± 2.4 | 24.1 ± 2.5 | 24.5 ± 2.1 | 24.4 ± 2.0 |
| 3 2.1 mg/kg | 26.9 ± 1.7 | 27.8 ± 2.1 | 27.1 ± 1.8 | 27.8 ± 2.1 | 28.1 ± 2.0 | 27.7 ± 1.8 | 27.3 ± 1.0 | 27.5 ± 1.7 |
| 4 2.9 mg/kg | 24.1 ± 2.1 | 24.5 ± 0.9 | 24.7 ± 1.8 | 25.1 ± 2.0 | 25.2 ± 1.7 | 24.3 ± 0.8 | 24.1 ± 1.5 | 24.0 ± 1.0 |
| 5 4.0 mg/kg | 26.1 ± 1.3 | 26.9 ± 2.3 | 26.3 ± 1.0 | 27.4 ± 1.0 | 26.7 ± 1.1 | 26.4 ± 1.2 | 26.1 ± 1.1 | 26.2 ± 1.2 |
| 6 5.6 mg/kg | 26.5 ± 0.8 | 26.2 | 26.6 | 26.8 | 26.0 | 26.2 | 26.7 | 26.5 |
| 7 7.8 mg/kg | 24.0 ± 2.8 | 24.4 | 26.5 | 26.1 | 26.3 | 26.5 | 25.4 | 25.7 |
| 8 10.8 mg/kg | 26.1 ± 0.4 | N/A | N/A | N/A | N/A | N/A | N/A | N/A |
| 9 15.0 mg/kg | 27.5 ± 0.8 | N/A | N/A | N/A | N/A | N/A | N/A | N/A |

Example 3

This example describes the encapsulation of phenanthriplatin into polymeric nanoparticles by using double emulsion with PLGA-PEG-COOH and nanoprecipitation with functionalized PLA-OH and PLGA-PEG-COOH.

Experimental Section

Materials and Measurements.

Phenanthriplatin was synthesized as previously described. All chemicals and solvents are commercially available. $^1$H, $^{13}$C and $^{195}$Pt NMR spectra were recorded on a Bruker AVANCE-400 NMR spectrometer with a Spectro Spin superconducting magnet in the Massachusetts Institute of Technology Department of Chemistry Instrumentation Facility (MIT DCIF). Electrospray ionization-MS (ESI-MS) spectra were obtained on an Agilent Technologies 1100 Series liquid chromatography/MS instrument. Atomic absorption spectroscopic measurements were taken on a Perkin Elmer AAnalyst 600 spectrometer. Elemental analyses were performed by Midwest Microlab, LLC, Indianapolis, Ind. Distilled water was purified by passage through a Millipore Milli-Q Biocel water purification system (18.2 MS2) with a 0.22 µm filter. Size and zeta potentials of NPs were obtained by using a ZetaPALS (Brookheaven Instruments Corporation) dynamic light-scattering detector at Koch Institute (MIT). Transmission electron microscopy (TEM) was performed by using a Tecnai™ $G^2$ Spirit BioTWIN instrument.

Synthesis of cis,trans-[Pt(NH$_3$)$_2$(phenanthridine)Cl (OH)$_2$]NO$_3$.

Phenanthriplatin (cis-[Pt(NH$_3$)$_2$(phenanthridine)Cl]NO$_3$) (0.3 g, 0.59 mmol) was dissolved in 15 mL of 30% aqueous H$_2$O$_2$, and the solution was stirred for 2 h at 55° C. The yellow solution was then evaporated under reduced pressure to dryness. The residue was washed with diethyl ether (10 mL×2 times). The compound was purified by redissolving in 10% methanol in water (10 mL) and precipitating by adding it dropwise to vigorously stirred diethyl ether (50 mL). The supernatant was decanted, and the pale yellow powder was washed 2 times with 50 mL of diethylether. The final compound was isolated by vacuum filtration and dried in vacuo. Pale yellow solid. Yield: 87% (0.28 g, 0.52 mmol). ESI-MS m/z calculated (M$^+$): 575.14. found: 575.2. $^1$H NMR (DMSO-d$_6$): δ 6.20 (6H, broad), 7.84 (3H, q, J=8 Hz), 7.96 (1H, t, J=8 Hz), 8.20 (1H, t, J=8 Hz), 8.92 (1H, d, J=8 Hz), 9.00 (1H, d, J=8 Hz), 9.83 (1H, d, J=8 Hz), 10.07 (1H, t, J=16 Hz). $^{13}$C NMR (DMSO-d$_6$): δ 122.35, 122.97, 125.24, 128.41, 128.74, 129.03, 131.49, 133.24, 135.47, 140.58, 160.46. $^{195}$Pt NMR (DMSO-d$_6$): δ 838.66. Anal. Calcd. for C$_{13}$H$_{17}$Cl$_1$N$_4$O$_5$Pt: C, 28.92; H, 3.17; N, 10.38. Found: C, 28.98; H, 3.19; N, 10.15.

Synthesis of cis-[Pt(NH$_3$)$_2$(phenanthridine)Cl(succinate) (OH)]NO$_3$ (PhenPt(IV)).

To a solution of cis,trans-[Pt(NH$_3$)$_2$(phenanthridine)Cl (OH)$_2$]NO$_3$ (0.2 g, 0.37 mmol) in 15 mL DMF, succinic anhydride (0.045 g, 0.45 mmol, 1.2 equiv) was added, and the reaction was stirred at 55° C. After 12 h, the yellow solution was then evaporated under reduced pressure. The residue was washed with acetone (25 mL×2 times) to remove excess succinic anhydride. The compound was reprecipitated by redissolving in methanol (10 mL) and adding diethyl ether (70 mL). The buff colored powder was filtered and washed 2 times with 50 mL of diethylether. The final product was dried in a desiccator. Buff color solid. Yield: 55% (0.13 g, 0.29 mmol). ESI-MS m/z calculated (M$^+$): 577.08. found: 577.1. $^1$H NMR (DMSO-d$_6$): δ 2.38 (2H, m), 2.56 (2H, s), 6.53 (6H, broad), 7.88 (2H, m), 7.98 (1H, t, J=4 Hz), 8.23 (1H, t, J=8 Hz), 8.36 d, J=8 Hz), 8.96 (1H, d, J=8 Hz), 9.02 (1H, d, J=8 Hz), 9.10 (1H, d, J=8 Hz), 9.90 (1H, s), 12.07 (1H, s). $^{13}$C NMR (DMSO-d$_6$): δ 30.39, 122.36, 123.34, 128.59, 129.18, 131.61, 133.36, 135.80, 178.82. $^{195}$Pt NMR (DMSO-d$_6$): δ 927.25, 962.38. Anal. Calcd. for C$_{17}$H$_{21}$Cl$_1$N$_4$O$_8$Pt: C, 31.91; H, 3.31; N, 8.76. Found: C, 32.07; H, 3.45; N, 8.44.

Encapsulation of Phenanthriplatin via Double Emulsion Nanoprecipitation (Construct 1).

The copolymer PLGA-PEG-COOH was synthesized by amide coupling between COOH-PEG-NH$_2$ and PLGA-COOH in methylene chloride using N-hydroxysuccinimide (NHS) and 1-ethyl-3-[3-dimethylaminopropyl]carbodiimide hydrochloride (EDC). Phenanthriplatin-containing NPs were prepared by the double emulsion method. A 666 μL aliquot of a PLGA-PEG-COOH (5 mg/ml in 1:1=acetone:methylene chloride) solution and 166 μL of an aqueous phenanthriplatin solution at varying concentrations were combined in a 4 mL vial and sonicated at 10 watt for 30 sec. This mixture was quickly added to 6.7 mL water in a 20 mL vial then sonicated at 10 watt for 30 sec to afford the double emulsion. The final mixture was poured into 27 mL of water containing 0.05% polyvinyl alcohol (PVA) in a 50 ml beaker, and stirred at room temperature for 3 h. The phenanthriplatin-containing NPs were filtered through a 0.22 μm filter, and then washed 3 times using an Amicon ultracentrifugation filtration device with a molecular mass cutoff of 100 kDa. The NP size was obtained by quasi-elastic laser light scattering by using a ZetaPALS dynamic light-scattering instrument. The Pt concentration in the NPs was measured by atomic absorption spectroscopy.

Synthesis of PLA-PhenPt(IV).

0.5 g (0.782 mmol) of cis-[Pt(NH$_3$)$_2$(phenanthridine)Cl (succinate)(OH)]NO$_3$ (0.2 g, 0.46 mmol) was dissolved in 4 mL anhydrous dimethylformamide (DMF) and added to a DMF solution (0.5 mL) containing 135 mg (1 mmol) of N-hydroxybenzotriazole and 240 mg (1.17 mmol) of N,N'-dicyclohexylcarbodiimide (DCC). The solution was stirred for 30 min at room temperature. To this mixture, 800 mg of PLA-OH (in 1 ml of 1:1 DCM/DMF) was The reaction mixture was stirred overnight. The polymer solution was filtered, concentrated, and reprecipitated by adding diethyl ether. The resulting polymer was redissolved in dichloromethane (DCM) and filtered several times to remove unreacted coupling reagents. The final solution was concentrated and diethyl ether was added to give a pale yellow solid. The crude PLA-PhenPt(IV) polymer was purified several times by dissolution-reprecipitation using DCM-diethyl ether and finally dried to obtain the conjugated PLA-PhenPt(IV). Polymer PLA-PhenPt(IV) was characterized by $^1$H NMR, and the molecular weight of the final polymer was 17 K, which was obtained by gel permeation chromatography. From atomic absorption studies, ~7.3% w/w of phenanthriplatin was conjugated with respect to polymer.

Preparation of Phenanthriplatin-Conjugated NPs (Construct 2).

Nanoparticles were formulated by mixing different ratios of DCM solutions of two different polymers, PLGA-PEG-COOH and PLA-PhenPt(IV). Final concentrations of polymer in mixed solutions were maintained between 10-15 mg/ml (in DCM). NPs were formed by adding mixed polymer solutions dropwise into stirred water. Size and zeta potentials were recorded using a Zeta potential analyzer. Zeta potentials for all the NPs formulations are approximately −20 to −30 mV. The overall size of all these NPs ranged from 100 nm to 145 nm and the polydispersity was between 0.1 and 0.001.

Release of Phenanthriplatin from Construction 1 and Construction 2.

An aqueous suspension of construct 1 was aliquotted (200 μL) into semipermeable minidialysis tubes (molecular mass cutoff 100 kDa; Pierce) and dialyzed against 13 L PBS (pH 7.4) at 37° C. Samples were removed periodically over a period of 100 h, and the platinum concentration was determined by AAS. In a similar manner, construct 2, were formed by using 1:1 PLGA-PEG and PLA-PhenPt(IV), was resuspended in water, aliquotted (100 μL), and dialyzed against 20 L of PBS (pH 7.4) at 37° C. At predetermined times, aliquots of the NP suspension were removed and dissolved in acetonitrile. The platinum content was determined by AAS.

Transmission Electron Microscopy (TEM) Images.

TEM images were recorded for construct 2. Grids were stained with uranyl acetate.

| Ratio (PLGA-PEG-COOH:PLA-PhenPt(IV)) | Particle Size (nm) |
| --- | --- |
| 2:1 | 124.1 |
| 1:1 | 128.2 |
| 1:3 | 143.5 |

Cell Lines and Cell Culture.

Human prostate carcinoma (PC3) and human cervix carcinoma (HeLa) cells were obtained from the ATCC. The human lung carcinoma cell line A549 was kindly provided by David E. Root (Whitehead Institute for Biomedical Research). Cells were incubated at 37° C. in 5% CO$_2$ and grown in RPMI (PC3) or DMEM (A549 and HeLa) medium supplemented with 10% fetal bovine serum and 1% penicillin/streptomycin. Cells were passaged every 3 to 4 days and restarted from the frozen stock upon reaching passage number 20.

MTT Assay.

The cytotoxic behavior of cisplatin, phenanthriplatin, construct 1, and construct 2 was evaluated using the MTT assay. Solutions of the platinum agents were freshly prepared in sterile PBS before use and the platinum content was quantitated by AAS. Cells were seeded on 96 well plates (1200 cells per well) in 100 μL RPMI or DMEM media\ and incubated for 24 hours. The cells were then treated with cisplatin, phenanthriplatin, construct 1, or construct 2, separately at varying concentrations, and incubated for 72 h at 37° C. The cells were then treated with 20 μL of 3-(4,5-dimethylthiazol-2-yl)-2,5-diphenyltetrazolium bromide (MTT) (5 mg/mL in PBS) and incubated for 4 h. The medium was removed, 100 μL of DMSO were added to the cells, and the absorbance of the purple formazan was recorded at 570 nm using a BioTek Synergy HT multi-detection microplate plate reader. For each cell line, three independent experiments were carried out in triplicate.

Results

Development of Construct 1.

Figure 8:
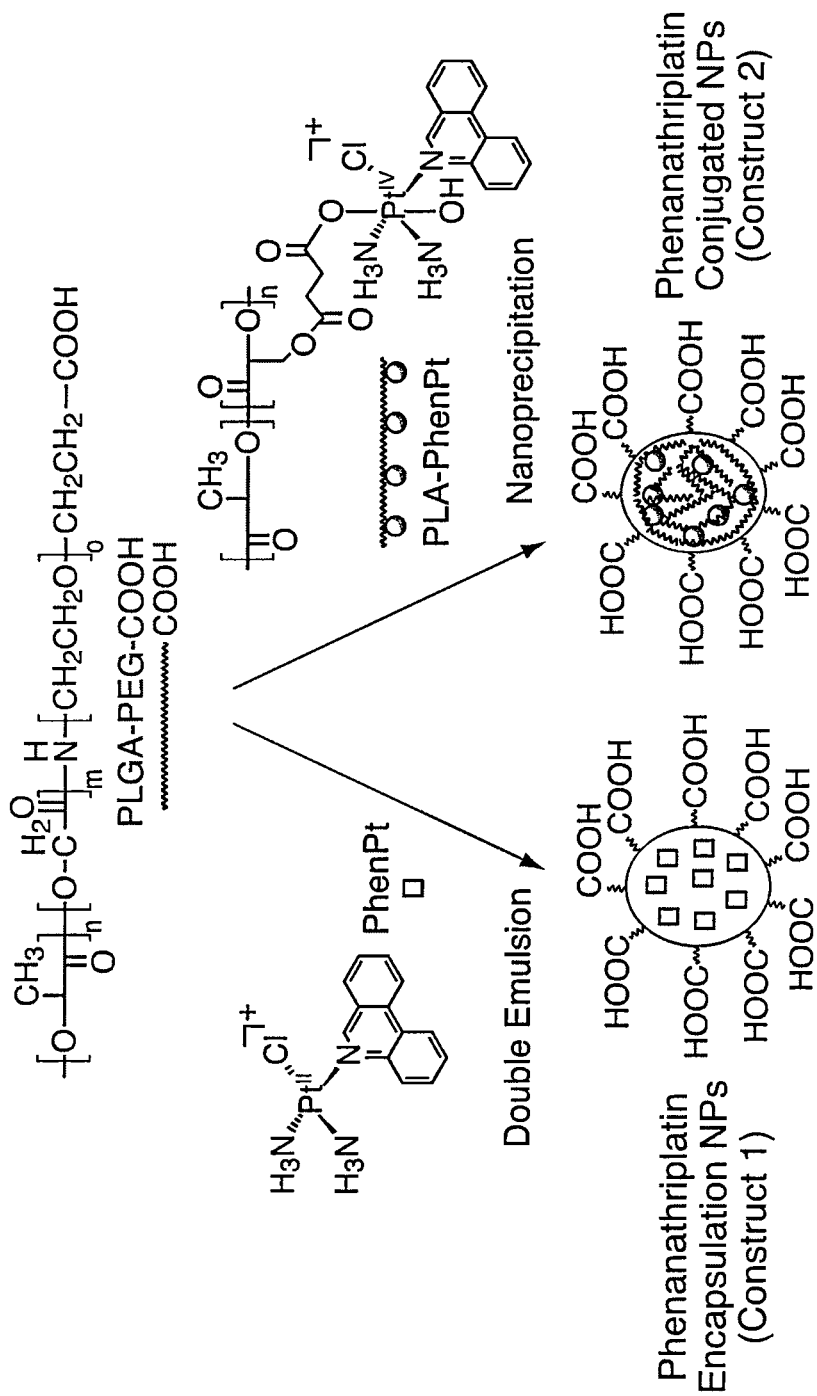
FIG. 8 illustrates the synthesis of phenanthriplatin conjugated NPs and phenanthriplatin encapsulation NPs, according to some embodiments.

To encapsulate the monofunctional Pt(II) compound, phenanthriplatin, a double emulsion procedure was tested (FIG. 8). Conventional nanoprecipitation gave very low loading efficiency of phenanthriplatin. Therefore, a double emulsion nanoparticle system was used, comprising PLGA-PEG-COOH polymer and PVA as a surfactant. Under optimized conditions, 1% loading could be achieved in nanoparticles of about 170 nm.

FIG. 8 illustrates the construction of phenanthriplatin conjugated NPs and phenanthriplatin encapsulation NPs.

Monofunctional Platinum(IV) Phenanthriplatin Analog for NPs (PhenPt(IV)).

The cationic nature of the monofunctional Pt(II) compound, phenanthriplatin may inherently limit its lipophilicity. A monofunctional Pt(IV) moiety was directly attached to the polymer backbone. To accomplish this goal, an asymmetrically modified $[Pt(IV)(NH_3)_2(phenanthridine)(Cl)(OH)(succinate)]^+$ (PhenPt(IV)) was synthesized via reported methods (e.g., see J Am Chem Soc 2007, 129, 8438-8439 and J Am Chem Soc 2008, 130, 11467-11476). The succinate group allowed coupling to the functionalized PLA-OH polymer chain. The product was characterized by spectroscopic and analytical methods such as $^1H$, $^{13}C$, and $^{195}Pt$ NMR, ESI-MS and elemental analysis.

Development of Construct 2.

To prepare the nanoparticles, two kinds of polymers were employed: a polylactide derivative with pendant hydroxyl functional groups (PLA-OH) as a conjugation polymer to a monofunctional phenanthriplatin(IV) pro-drug (PhenPt(IV)) (Scheme 1), and carboxyl-terminated poly(D,L-lactic-co-glycolic acid)-poly(ethylene glycol), PLGA-PEG-COOH as a controlled release polymer (FIG. 8). Synthetic PLA-OH was conjugated with PhenPt(IV), then the nanoparticles were assembled using PLGA-PEG-COOH via nanoprecipitation (FIG. 8).

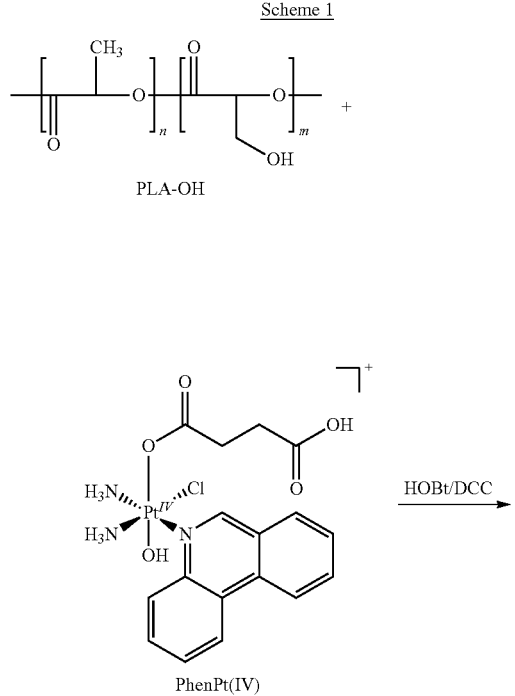

Scheme 1

PLA-OH

PhenPt(IV)

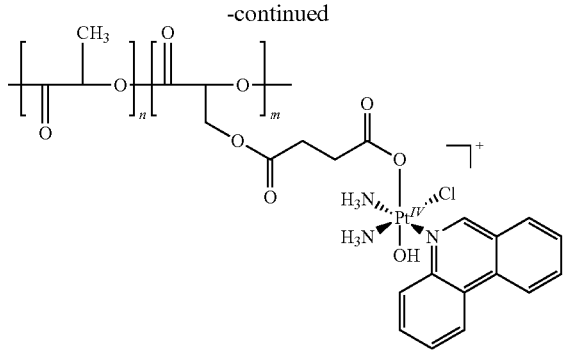

PLA-PhenPt(IV)

Nanoparticle properties were characterized using dynamic light scattering to determine size. Surface morphology and size was also determined by transmission electron microscopy (TEM). Platinum content in the NPs was determined by using platinum atomic absorption spectroscopy (AAS). The size of NPs ranged from 100 nm to 145 nm and the encapsulation efficiency of NPs was 88%.

In vitro Release of Phenanthriplatin from Construct 1 or Construct 2.

Figure 9:
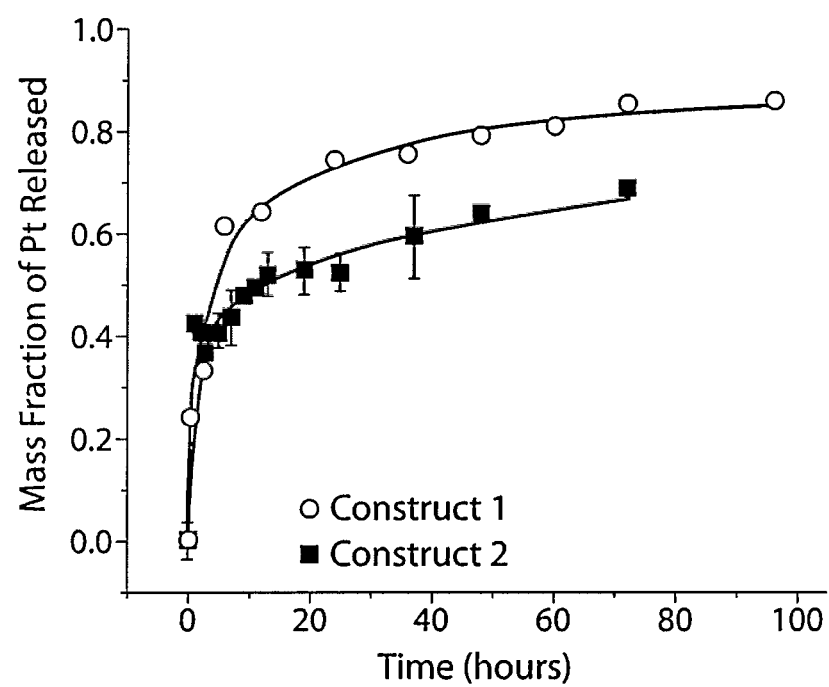
FIG. 9 shows plots of release of phenanthriplatin from phenanthriplatin encapsulation NPs or phenanthriplatin conjugated NPs at 37° C. in PBS, according to some embodiments.

The platinum compounds were physically dispersed by encapsulation throughout the hydrophobic core of the NPs. In order to study the release of platinum compounds from the nanoparticle system in physiological conditions, NP suspensions were dialyzed against to PBS at pH 7.4 and 37° C. The amount of phenanthriplatin released from the NPs was measured by AAS. The release of platinum compound from the NPs is shown in FIG. 9. Both construct 1 and construct 2 showed an initial burst release during the first 3 h comprising 30-40% of the total platinum. Thereafter, a period of controlled platinum release occurs, reaching a value of 75% and 52% for construct 1 and construct 2, respectively, after 24 h. Such controlled release of phenanthriplatin from the NPs extended over 100 h. Notably, in construct 2, the release Pt remained less than 60% over 80 h in contrast to that of construct 1, which released up to 80% over the same time period.

In FIG. 9: Release of phenanthriplatin from construct 1 or construct 2 at 37° C. in PBS.

In Vitro Cytotoxicity.

Figure 10:
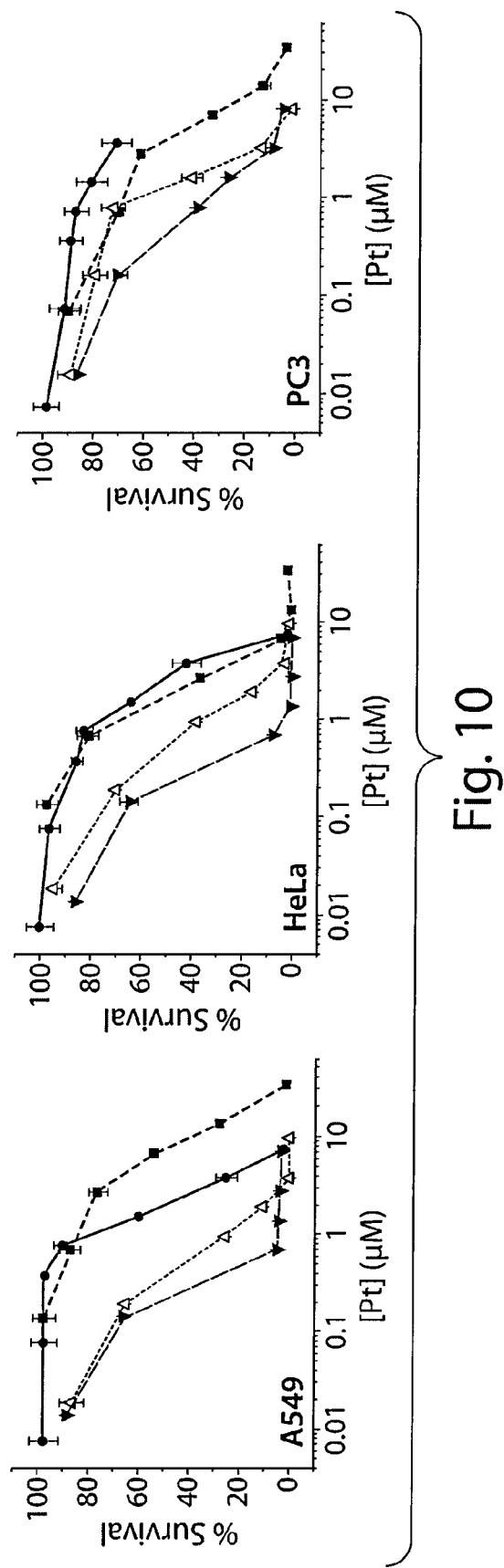
FIG. 10 shows cytotoxicity profiles of phenanthriplatin (▼), phenanthriplatin encapsulation NPs (▲), phenanthriplatin conjugated NPs (●), and cisplatin (■) with A549, HeLa, and PC3 cells, according to some embodiments.

To investigate the anti-cancer potential of constructs 1 and 2, a series of in vitro cytotoxicity assays were performed using A549, HeLa, and PC3 cell lines and directly compared their efficacies to those of phenanthriplatin and cisplatin. As shown in FIG. 10 and Table 11, construct 1 was less cytotoxic to all three cell lines when compared to phenanthriplatin but is highly cytotoxic when compared to cisplatin. Under the same conditions, construct 2 had an $IC_{50}$ values higher than that of construct 1 or phenanthriplatin, and even higher than those of cisplatin in HeLa and PC3 cells. These results demonstrate that the nanoparticle delivery system decreased the cytotoxicity of phenanthriplatin. The diminished cytotoxicity of construct 2 may be explained by the slow release of Pt described above.

In FIG. 10: Cytotoxicity profiles of phenanthriplatin (▼), construct 1 (▲), construct 2 (●), and cisplatin (■) with A549, HeLa, and PC3 cells for 72 h at 37° C.

TABLE 11

IC 50 values of phenanthriplatin, construct 1, construct 2, and cisplatin in A549, HeLa, and PC3 cells.

| | | IC$_{50}$ (μM) | | | |
|---|---|---|---|---|---|
| Cell Line | Cancer Type | Cisplatin | Phenanthriplatin | Construct 1 | Construct 2 |
| A549 | Lung | 6.47 ± 0.74 | 0.22 ± 0.006 | 0.33 ± 0.06 | 1.82 ± 0.1 |
| HeLa | Cervix | 1.7769 ± 0.15 | 0.21 ± 0.035 | 0.53 ± 0.036 | 2.36 ± 0.41 |
| PC3 | Prostate | 3.93 ± 0.52 | 0.60 ± 0.25 | 1.26 ± 0.03 | >10 |

Example 4

The anti-tumor efficacy of phenanthriplatin, phenanthriplatin encapsulated NPs (construct 1) and phenanthriplatin conjugated NPs (construct 2), as described in example 3, in a PC3 xenograft mouse model was also examined.

Experimental Section

Animals.

In this study, 80 healthy, male BALB/c nu/nu mice at least 15-20 g and 6-8 weeks old were used.

Experiment Design And Doses.

Tumor Induction: The PC3 cell line was obtained from American Type Culture Collection (ATCC) and cultured. Cells from a cell suspension were counted using the Trypan-blue viability test using a hemocytometer. Each animal was inoculated subcutaneously in the right flank with 0.2 mL of a 50% RPMI1640 (serum free)/50% Matrigel™ mixture containing a suspension of tumor cells (5×10$^6$ cells/animal). Tumors were observed twice weekly until well established. Tumor weights were calculated using the formula:

$$\text{Tumor weight(mg)} = (a \times b^2 / 2)$$

where 'b' is the smallest diameter and 'a' is the largest diameter of the tumor as measured in millimeters with calipers.

Dose Administration.

On Day 1, phenanthriplatin, phenanthriplatin encapsulated NPs (construct 1; see Example 4), phenanthriplatin conjugated NPs (construct 2; see Example 4), and controls (PBS and cisplatin) were administered according to Table 12. The mice were treated twice a week for three weeks and monitored for an additional week. Tumor growth and body weight were monitored and recorded twice weekly. Mice were sacrificed 4 weeks following the first administration of chemotherapy, and organs were harvested in order to determine Pt concentrations.

TABLE 12

Study Design

| Groups | No. of Animals | Treatment | Dose (mg/kg) | Conc. (mg/ml) | Dose Volume (ml/kg) | Duration of Treatment |
|---|---|---|---|---|---|---|
| 1 | 10 | Control (PBS) | N/A | N/A | 10 | Twice a week for 3 weeks |
| 2 | 10 | Phenanthriplatin low-dose | 0.3 | 0.03 | 10 | Twice a week for 3 weeks |
| 3 | 10 | Phenanthriplatin high-dose | 3 | 0.3 | 10 | Twice a week for 3 weeks |
| 4 | 10 | Phenanthriplatin Encapsulated low-dose | 0.3 | 0.03 | 10 | Twice a week for 3 weeks |
| 5 | 10 | Phenanthriplatin Encapsulated high-dose | 3 | 0.3 | 10 | Twice a week for 3 weeks |
| 6 | 10 | Phenanthriplatin Conjugated low-dose | 0.3 | 0.03 | 10 | Twice a week for 3 weeks |
| 7 | 10 | Phenanthriplatin Conjugated high-dose | 3 | 0.3 | 10 | Twice a week for 3 weeks |
| 8 | 10 | Positive control (cisplatin) | 1.6 | 0.16 | 10 | Twice a week for 3 weeks |

Analysis of Pt Content in Mouse Organs.

The Organs (kidney, liver, spleen, and tumor) of all of the mice that survived until the 4 week end-point were digested for analysis of their Pt content by AAS. Generally, a tissue sample was incubated in 1 mL of 65% nitric acid overnight at room temperature. The sample was boiled at 65~70° C. for two days, cooled to room temperature, and the volume was adjusted to 10 ml (liver) or 3 ml (all others) with Milli-Q water. The Pt concentration was measured by AAS.

Results

Figure 11A:
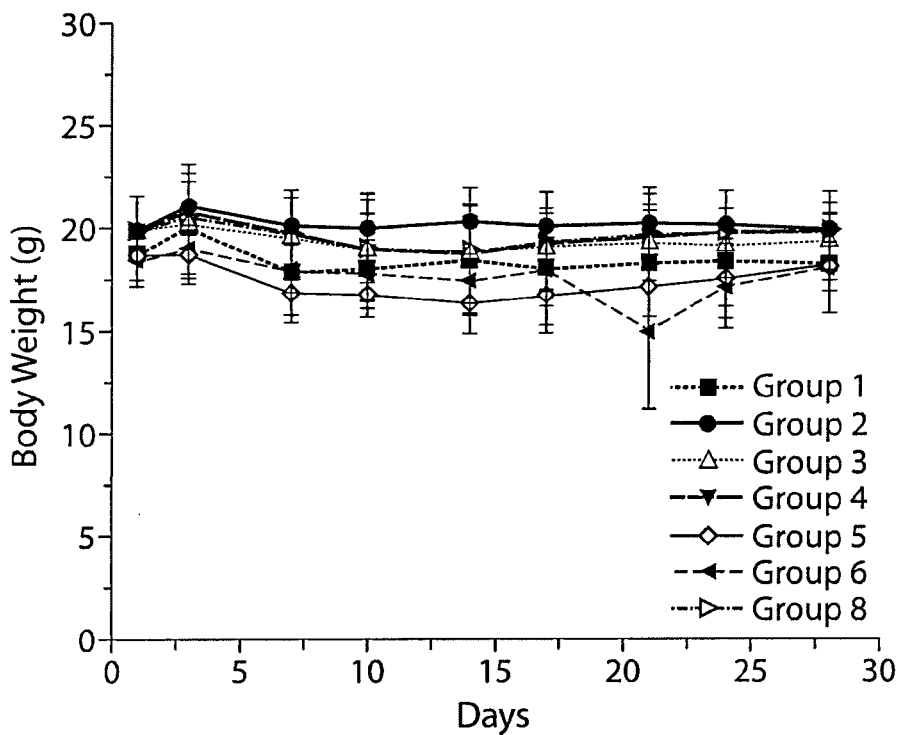
FIG. 11 shows the (A) effects of phenanthriplatin and phenanthriplatin-NPs on body weight of mice bearing PC3 xenograft. Body weight was measured at the indicated time points; and (B) effects of phenanthriplatin and phenanthriplatin-NPs on growth of PC3 prostate cancer xenografts, according to some embodiments.
Figure 11B:
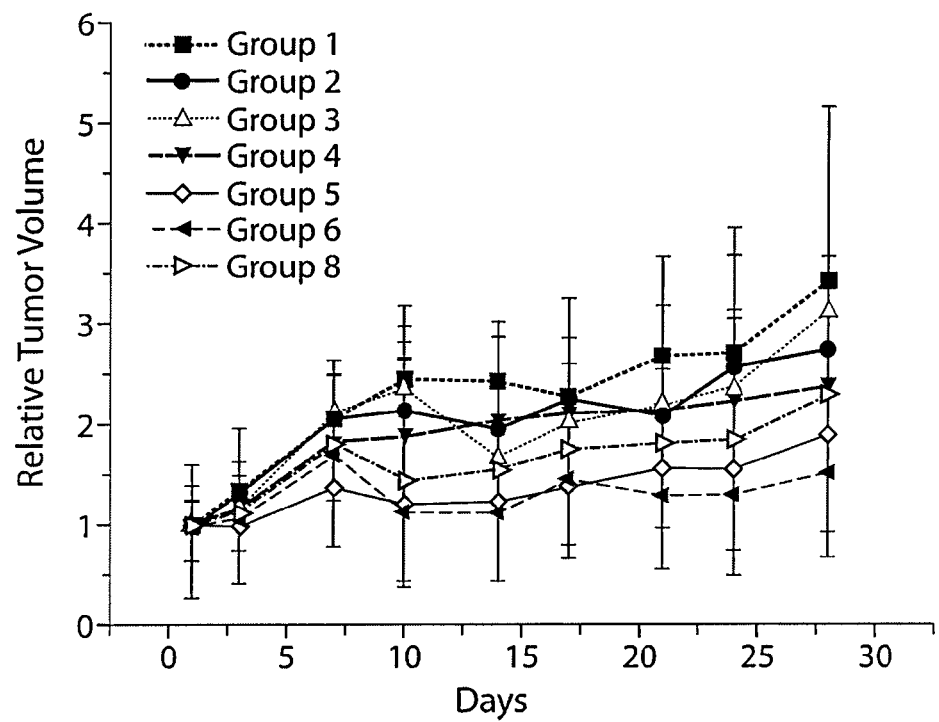

In FIG. 11: (A) Effects of phenanthriplatin and phenanthriplatin-NPs on body weight of mice bearing PC3 xenograft. Body weight was measured at the indicated time points. (B) Effects of phenanthriplatin and phenanthriplatin-NPs on growth of PC3 prostate cancer xenografts.

Figure 12:
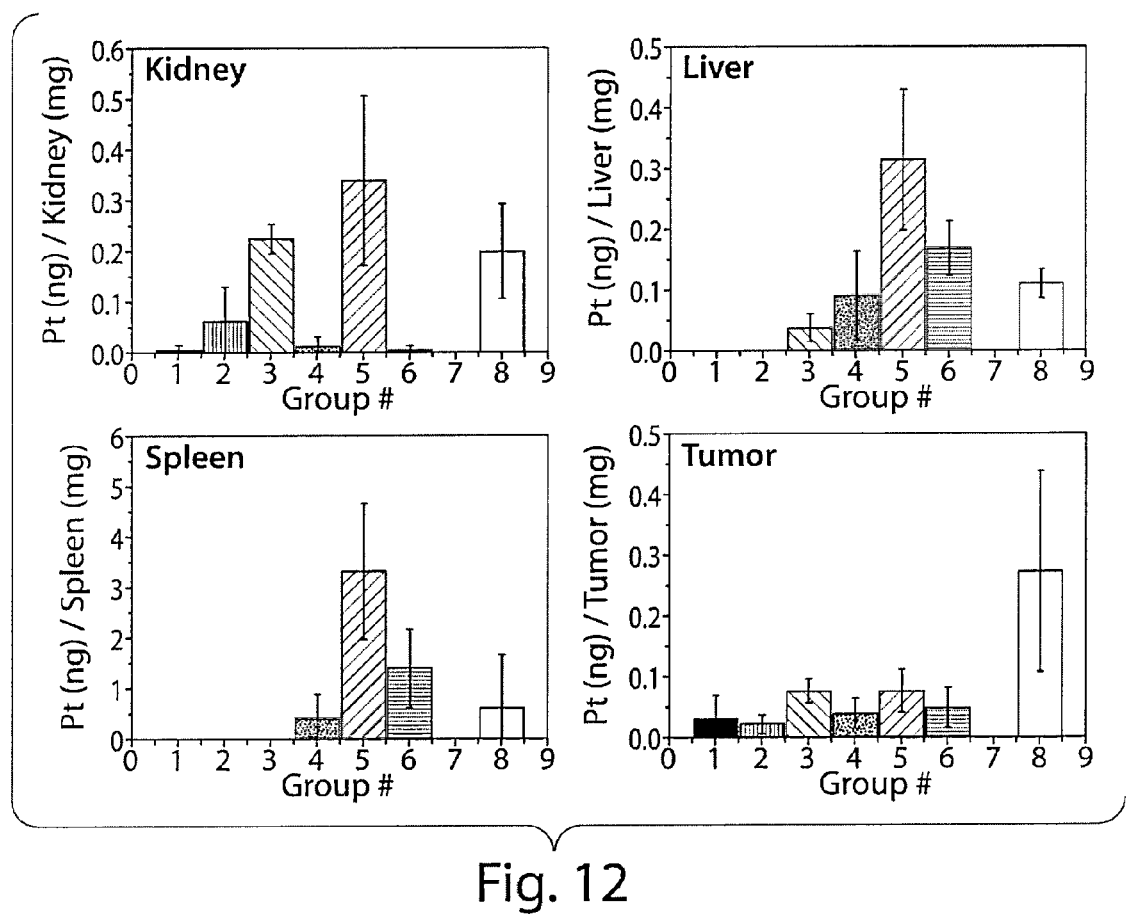
FIG. 12 shows the distribution of Pt in mouse organs, according to some embodiments.

In FIG. 12: Distribution of Pt in mouse organs.

Example 5

The transcription profiles of gaussia luciferase expression vectors containing site-specific phenanthriplatin-dna lesions in live mammalian cells was also analyzed.

Phenanthriplatin was incorporated site-specifically into Gaussia luciferase expression vectors. Transcription inhibition effects of phenanthriplatin have been determined in the mammalian cancer cells from different origins. Phenanthriplatin showed significant transcription inhibition effects in the cell lines tested. The pattern of the transcription recovery of phenanthriplatin-dG lesion matched with that of the cytotoxicity of the compound in most of the cells tested, indicating a key role of cellular repair of phenanthriplatin-DNA damage in mediating cytotoxicity of the compound.

Experimental Section

Vector Construction and Preparation. The Gaussia luciferase expression vector for incorporation of site-specific phenanthriplatin-dG lesion, pGLuc8temG, was prepared following protocols reported previously (e.g., see *J Am Chem Soc* 2010, 132, 7429-7435). Preparation of Platinated Insertion Strand. A 16-mer oligonucleotide containing a site-specific cis-$[Pt(NH_3)_2(phen)]^{2+}$-dG (phen=phenanthridine) lesion was prepared. A 25.7 mM aqueous solution of phenanthriplatin was activated by addition of 0.98 equiv of $AgNO_3$ followed by agitation for 8 h in the dark at room temperature. The suspension was centrifuged. To a solution of 0.2 mM 16-mer oligonucleotide 5'-CCTCCTCG*TCTCTTCC (SEQ ID NO: 1; where the asterisk denotes the base to be platinated) in 10 mM $NaH_2PO_4$ (pH 6.3), 1.2 equiv of activated phenanthriplatin was added. The reaction mixture was incubated in the dark at 37° C. overnight. The reaction was stopped when the solution was frozen. Phenanthriplatin-modified insertion strand was purified by ion exchange HPLC (Dionex DNAPac PA-100, linear gradient, 0.34 to 0.45 M NaCl in 25 mM Tris-HCl (pH 7.4) over 11 min). After purification, the platinated DNA solution was dialyzed against $H_2O$ and lyophilized. The platination level was confirmed by UV-vis and atomic absorption spectroscopy, which yielded a Pt/DNA ratio of 1.02±0.02. The insertion strand was further analyzed for nucleotide composition by nuclease S1 digestion to confirm the platination site following a protocol published previously (Table 13) (e.g., see J Am Chem Soc 2007, 129, 6370-6371). The platinated and unplatinated DNA strands (40 μM) were phosphorylated by T4 PNK (0.67 U/μL) at 37° C. for 3 h, followed by a phenol/chloroform/isoamyl alcohol extraction to remove the enzyme. The phosphorylated DNA strands were ethanol precipitated and stored in −80° C. at a concentration of 100 pmol/μL.

Chem 2009, 20, 1058-1063). Briefly, a 600 μg quantity of pGLuc8temG plasmid was digested with 30 U Nt.BbvCI at 37° C. for 1 h. The reaction mixture was heated at 80° C. for 20 min to deactivate the enzyme, followed by a phenol/chloroform/isoamyl alcohol extraction to remove the enzyme. The mixture was dialyzed against $H_2O$ overnight at 4° C. The plasmid was further digested with 30 U Nt.BspQI at 50° C. for 1 h, and the enzyme was heat-deactivated and removed by a phenol/chloroform/isoamyl alcohol extraction. The nicked plasmid was mixed with 1,000 equiv of complementary DNA strand 5'-TTTTGGAAGAGACGAGGAGGTTTT (SEQ ID NO: 2) in a buffer of 10 mM Tris-HCl, 2 mM $MgCl_2$, 0.4 M NaCl, pH 7.4, heated at 80° C. for 5 min, and subsequently cooled at 4° C. for 5 min for 10 cycles. The gapped plasmid was purified by isopycnic centrifugation at 58,000 rpm, 20° C. for 24 h, and quantitated by UV-vis spectroscopy. A 120 μg quantity of the gapped plasmid was annealed with 100 equiv of the insertion strand in a buffer of 10 mM Tris-HCl, 2 mM $MgCl_2$, 0.4 M NaCl, pH 7.4 from 90° C. to 4° C. at −1° C./min in a thermocycler. The platinated plasmid was dialyzed against $H_2O$ at 4° C. overnight and further purified by treatment with 30 U BsmBI at 55° C. for 1 h. The closed-circular form of plasmid was purified and concentrated by isopycnic centrifugation, followed by n-butanol extraction and ethanol precipitation. The plasmids were quantitated by a Quant-iT™ PicoGreen® dsDNA Kit from Invitrogen (Carlsbad, Calif.), and stored in −80° C. in TE buffer (10 mM Tris-HCl, 2 mM EDTA, pH 7.4).

Restriction Analysis of Site-Specifically Platinated Plasmids.

To carry out a restriction analysis on ligated platinated or unplatinated plasmids, a 100 ng quantity of pGLuc8temG plasmid was incubated with 2 U BsmBI at 55° C. for 30 min. The plasmids were analyzed using 0.8% agarose gel electrophoresis containing 0.5 μg/mL ethidium bromide. The gels were documented with a BioRad Fluor-S Multilmager.

Transient Transfection of Cells and GLuc Reporter Transcription Assays.

Transfection of platinated plasmids into mammalian cells was carried out as reported previously (e.g., see *ChemBioChem* 2011, 12, 1115-1123). A549 and HeLa cells were plated at 2,000 cells per well in 96-well plates. NTera-2 and HT29 cells were plated at 4,000 cells per well in 96-well plates. MCF7 and U2OS cells were plated at 5,000 cells per well in 96-well plates. The cells were allowed to attach and grow for 48 h, and then washed with antibiotic-free culture media right before transfection. Transient transfection of the cells was carried out using Lipofectamine 2000. Briefly, 10 ng of site specifically platinated probes was included in each well. The experiments were performed in quadruplicate. The

TABLE 13

Characterization of the insertion strands by nucleotide composition analysis.

| Insertion strand | dC obs'd | dC calc'd | dG obs'd | dG calc'd | T obs'd | T calc'd | dA obs'd | dA calc'd |
|---|---|---|---|---|---|---|---|---|
| 8temG-IS | 9.0 | 9 | 1.0 | 1 | 6.0 | 6 | 0.0 | 0 |
| 8temG-IS-ppt | 9.0 | 9 | 0.0 | 0 | 6.0 | 6 | 0.0 | 0 |

Preparation of Site-Specifically Platinated pGLuc Probes.

Site-specifically platinated pGLuc8temG plasmid containing a cis-$[Pt(NH_3)_2(phen)]^{2+}$-dG lesion between the CMV promoter and luciferase expression gene was prepared following the strategy published previously (e.g., see Bioconjug probes were diluted in OptiMEM, and Lipofectamine was diluted in OptiMEM. The two solutions were combined and incubated for 20 min. The transfection mixture was delivered into each well, and the cells were incubated for 2 h. The cells were washed with antibiotic-free culture media to remove the transfection mixture. A 100 µL volume of fresh, antibiotic-free media was added into each well to start the transcription assay. Media were collected at 8, 16, 24, 32, 44 h and kept at 4° C. until GLuc reporter gene assays were carried out as described previously (e.g., see Chem Bio Chem 2011, 12, 1115-1123).

Results

Transcription Inhibition Effects of Phenanthriplatin in Different Mammalian Cancer Cells.

Figure 13:
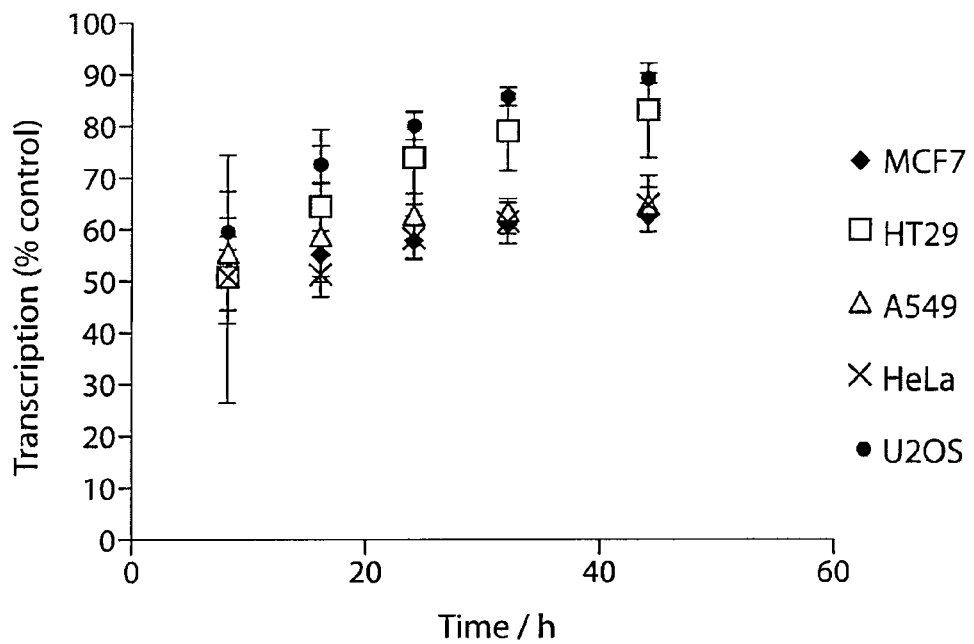
FIG. 13 shows the transcription inhibition effects of phenanthriplatin-dG lesion in different human cancer cells, according to some embodiments.

The transcription profiles of Gaussia luciferase expression vectors containing site-specific phenanthriplatin-dG lesion were studied in human cancer cells from different origins: NTera-2, HT29, MCF7, HeLa, A549, and U2OS (FIG. 13). The pGLuc8temG+IS and pGLuc8temG+IS-ppt were transfected into the cells utilizing standard liposome reagents, and transcription levels of secreted Gaussia luciferase were monitored at 8, 16, 24, 32, and 44 h using a Gaussia luciferase assay (e.g., see Chem Bio Chem 2011, 12, 1115-1123). The transcription level of platinated plasmid was subsequently normalized against that of unplatinated control (FIG. 13). Transcription control) was 100 for NoPt, 24 at 8 hours, 26 at 16 hours, 32 at 24 hours, 36 at 32 hours, and 41 at 44 hours.

A site-specific cis-$[Pt(NH_3)_2(phen)]^{2+}$-dG lesion illustrated strong transcription inhibition effects in most of the cell lines tested. These data indicated that phenanthriplatin is a strong transcription inhibitor in live mammalian cancer cells.

In FIG. 13: Transcription inhibition effects of phenanthriplatin-dG lesion in different human cancer cells.

The recovery rates of transcription for phenanthriplatin in human cancer cells from different origins were calculated (Table 14). The S value was defined as the ratio of recovery of transcription level vs. time. A higher S value indicated that the DNA damage from the compound is easier to be repaired. In all the cell lines tested, A549 cells showed the smallest S value, indicating that phenanthriplatin-DNA lesions were more difficult to be removed in this lung cancer cells. In contrast, the S value was higher in HT29 cells than those in other cells, showing that the colon cancers cells illustrated a greater ability to remove phenanthriplatin-DNA lesions. The $IC_{50}$ values of phenanthriplatin are listed in Table 14 also. The transcription recovery of phenanthriplatin was compared to the cytotoxicity of the compounds.

TABLE 14

The recovery rates of transcription (S) from phenanthriplatin-modified plasmids and cytotoxicity of phenanthriplatin ($IC_{50}$), determined by MTT assay, in different human cancer cells.

| Cell line | S | $IC_{50}$ (µM) |
|---|---|---|
| MCF7 | 0.337 | 1.14 ± 0.02 |
| HT29 | 0.884 | 2.02 ± 0.04 |
| A549 | 0.263 | 0.17 ± 0.01 |
| HeLa | 0.434 | 0.37 ± 0.04 |
| U2OS | 0.805 | 1.05 ± 0.02 |

Figure 14:
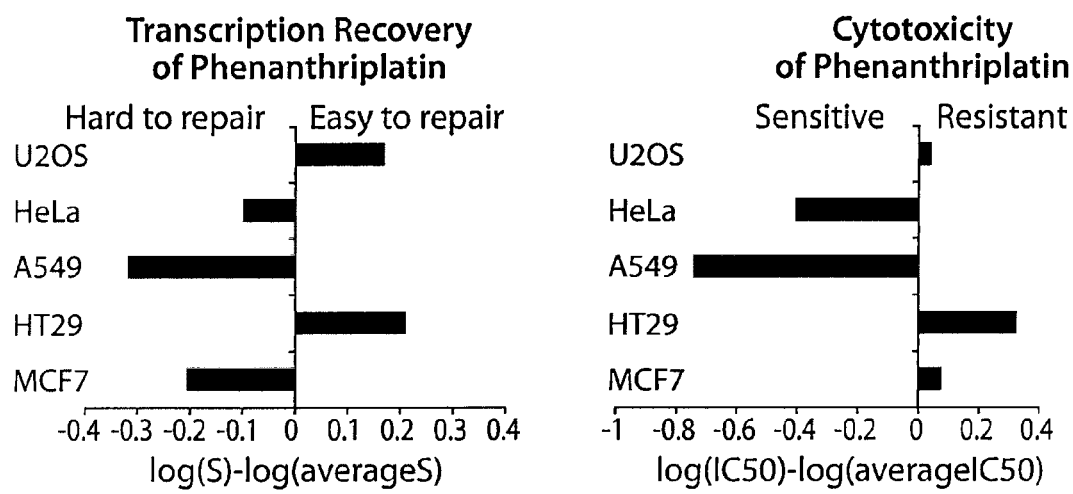
FIG. 14 shows comparative analysis of transcription recovery of phenanthriplatin (left panel) and cytotoxicity of phenanthriplatin (right panel), according to some embodiments.

The rate of transcription recovery, calculated as log(S)–log(averageS), where the S is the rate in individual cell line and the averageS is the average of S values in the five cell lines tested, was plotted for each of the cells (FIG. 14, left panel). A bar towards the left indicates that the damage is more difficult to be repaired in the cells. The log($IC_{50}$)–log(average$IC_{50}$) was plotted for each cell line as well (FIG. 14, right panel), and a bar towards the left shows that the compound is more active in the particular cells. The pattern of the transcription recovery of phenanthriplatin-dG lesion matched with that of the cytotoxicity of the compound in U2OS, HeLa, A549, and HT29 cells. For example, the phenanthriplatin-DNA lesions were the most difficult to be removed in A549 cells, and the cytotoxicity of the compound was the highest in the A549 lung cancer cells. The phenanthriplatin-DNA lesions were easier to be repaired in HT29 and U2OS cells, and the compound showed lower cytotoxicity in those two cell lines (FIG. 14). These results indicate that cellular repair of phenanthriplatin-DNA damage may play a key role in mediating the cytotoxicity of the compound.

In FIG. 14: Comparative analysis of transcription recovery of phenanthriplatin (left panel) and cytotoxicity of phenanthriplatin (right panel).

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed:

1. A composition comprising a compound having the structure:

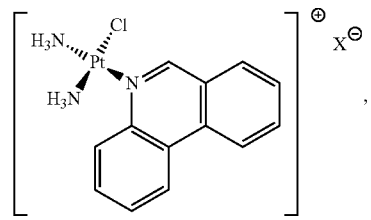

wherein
X⁻ is a counterion.

2. A pharmaceutical composition, comprising:
a composition of claim 1; and
one or more pharmaceutically acceptable carriers, additives and/or diluents.

3. A kit for the treatment of cancer, comprising:
a composition of claim 1; and
instructions for use of the composition for treatment of cancer.

4. A method of treating cancer in a patient in need of treatment for cancer, comprising:
administering a composition of claim 1 to the patient.

SEQUENCE LISTING

```
<160> NUMBER OF SEQ ID NOS: 2

<210> SEQ ID NO 1
<211> LENGTH: 16
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (9)..(9)
<223> OTHER INFORMATION: to be platinated

<400> SEQUENCE: 1
cctcctcgtc tcttcc                                              16

<210> SEQ ID NO 2
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 2
ttttggaaga gacgaggagg tttt                                     24
```

5. The composition of claim 1, wherein the compound has the structure:

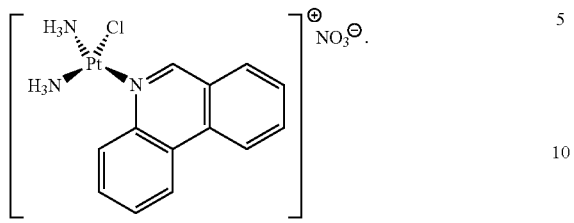

6. A pharmaceutical composition, comprising:
a composition of claim 5; and
one or more pharmaceutically acceptable carriers, additives and/or diluents.

7. A kit for the treatment of cancer, comprising:
a composition of claim 5; and
instructions for use of the composition for treatment of cancer.

8. A method of treating cancer in a patient in need of treatment for cancer, comprising: administering a composition of claim 5 to the patient.

* * * * *